(12) United States Patent
Scott et al.

(10) Patent No.: US 12,213,699 B2
(45) Date of Patent: Feb. 4, 2025

(54) THREADED CANNULA DEPTH LIMITER

(71) Applicant: Cilag GmbH International, Zug (CH)

(72) Inventors: Gregory G. Scott, Cincinnati, OH (US); Jonathan M. Cepress, Cincinnati, OH (US); David L. Collins, Cincinnati, OH (US); Matthew S. Corbin, Placentia, CA (US); Jeffrey L Savage, West Chester, OH (US)

(73) Assignee: Cilag GmbH International, Zug (CH)

( * ) Notice: Subject to any disclaimer, the term of this patent is extended or adjusted under 35 U.S.C. 154(b) by 892 days.

(21) Appl. No.: 17/213,415

(22) Filed: Mar. 26, 2021

(65) Prior Publication Data

US 2021/0338274 A1  Nov. 4, 2021

Related U.S. Application Data

(60) Provisional application No. 63/018,650, filed on May 1, 2020.

(51) Int. Cl.
    *A61B 17/34* (2006.01)
(52) U.S. Cl.
    CPC ...... *A61B 17/3423* (2013.01); *A61B 17/3494* (2013.01); *A61B 2017/3458* (2013.01)
(58) Field of Classification Search
    CPC ............ A61B 17/3423; A61B 17/3494; A61B 2017/3458; A61B 17/3417; A61B 2017/3492
    See application file for complete search history.

(56) References Cited

U.S. PATENT DOCUMENTS

| 3,817,251 A | 6/1974 | Hasson |
| 3,896,527 A | 7/1975 | Miller et al. |

(Continued)

FOREIGN PATENT DOCUMENTS

| AU | 702882 B2 | 3/1993 |
| CN | 106344126 B | 2/2019 |

(Continued)

OTHER PUBLICATIONS

European Examination Report dated Jul. 26, 2023 for Application No. EP 21722871, 4 pgs.

(Continued)

*Primary Examiner* — Bradley J Osinski
(74) *Attorney, Agent, or Firm* — Frost Brown Todd LLP

(57) ABSTRACT

A surgical access device assembly. The assembly includes a cannula having a working channel and a helical tissue engagement feature disposed along an outer surface of the cannula and configured to stabilize the cannula relative to a body cavity wall of a patient. The assembly also includes a depth limiter movably coupled with the cannula. The depth limiter includes a body portion extending about a central axis of the depth limiter and including a protrusion extending radially inwardly relative to the central axis. The body portion is movable angularly relative to the cannula between a fine adjustment configuration and a coarse adjustment configuration. In the fine adjustment configuration the protrusion is configured to selectively threadably engage the helical tissue engagement feature. In the coarse adjustment configuration the protrusion is configured to selectively threadably disengage the helical tissue engagement feature such that the depth limiter is translatable axially along the cannula.

20 Claims, 30 Drawing Sheets

(56) References Cited

U.S. PATENT DOCUMENTS

| | | | |
|---|---|---|---|
| 4,699,616 A | 10/1987 | Nowak et al. | |
| 5,002,557 A | 3/1991 | Hasson | |
| 5,147,316 A * | 9/1992 | Castillenti | A61B 17/3421 604/174 |
| 5,215,531 A | 6/1993 | Maxson et al. | |
| D338,270 S | 8/1993 | Stephens et al. | |
| 5,256,147 A | 10/1993 | Vidal et al. | |
| 5,257,975 A | 11/1993 | Foshee | |
| 5,263,939 A | 11/1993 | Wortrich | |
| 5,267,970 A | 12/1993 | Chin et al. | |
| 5,290,249 A | 3/1994 | Foster et al. | |
| 5,364,372 A | 11/1994 | Danks et al. | |
| D354,562 S | 1/1995 | Medema | |
| 5,540,675 A | 7/1996 | Hasson | |
| 5,697,913 A | 12/1997 | Sierocuk et al. | |
| 5,792,135 A | 8/1998 | Madhani et al. | |
| 5,800,451 A | 9/1998 | Buess et al. | |
| 5,817,061 A | 10/1998 | Goodwin et al. | |
| 5,833,666 A | 11/1998 | Davis et al. | |
| 5,836,913 A | 11/1998 | Orth et al. | |
| 5,855,566 A | 1/1999 | Dunlap et al. | |
| 5,951,588 A | 9/1999 | Moenning | |
| 5,957,888 A | 9/1999 | Hinchcliffe | |
| 6,432,085 B1 | 8/2002 | Stellon et al. | |
| 6,451,041 B1 | 9/2002 | Moenning et al. | |
| 6,620,173 B2 | 9/2003 | Gerbi et al. | |
| 6,632,197 B2 | 10/2003 | Lyon | |
| 6,638,265 B1 | 10/2003 | Ternamian | |
| 6,652,490 B2 | 11/2003 | Howell | |
| 6,808,492 B2 | 10/2004 | Snyder | |
| 7,235,064 B2 | 6/2007 | Hopper et al. | |
| 7,473,220 B2 | 1/2009 | Francese et al. | |
| 7,981,092 B2 | 7/2011 | Duke | |
| 8,147,453 B2 | 4/2012 | Albrecht et al. | |
| 8,226,553 B2 | 7/2012 | Shelton, IV et al. | |
| 8,251,900 B2 | 8/2012 | Ortiz et al. | |
| 8,287,503 B2 | 10/2012 | Albrecht et al. | |
| 8,479,969 B2 | 7/2013 | Shelton, IV | |
| 8,568,362 B2 | 10/2013 | Moreno, Jr. et al. | |
| 8,573,465 B2 | 11/2013 | Shelton, IV | |
| 8,579,807 B2 | 11/2013 | Moreno, Jr. et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 8,821,527 B2 | 9/2014 | Farnan et al. | |
| 8,939,946 B2 | 1/2015 | Albrecht et al. | |
| 9,004,545 B2 | 4/2015 | Whitaker et al. | |
| 9,259,238 B2 | 2/2016 | Albrecht et al. | |
| 9,289,200 B2 | 3/2016 | Dang et al. | |
| 9,522,265 B2 | 12/2016 | Pravong et al. | |
| 9,668,723 B2 * | 6/2017 | Keating | A61B 17/0469 |
| 9,675,379 B2 | 6/2017 | Kucklick | |
| 10,327,805 B2 | 6/2019 | Hibner et al. | |
| 10,327,809 B2 | 6/2019 | Buyda et al. | |
| 10,576,259 B2 | 3/2020 | Stafford | |
| 10,792,069 B2 | 10/2020 | Hall et al. | |
| 10,820,924 B2 | 11/2020 | Hall et al. | |
| 11,359,751 B2 | 6/2022 | White et al. | |
| 11,712,267 B2 | 8/2023 | McLain | |
| 2005/0113856 A1 | 5/2005 | Epstein et al. | |
| 2005/0165432 A1 | 7/2005 | Heinrich | |
| 2007/0225643 A1 | 9/2007 | Hopper et al. | |
| 2009/0182282 A1 | 7/2009 | Okihisa et al. | |
| 2010/0010449 A1 | 1/2010 | Leibowitz et al. | |
| 2010/0057010 A1 | 3/2010 | Göransson | |
| 2013/0060084 A1 | 3/2013 | Fouts et al. | |
| 2014/0066953 A1 | 3/2014 | Keating et al. | |
| 2016/0015423 A1 | 1/2016 | Ravikumar et al. | |
| 2017/0245889 A1 | 8/2017 | Herrell et al. | |
| 2017/0311932 A1 | 11/2017 | Rebellino | |
| 2018/0199959 A1 | 7/2018 | Lee | |
| 2018/0206883 A1 | 7/2018 | McIntyre et al. | |
| 2018/0214140 A1 | 8/2018 | Nock et al. | |
| 2019/0000496 A1 | 1/2019 | Shelton, IV et al. | |
| 2019/0083071 A1 | 3/2019 | Rebellino et al. | |
| 2019/0150900 A1 | 5/2019 | Choung et al. | |
| 2019/0254703 A1 | 8/2019 | Ciampini et al. | |
| 2019/0254704 A1 | 8/2019 | Buyda et al. | |
| 2019/0380742 A1 | 12/2019 | Hall et al. | |
| 2020/0205855 A1 * | 7/2020 | Aravalli | A61B 17/3496 |
| 2021/0338269 A1 | 11/2021 | Scott et al. | |
| 2021/0338272 A1 | 11/2021 | Muthuchidambaram et al. | |
| 2021/0338273 A1 | 11/2021 | Vijayachandran et al. | |
| 2021/0338275 A1 | 11/2021 | Vijayachandran | |
| 2021/0338276 A1 | 11/2021 | Scott | |
| 2021/0338278 A1 | 11/2021 | Scott et al. | |
| 2021/0338281 A1 | 11/2021 | Mozloom, Jr. et al. | |
| 2021/0338282 A1 | 11/2021 | Vijayachandran | |
| 2021/0338283 A1 | 11/2021 | McLain | |
| 2021/0338371 A1 | 11/2021 | Harris et al. | |

FOREIGN PATENT DOCUMENTS

| | | |
|---|---|---|
| DE | 202007001745 U1 | 4/2007 |
| EP | 2174602 A1 | 4/2010 |
| EP | 3210553 B1 | 10/2019 |
| WO | WO 1999/052457 A1 | 10/1999 |
| WO | WO 2004/032756 A2 | 4/2004 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

European Examination Report dated Jul. 20, 2023 for Application No. EP 21723218, 5 pgs.

European Examination Report dated Sep. 15, 2023 for Application No. EP 21722865, 5 pgs.

European Examination Report dated Aug. 10, 2023 for Application No. EP 21722862, 5 pgs.

International Search Report and Written Opinion dated Jul. 22, 2021, for International Application No. PCT/EP2021/061421, 15 pages.

International Search Report and Written Opinion dated Aug. 3, 2021, for International Application No. PCT/EP2021/061428, 15 pages.

International Search Report and Written Opinion dated Jul. 16, 2021, for International Application No. PCT/EP2021/061442, 13 pages.

International Search Report and Written Opinion dated Jul. 8, 2021, for International Application No. PCT/EP2021/061447, 15 pages.

International Search Report and Written Opinion dated Jul. 27, 2021, for International Application No. PCT/EP2021/061456, 14 pages.

International Search Report and Written Opinion dated Jul. 13, 2021, for International Application No. PCT/EP2021/061459, 16 pages.

International Search Report and Written Opinion dated Jul. 20, 2021, for International Application No. PCT/EP2021/061466, 17 pages.

International Search Report and Written Opinion dated Jul. 15, 2021, for International Application No. PCT/EP2021/061468, 16 pages.

* cited by examiner

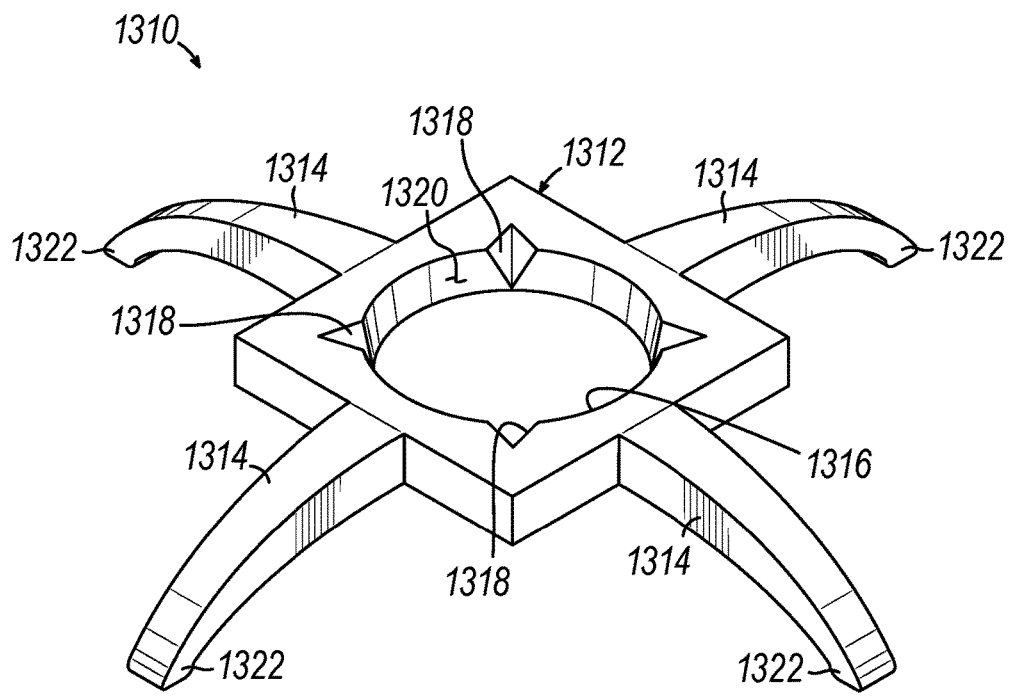
FIG. 28
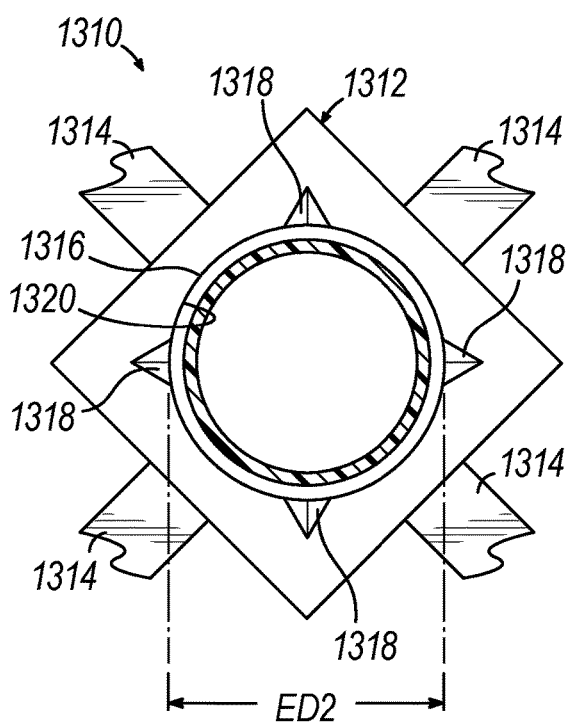 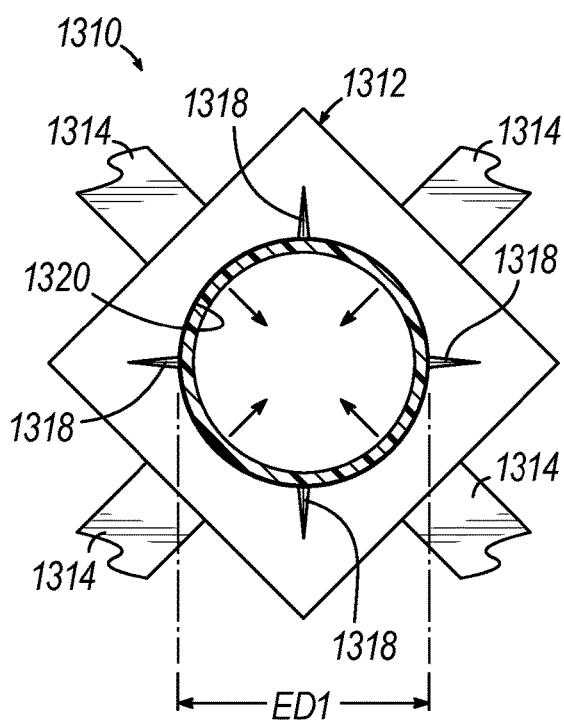
FIG. 29A  FIG. 29B

THREADED CANNULA DEPTH LIMITER

PRIORITY

This application claims priority to U.S. Provisional Patent App. No. 63/018,650, entitled "Threaded Cannula Depth Limiter," filed May 1, 2020, the disclosure of which is incorporated by reference herein.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 28 depicts a perspective view of another exemplary depth limiter that includes a hub with notches;

FIG. 29A depicts a top plan view of the depth limiter of FIG. 28 coupled with the cannula tube of the cannula assembly of FIG. 5, where the hub of the depth limiter is in a movable configuration;

FIG. 29B depicts a partial side sectional view of the depth limiter of FIG. 28 coupled with the cannula tube of the cannula assembly of FIG. 5 following detachment and removal of the obturator, where the legs of the depth limiter are in a fixed configuration;

Figure 1:
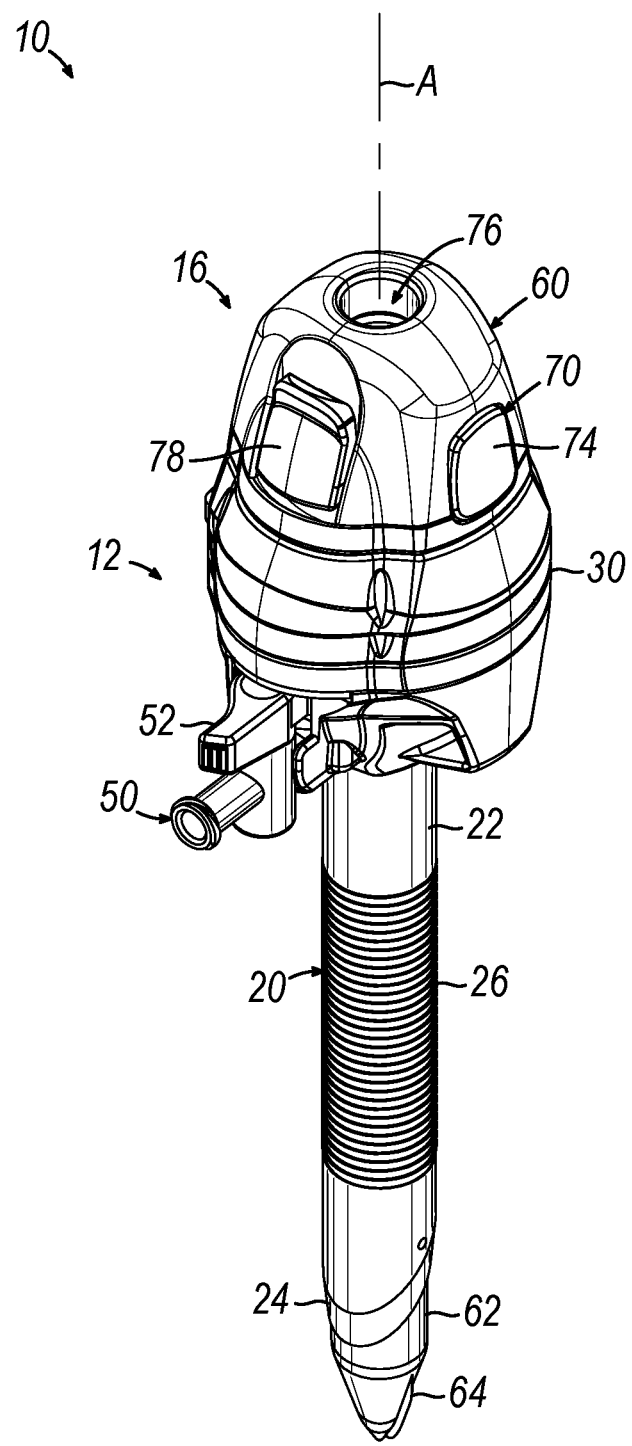
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

Figure 2:
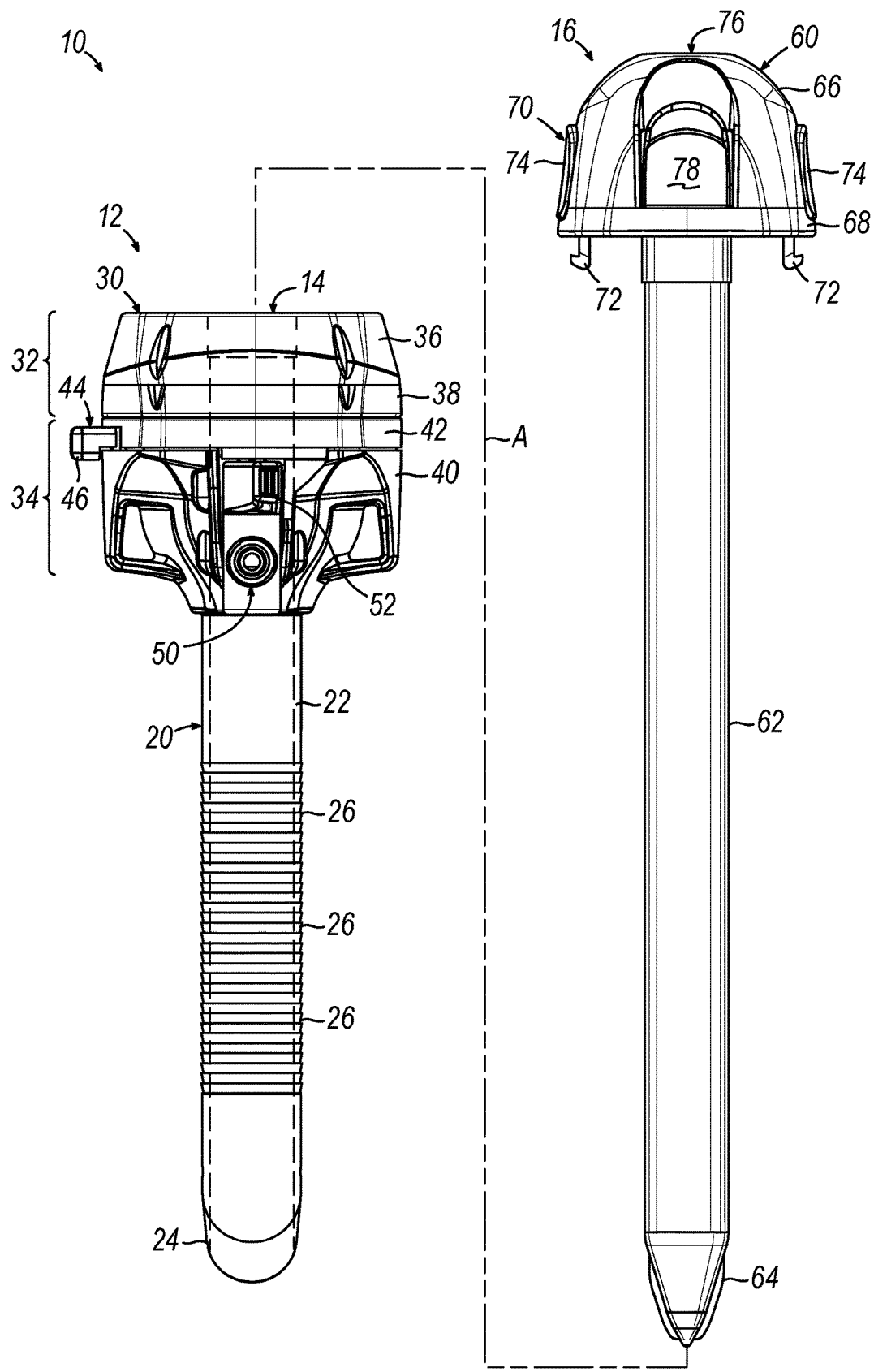
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever

(78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar Into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
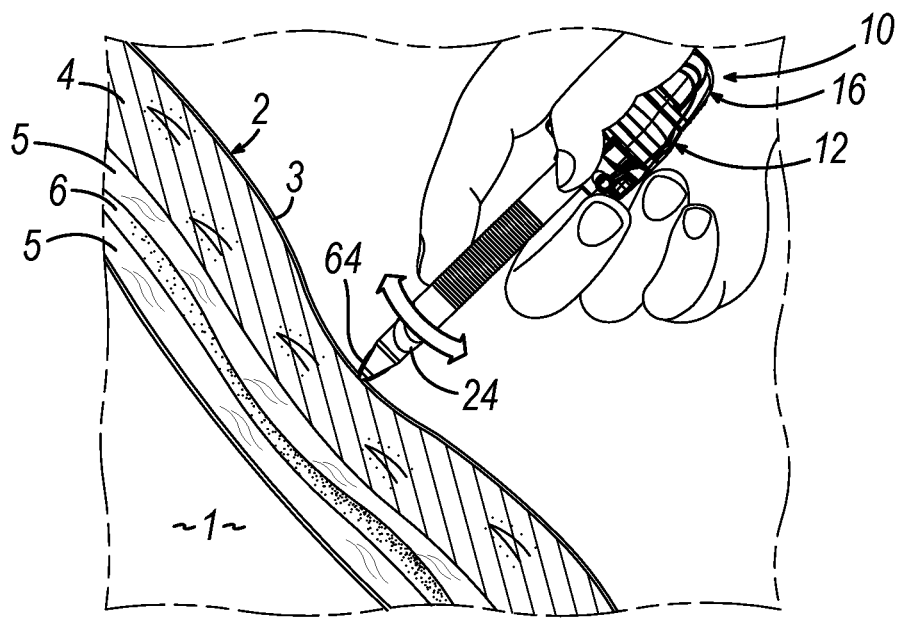
FIG. 3A depicts a side sectional view of the trocar of FIG. 1 being manipulated by a clinician through tissue layers of an abdominal wall.
Figure 3B:
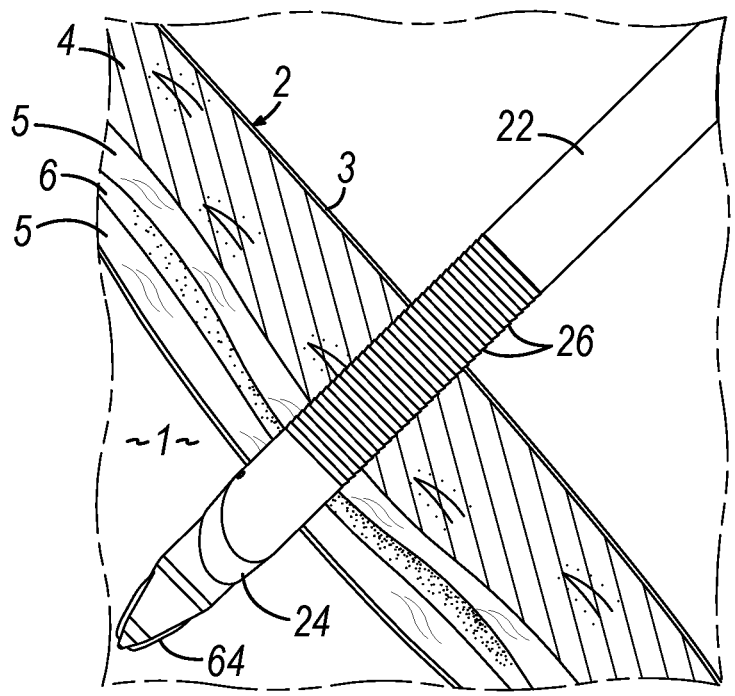
FIG. 3B depicts an enlarged side sectional view of the trocar of FIG. 1, showing a distal end of the trocar received within the abdominal cavity of FIG. 3A.
Figure 3C:
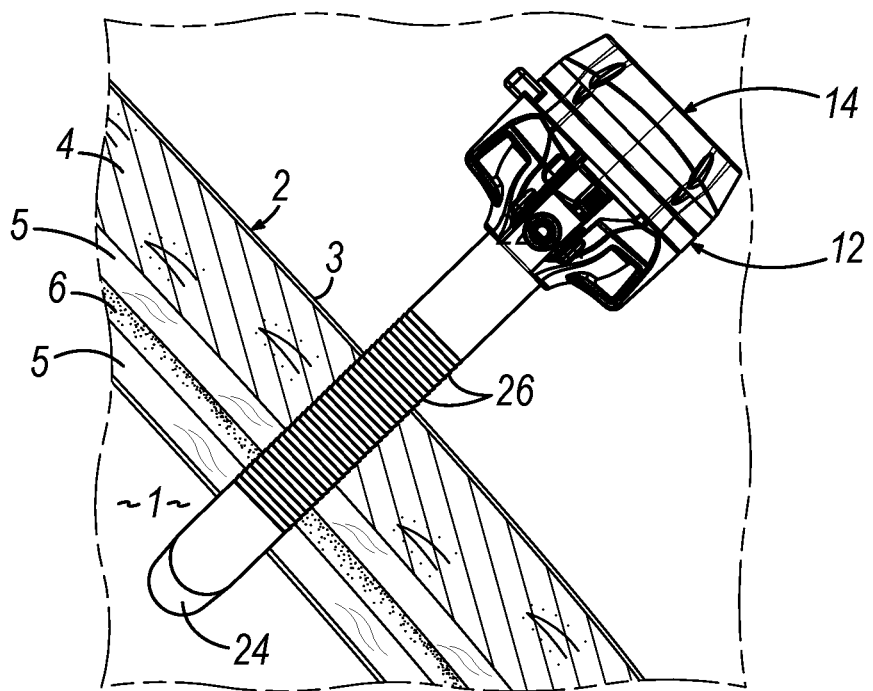
FIG. 3C depicts a side sectional view of the cannula assembly of FIG. 1, showing the cannula assembly remaining positioned within the abdominal wall of FIG. 3A following detachment and removal of the obturator.
Figure 3D:
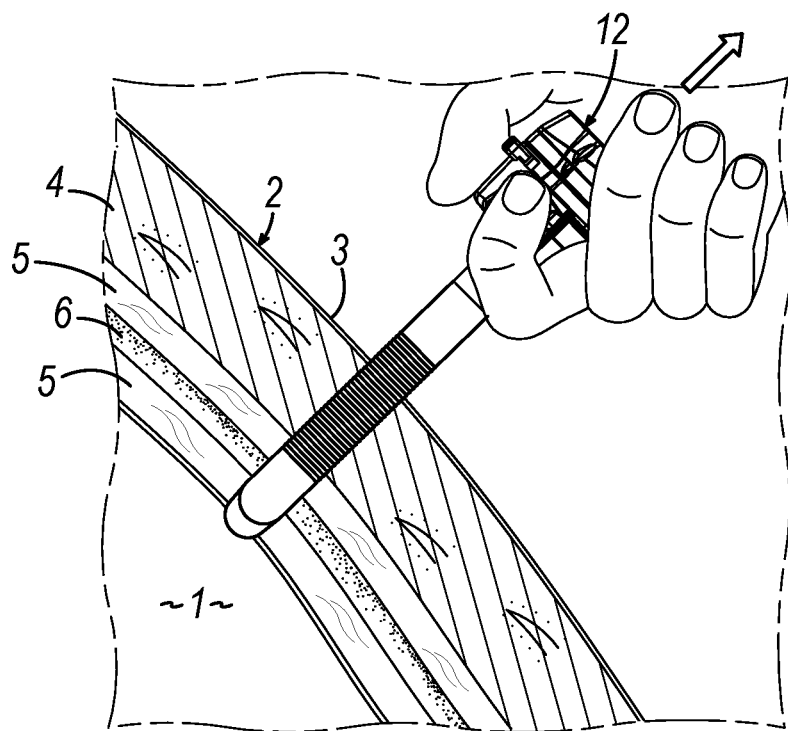
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
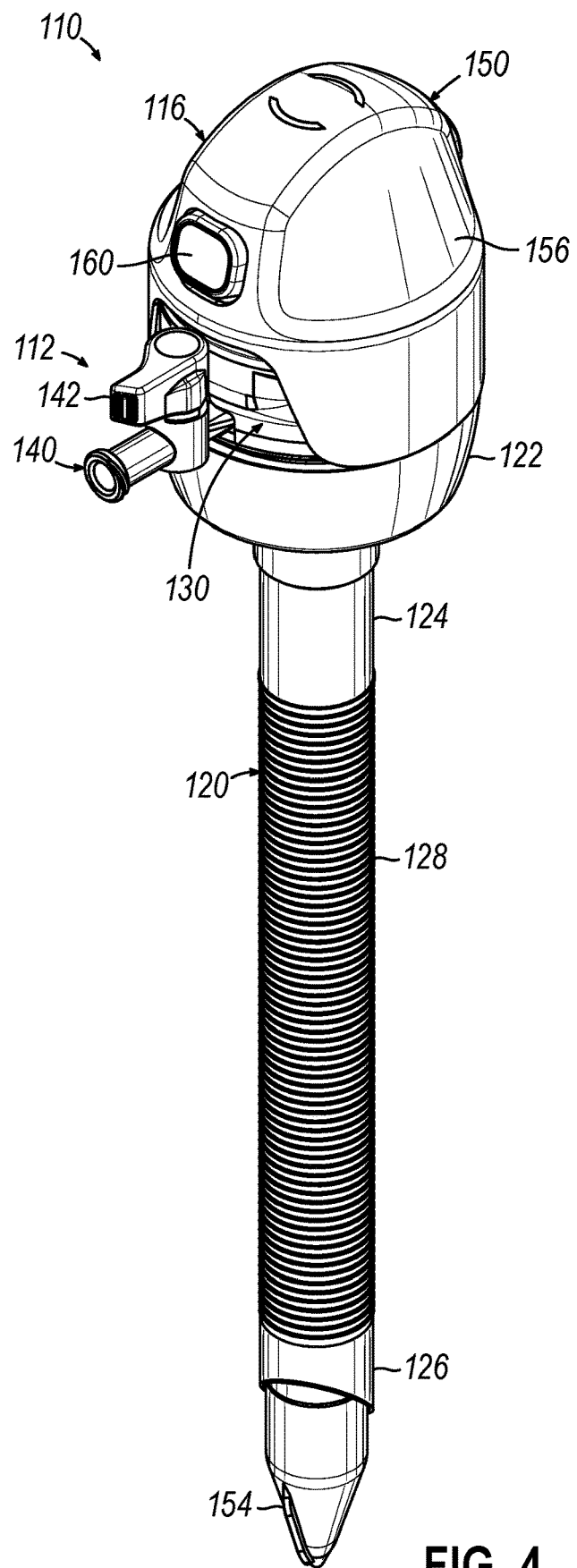
FIG. 4 depicts a perspective view of another exemplary trocar having a cannula assembly and an obturator shown in an assembled state.
Figure 5:
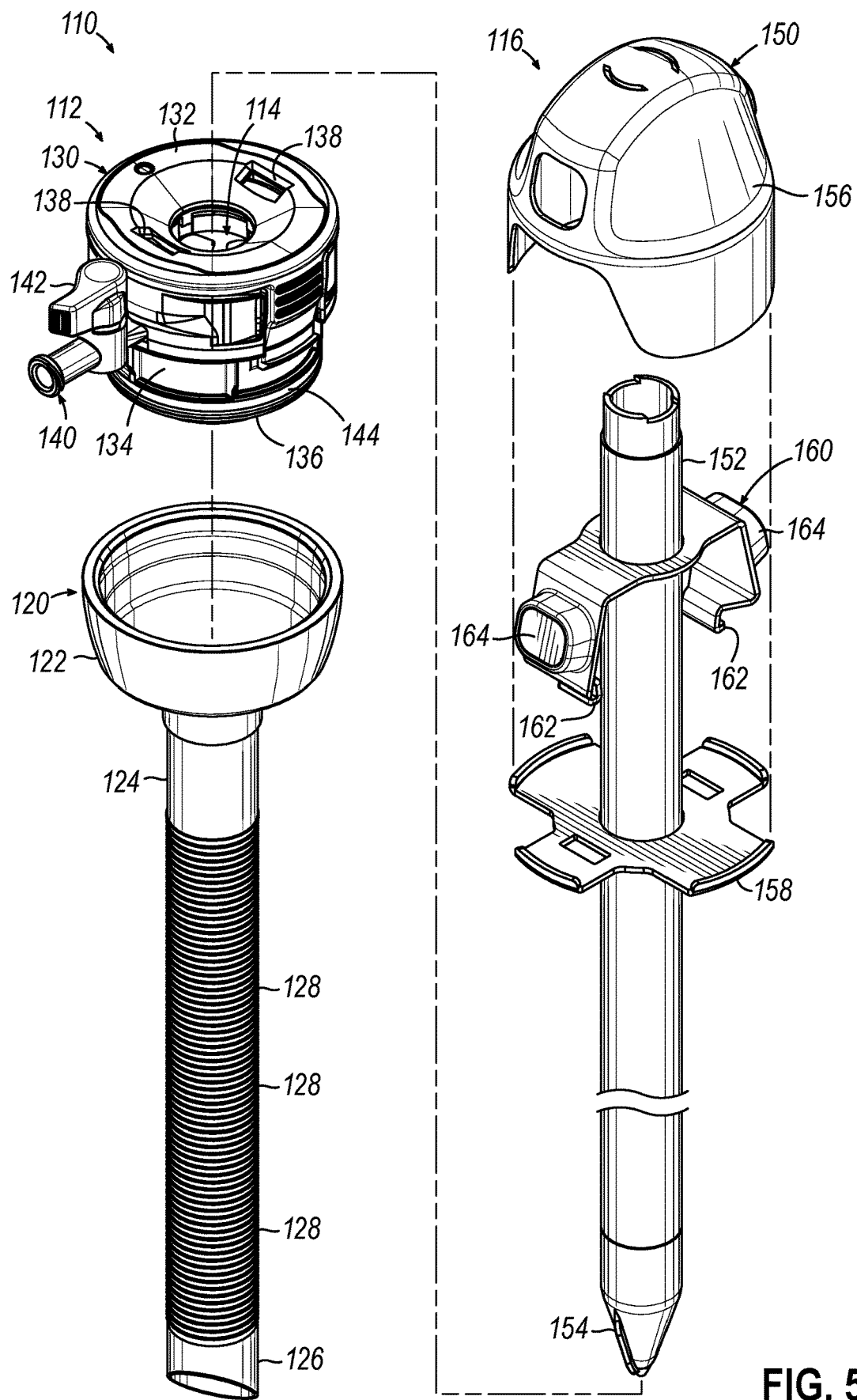
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Threaded Depth Limiters

In some instances, a clinician may desire to limit the depth to which a single-use or reusable trocar (10, 110) may travel into abdominal wall (2) (e.g., after insertion of trocar (10, 110) to a desired position). Limiting the depth to which trocar (10, 110) may travel into abdominal wall (2) may assist in preventing distal tip (64, 154) of obturator (16, 116) and/or cannula tip (24, 126) of cannula assembly (12, 112) from inadvertently entering deeper than desired into abdominal cavity (1). Preventing over insertion of trocar (10, 110) may reduce undesirable contact of distal tip (64, 154) and/or cannula tip (24, 126) with anatomical structures contained within abdominal cavity (1). Preventing over insertion of trocar (10, 110) may also avoid inadvertently reducing the available surgical working space within abdominal cavity (1).

Alternatively or in addition to limiting the depth to which single-use or reusable trocar (10, 110) may travel into abdominal wall (2), the clinician may desire to stabilize trocar (10, 110) relative to abdominal wall (2) (e.g., after insertion of trocar (10, 110) to a desired position in abdominal cavity (1)). The clinician may stabilize trocar (10, 110) relative to abdominal wall (2) by avoiding under insertion of trocar (10, 110). Stabilizing trocar (10, 110) relative to abdominal wall (2) after insertion into abdominal wall (2) may assist in preventing trocar (10, 110) from inadvertently pivoting about the insertion point in abdominal wall (2) after the clinician releases trocar (10, 110). Stabilizing trocar (10, 110) maintains cannula tip (24, 126), and thus, the entry point of surgical instruments into abdominal cavity (1) in a desired position and/or orientation relative to abdominal cavity (1) such that surgical instruments may be easily directed distally through trocar (10, 110) at a selected working angle that is convenient for the clinician.

Accordingly, it may be desirable to provide trocar (10, 110) with a device that provides the depth limiting and tilt-resisting benefits described above. Additionally, it may be desirable to provide such a device with one or more features that enable both fine positional adjustment and coarse, or rapid, positional adjustment of the device relative to trocar (10, 110).

A. Exemplary Depth Limiter with Stability Thread-Chasing Tooth

Figure 6:
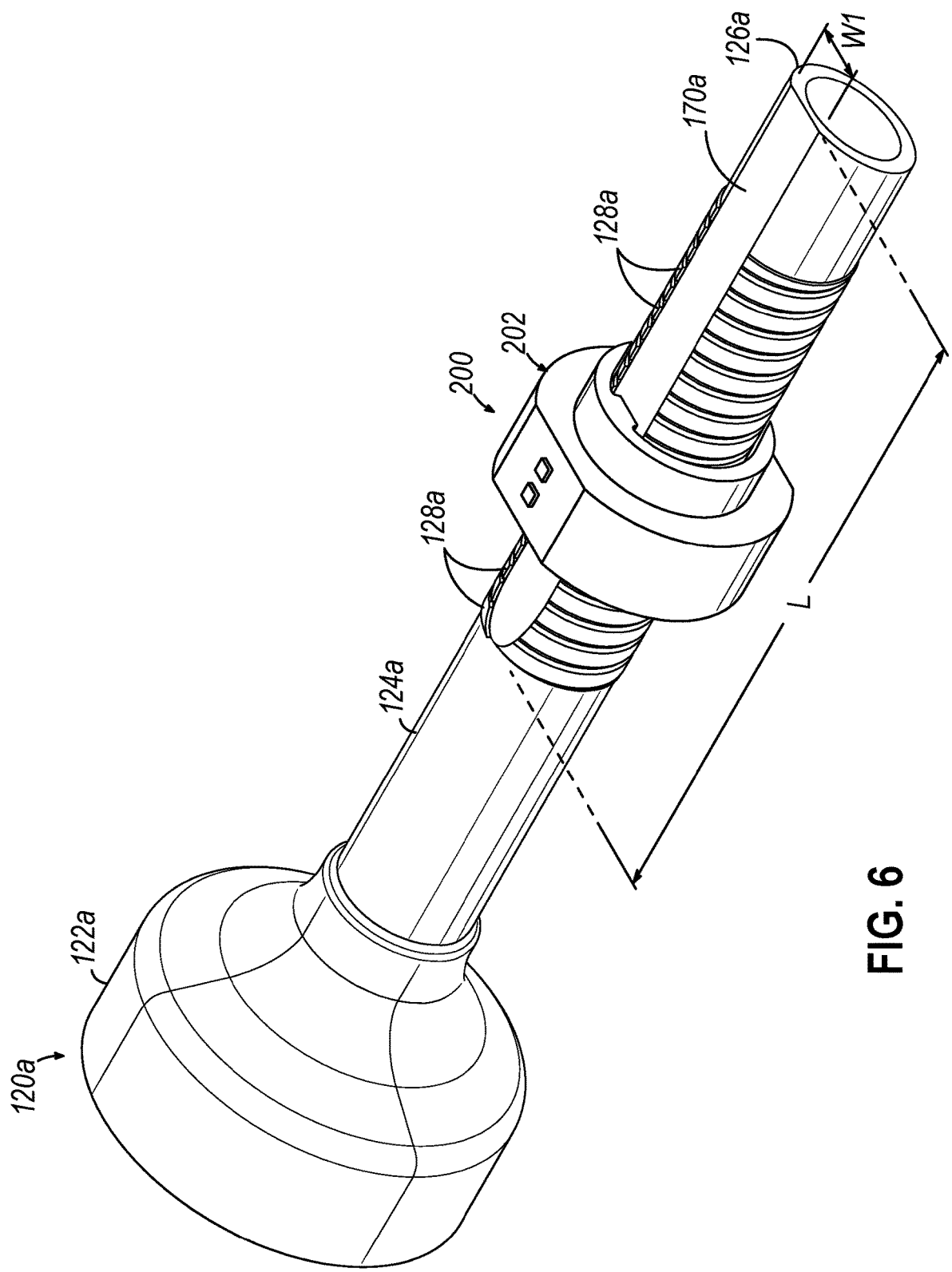
FIG. 6 depicts a perspective view of another exemplary cannula for the trocar of FIG. 4, showing an exemplary depth limiter selectively positioned about the cannula tube of the cannula.
Figure 8A:
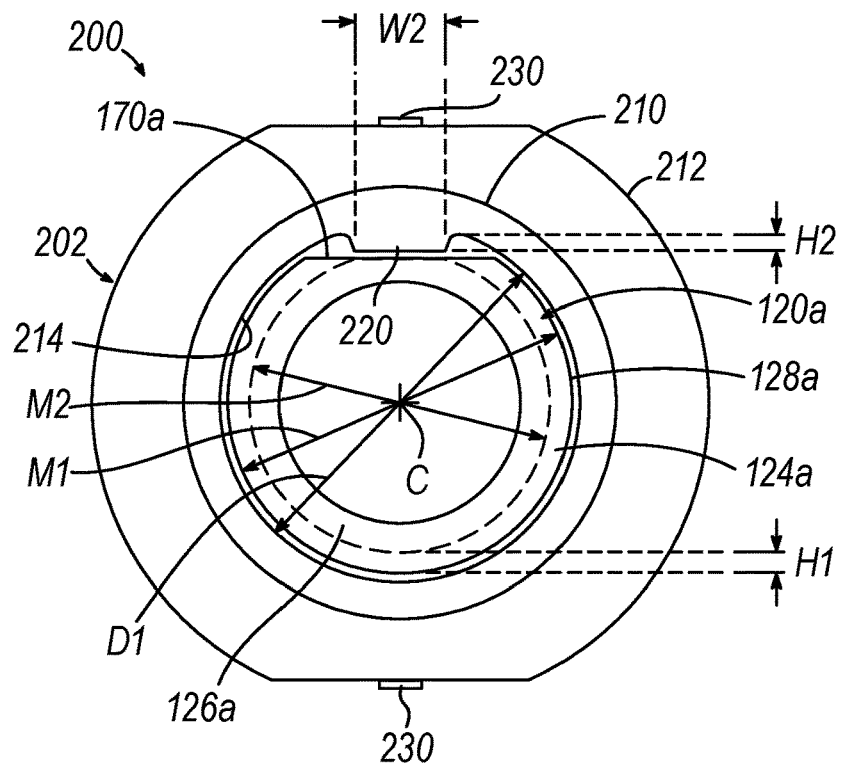
FIG. 8A depicts a bottom elevational view of the depth limiter of FIG. 6, showing a tooth of the depth limiter slidably engaged with a flat of the cannula tube such that the depth limiter is in a rapid adjustment configuration.
Figure 8B:
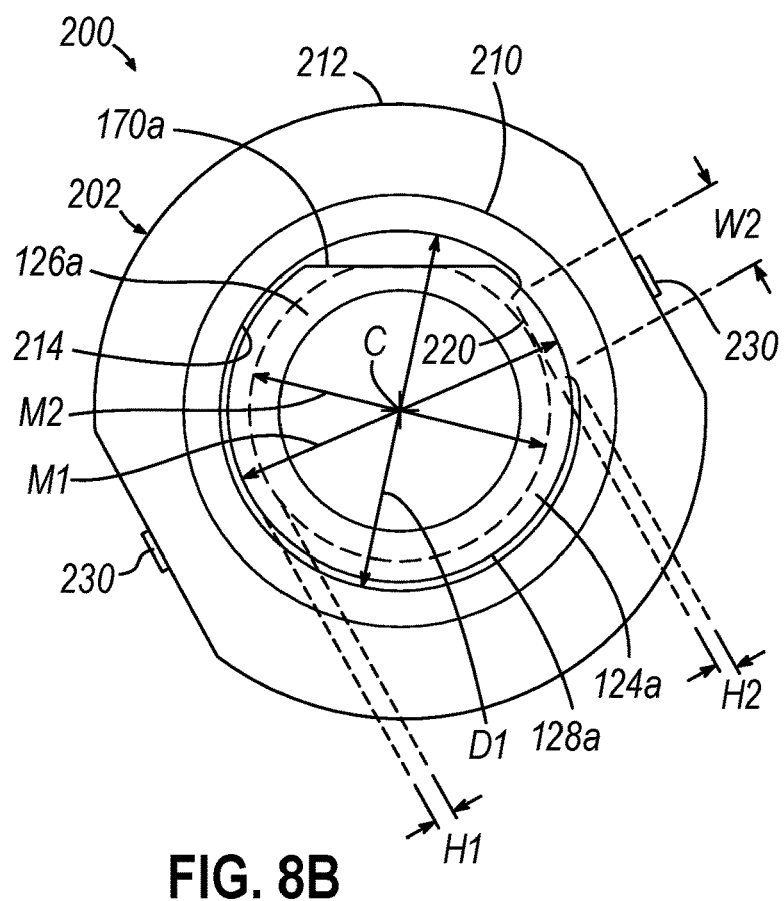
FIG. 8B depicts a bottom elevational view similar to FIG. 8A, showing the tooth of the depth limiter of FIG. 6 threadably engaged with helical stability ribs of the cannula tube such that the depth limiter is in a fine adjustment configuration.

FIG. 6 shows an alternative cannula (120a) for trocar (110) having a bell-shaped hub (122a) at a proximal end thereof, and an elongate cylindrical tube (124a) extending distally from hub (122a) and terminating at a cannula tip (126a). An outer surface of cannula tube (124a) includes a plurality of tissue gripping features in the form of helical ribs (128a) that extend around a medial portion of cannula tube (124a). Ribs (128a) are configured to grip the layers of abdominal wall tissue through which cannula (120a) is inserted, and thereby assist in stabilizing cannula (120a) in axial and radial directions while cannula (120a) is positioned within the opening formed in the abdominal wall (2) of a patient. As shown in FIGS. 8A-8B, ribs (128a) may each have a radial height (H1) defined between a radially inner root thereof and a radially outer crest thereof, and may collectively form a major external cross dimension (M1) of the medial portion of cannula tube (124a) that extends diametrically between outer crests of ribs (128a). Ribs (128a) may further collectively form a minor external cross dimension (M2) of the medial portion of cannula tube (124a) that extends diametrically between inner roots of ribs (128a), as best shown in FIGS. 8A and 8B.

In the example shown, outer surface of cannula tube (124a) also includes a track in the form of flat (170a) extending longitudinally or axially along the medial and distal portions of cannula tube (124a) such that the medial and distal portions of cannula tube (124a) have a generally D-shaped profile. More particularly, flat (170a) extends along an axial length (L) from cannula tip (126a) to a proximal-most rib (128a), and extends along a generally circumferential width (W1) between roots of each rib (128a) such that ribs (128a) are circumferentially interrupted or spaced apart from each other by width (W1) of flat (170a). Accordingly, whereas helical ribs (128a) would otherwise collectively define a single continuous helical thread about cannula tube (124a), helical ribs (128a) of the present example are discontinuous relative to one another. In one example, flat (170a) may be machined onto cannula tube (124a) after formation of a single, continuous helical rib thereon to divide such a helical rib into the illustrated plurality of ribs (128a). Cannula (120a) of the present example may be suitably constructed of a robust material, such as surgical steel, such that cannula (120a) may be sterilized and reused for multiple surgical procedures, similar to cannula (120) and obturator (116) described above.

FIG. 6 further shows a first exemplary depth limiter (200) selectively coupled to cannula tube (124a) of trocar (110). As described in greater detail below, depth limiter (200) may selectively limit the depth to which trocar (110) may travel distally into abdominal wall (2).

Figure 7:
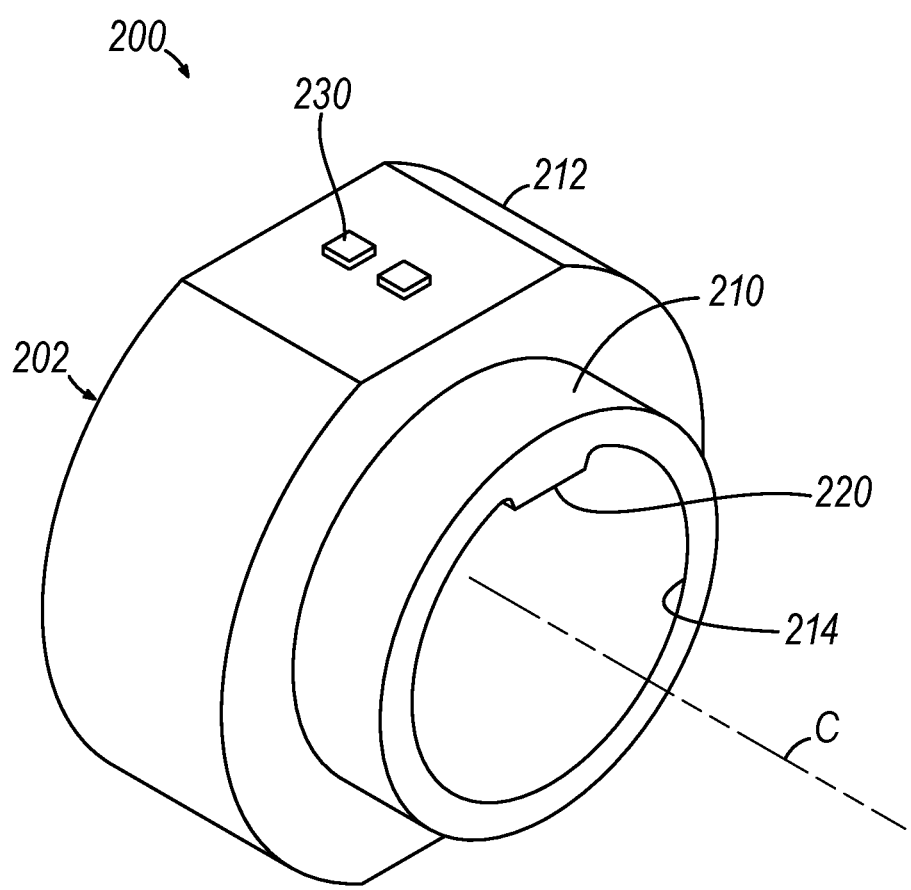
FIG. 7 depicts a perspective view of the depth limiter of FIG. 6.

As best shown in FIGS. 7-8B, depth limiter (200) includes a body portion (202) rotatable relative to cannula tube (124a) between at least one rapid (i.e., coarse) adjustment configuration (e.g., FIG. 8A) and at least one fine adjustment configuration (e.g., FIG. 8B). In one example, body portion (202) may be molded from a polymeric material, including one or more plastics. Such a construction may allow depth limiter (200) to be considered a disposable unit, intended to be separated from cannula (120a) and replaced after each procedure. For instance, such a construction may allow depth limiter (200) to be easily manufactured and sold at a price point that renders depth limiter (200) suitable for disposal after a single use, similar to trocar (10) and seal assembly (130) described above. In other versions, one or more portions of depth limiter (200) may be formed of surgical steel or other material suitable to render depth limiter sterilizable and reusable for multiple surgical procedures.

In the example shown, depth limiter (200) has a generally hollow, top hat-shaped profile. To this end, body portion (202) includes a distal cylindrical hub (210) and a proximal generally annular flange (212) extending radially outwardly therefrom. Hub (210) defines a generally cylindrical bore (214) which extends longitudinally along a central axis (C) of depth limiter (200), and includes at least one flat tooth (220) extending radially inwardly from a peripheral edge of bore (214) and configured to selectively threadably engage ribs (128a) of cannula tube (124a) and to selectively slidably engage flat (170a) of cannula tube (124a). While a single tooth (220) is shown, it will be appreciated that multiple teeth (220) may be arranged axially along bore (214) (e.g., axially spaced apart from each other by a distance corresponding to an axial spacing between ribs (128a) such that teeth (220) may be capable of simultaneously threadably engaging ribs (128a)) and/or circumferentially thereabout, as described below. The illustrated flange (212) includes a pair of diametrically opposed finger grips (230) configured to provide a visual and/or tactile indication to a user of the locations on body portion (202) to be gripped for effectively and ergonomically manipulating body portion (202), such as for rotating body portion (202) between the rapid adjustment and fine adjustment configurations, as described in greater detail below.

In this regard, and as best shown in FIGS. 8A and 8B, bore (214) may have an internal cross dimension (D1) that extends diametrically through central axis (C) and is substantially equal to or slightly greater than major external cross dimension (M1) of the medial portion of cannula tube (124a), such that bore (214) may be sized to movably receive at least the medial portion of cannula tube (124a).

Tooth (220) may have a radial height (H2) that is defined between an inner root thereof and an outer crest thereof and is substantially equal to or slightly less than height (H1) of ribs (128a), such that tooth (220) may be sized to extend radially inwardly relative to crests of ribs (128a) and radially outwardly relative to roots of ribs (128a).

Tooth (220) may also have an axial thickness (not shown) that is defined between proximal and distal ends thereof and is substantially equal to or slightly less than an axial spacing between adjacent ribs (128a), such that tooth (220) may be sized to be received therebetween.

Tooth (220) may further have a generally circumferential width (W2) that is defined between lateral edges thereof and is substantially equal to or less than width (W1) of flat (170a), such that tooth (220) may be sized to radially or angularly align with flat (170a) outside of ribs (128a). In this manner, tooth (220) may be configured to selectively mate with or threadably engage ribs (128a) to convert rotation of depth limiter (200) relative to cannula tube (124a) into relatively fine axial adjustment of depth limiter (200) relative to cannula tube (124a), and may be further configured to selectively slidably engage flat (170a) to permit relatively coarse or rapid axial adjustment of depth limiter (200) relative to cannula tube (124a).

More particularly, and as shown in FIG. 8A, when depth limiter (200) is in the rapid adjustment configuration, tooth (220) may be radially aligned with and generally parallel to flat (170a) and may be radially misaligned from ribs (128a) such that tooth (220) is slidably engaged with flat (170a) and threadably disengaged from ribs (128a). The interaction between tooth (220) and flat (170a) may be configured to allow for rapid axial movement of depth limiter (200) relative to cannula tube (124a), such as by allowing depth limiter (200) to be translatable relative to cannula tube (124a).

As shown in FIG. 8B, when depth limiter (200) is in the fine adjustment configuration, tooth (220) may be at least partially radially aligned with ribs (128a) and at least partially radially misaligned from flat (170a) such that tooth (220) is threadably engaged with ribs (128a) and slidably disengaged from flat (170a). The interaction between tooth (220) and ribs (128a) may be configured to restrict axial movement of depth limiter (200) relative to cannula tube (124a) and/or allow for fine axial movement of depth limiter (200) relative to cannula tube (124a), such as by constraining depth limiter (200) to rotatable, helical movement relative to cannula tube (124a).

Finger grips (230) may be configured to provide a visual and/or tactile indication to a user of the locations on body portion (202) to be gripped for effectively and ergonomically translating depth limiter (200) relative to cannula tube (124a) while in the rapid adjustment configuration and/or moving depth limiter (200) helically relative to cannula tube (124a) while in the fine adjustment configuration, in addition to providing a visual and/or tactile indication to a user of the locations on body portion (202) to be gripped for effectively and ergonomically rotating body portion (202) between the rapid adjustment and fine adjustment configurations.

During operation, and with continuing reference to FIGS. 8A and 8B, depth limiter (200) may be initially positioned about cannula tube (124a) of trocar (110) such that cannula tube (124a) is received within bore (214) prior to deployment of trocar (110) into the patient's abdominal cavity (1). During deployment of trocar (110) into abdominal cavity (1), body portion (202) may be in either the rapid adjustment configuration or the fine adjustment configuration, as may be desired.

In some cases, the clinician may desire to allow rapid axial movement of depth limiter (200) relative to cannula tube (124a) of trocar (110) during deployment. Thus, the clinician may choose to maintain body portion (202) in the rapid adjustment configuration. By maintaining body portion (202) in the rapid adjustment configuration, tooth (220) may be unconstrained by ribs (128a). More particularly, tooth (220) may be radially aligned with flat (170a) to allow translation of depth limiter (200) relative to cannula tube (124a) of trocar (110), as shown in FIG. 8A.

In other cases, the clinician may desire to restrict axial movement of depth limiter (200) relative to cannula tube (124a) of trocar (110) during deployment. For example, the clinician may desire to position depth limiter (200) at a predetermined axial location along cannula tube (124a) corresponding to a desired depth of insertion of cannula (120a) within cavity (1). Thus, the clinician may choose to rotate body portion (202) relative to cannula tube (124a) from the rapid adjustment configuration toward the fine adjustment configuration. To this end, the clinician may manipulate depth limiter (200), such as via finger grips (230), to effectively and ergonomically rotate body portion (202) toward the fine adjustment configuration. By rotating body portion (202) toward the fine adjustment configuration, tooth (220) may be constrained to helical movement by ribs (128a). More particularly, tooth (220) may be at least partially radially aligned with ribs (128a) to allow substantially only helical movement of depth limiter (200) relative to cannula tube (124a), as shown in FIG. 8B. Once depth limiter (200) is at the predetermined axial location, the clinician may release depth limiter (200) while still in the fine adjustment configuration, thereby allowing the threadable engagement between tooth (220) and ribs (128a) to maintain depth limiter (200) at the predetermined axial location.

With depth limiter (200) positioned about cannula tube (124a) in either an axially restricted or unrestricted state, the clinician may deploy trocar (110) into the patient's abdominal cavity (1) as described above with respect to FIGS. 3A and 3B to position cannula (120a) at a desired depth of insertion in cavity (1). In cases where depth limiter (200) is secured to cannula tube (124a) during deployment at a predetermined axial location along cannula tube (124a) corresponding to a desired depth of insertion of cannula (120a) within cavity (1), contact between distal hub (210) of depth limiter (200) and abdominal wall (2) may provide a visual and/or tactile indication to the clinician that cannula (120a) has reached the desired depth of insertion in cavity (1). In this manner, depth limiter (200) may assist in preventing distal tip (154) of obturator (116) and/or cannula tip (126a) of cannula assembly (112) from inadvertently entering deeper than desired into abdominal cavity (1) during deployment. In other cases, depth limiter (200) may be secured to cannula tube (124a) after cannula (120a) is positioned at a desired depth of insertion in cavity (1).

In some cases, it may be desirable to rapidly adjust the axial location of depth limiter (200) along cannula tube (124a) after depth limiter (200) has already been secured to cannula tube (124a). Thus, the clinician may selectively manipulate depth limiter (200) to rotate body portion (202) relative to cannula tube (124a) from the fine adjustment configuration toward the rapid adjustment configuration and may subsequently translate body portion (202) relative to cannula tube (124a) to a new axial location. Once depth limiter (200) is at the new axial location, the clinician may selectively manipulate depth limiter (200) to rotate body portion (202) relative to cannula tube (124a) from the rapid adjustment configuration to the fine adjustment configuration and subsequently release depth limiter (200) while in the fine adjustment configuration, thereby allowing the threadable engagement between tooth (220) and ribs (128a) to maintain depth limiter (200) at the new axial location.

Likewise, it may be desirable to finely adjust the axial location of depth limiter (200) along cannula tube (124a) after depth limiter (200) has already been secured to cannula tube (124a). Thus, with depth limiter (200) in the fine adjustment configuration, the clinician may helically move body portion (202) relative to cannula tube (124a) to fine-tune the axial location of depth limiter (200) relative to cannula tube (124a). During such movement, the clinician may carefully continue to move body portion (202) along the desired helical path as tooth (220) orbits about flat (170a) (e.g., such that depth limiter (200) is briefly placed in the rapid adjustment configuration) to prevent tooth (220) from inadvertently sliding axially along flat (170a) or "skipping" ribs (128a) and thereby prevent depth limiter (200) from suddenly translating relative to cannula tube (124a). Once depth limiter (200) is at the fine-tuned axial location, the clinician may release depth limiter (200) while in the fine adjustment configuration, thereby allowing the threadable engagement between tooth (220) and ribs (128a) to maintain depth limiter (200) at the fine-tuned axial location.

Thus, the clinician may adjust the axial location of depth limiter (200) along cannula tube (124a), and may subsequently re-secure depth limiter (200) to cannula tube (124a) by simply releasing depth limiter (200) while in the fine adjustment configuration.

Depth limiter (200) may remain securely coupled to cannula tube (124a) during performance of the laparoscopic surgical procedure with distal hub (210) of depth limiter (200) resting against abdominal wall (2). In this manner, depth limiter (200) may assist in preventing cannula tip (126a) of cannula assembly (112) from inadvertently entering deeper than desired into abdominal cavity (1) during performance of the laparoscopic surgical procedure.

Upon completion of the laparoscopic surgical procedure, depth limiter (200) may be withdrawn proximally from abdominal wall (2) together with cannula assembly (112). Depth limiter (200) may be rapidly removed from cannula tube (124a) by rotating body portion (202) relative to cannula tube (124a) toward the rapid adjustment configuration as described above and subsequently translating depth limiter (200) distally relative to cannula tube (124a). In one example, depth limiter (200) may be simply disposed of after completion of a single laparoscopic surgical procedure.

B. Exemplary Two-Piece Depth Limiter with Stability Thread Chasing Teeth

In some instances, it may be desirable to provide a cannula depth limiter with a clocking mechanism to prevent inadvertent transitions from the fine adjustment configuration to the rapid adjustment configuration.

Figure 9A:
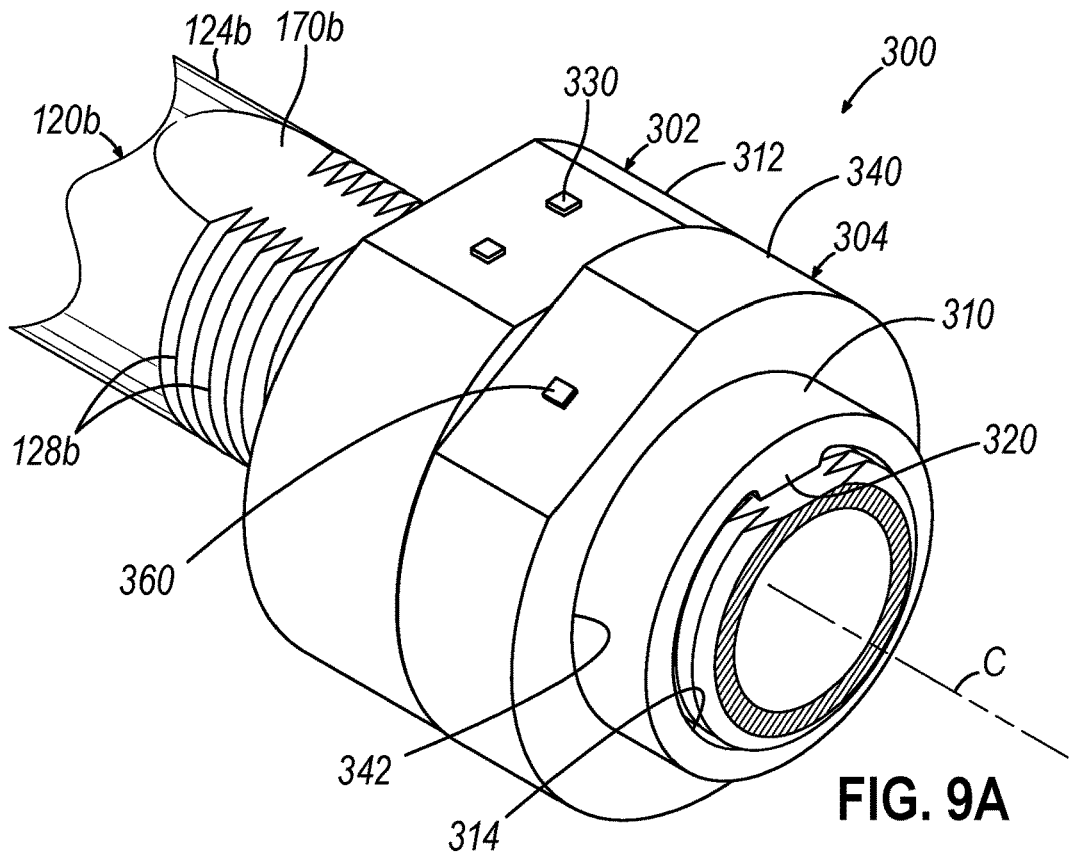
FIG. 9A depicts a perspective view of another exemplary depth limiter selectively positioned about another exemplary cannula tube for the trocar of FIG. 4, showing first and second body portions of the depth limiter in an unclocked configuration wherein at least one tooth of the first or second body portions is threadably engaged with helical stability ribs of the cannula tube such that the depth limiter is in a fine adjustment configuration.
Figure 9B:
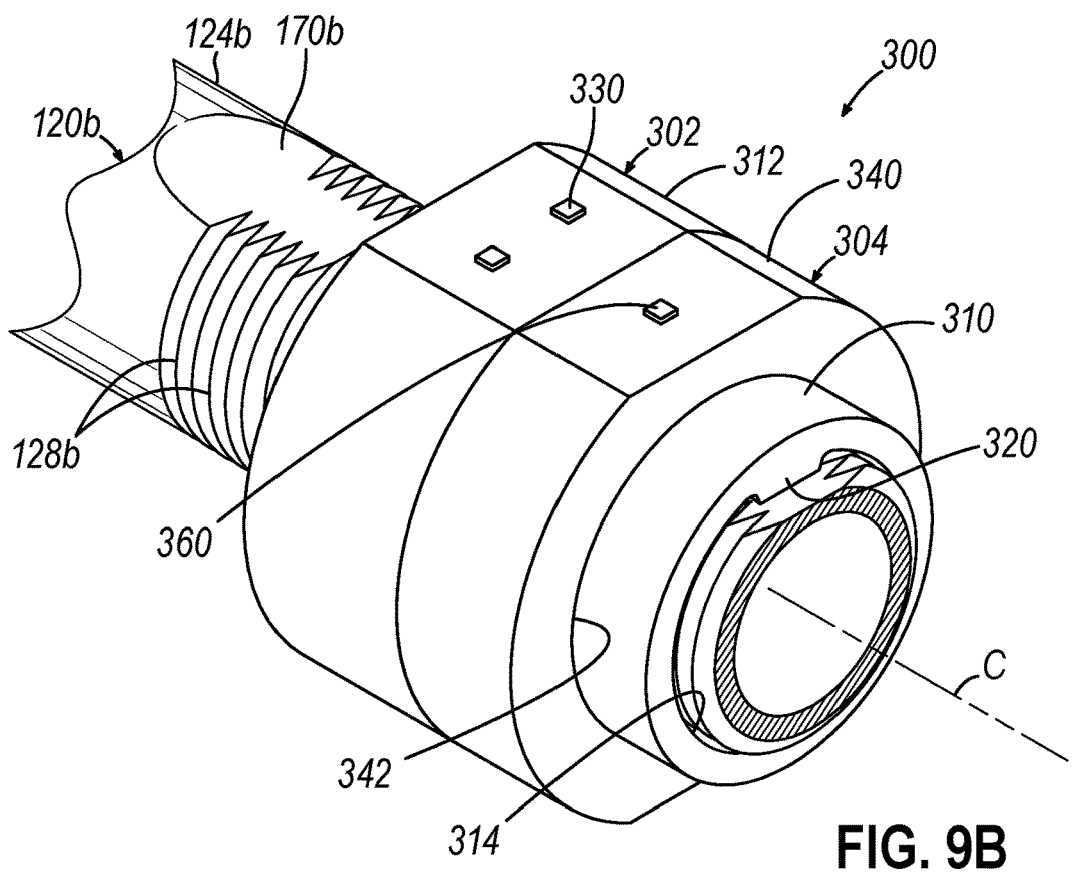
FIG. 9B depicts a perspective view similar to FIG. 9A, showing the first and second body portions of the depth limiter of FIG. 9A in a clocked configuration wherein the teeth of the first and second body portions are both slidably engaged with the flat of the cannula tube such that the depth limiter is in a rapid adjustment configuration.
Figure 10A:
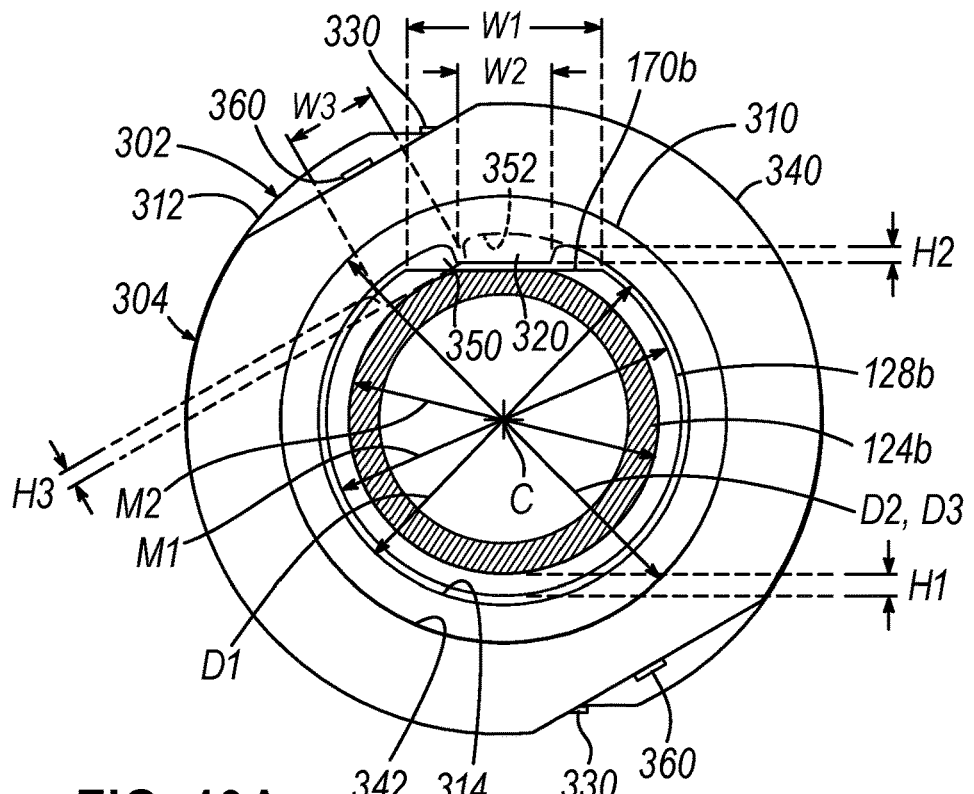
FIG. 10A depicts a bottom elevational view of the depth limiter of FIG. 9A selectively positioned about the cannula tube, showing the first and second body portions of the depth limiter of FIG. 9A in the unclocked configuration such that the depth limiter is in the fine adjustment configuration.
Figure 10B:
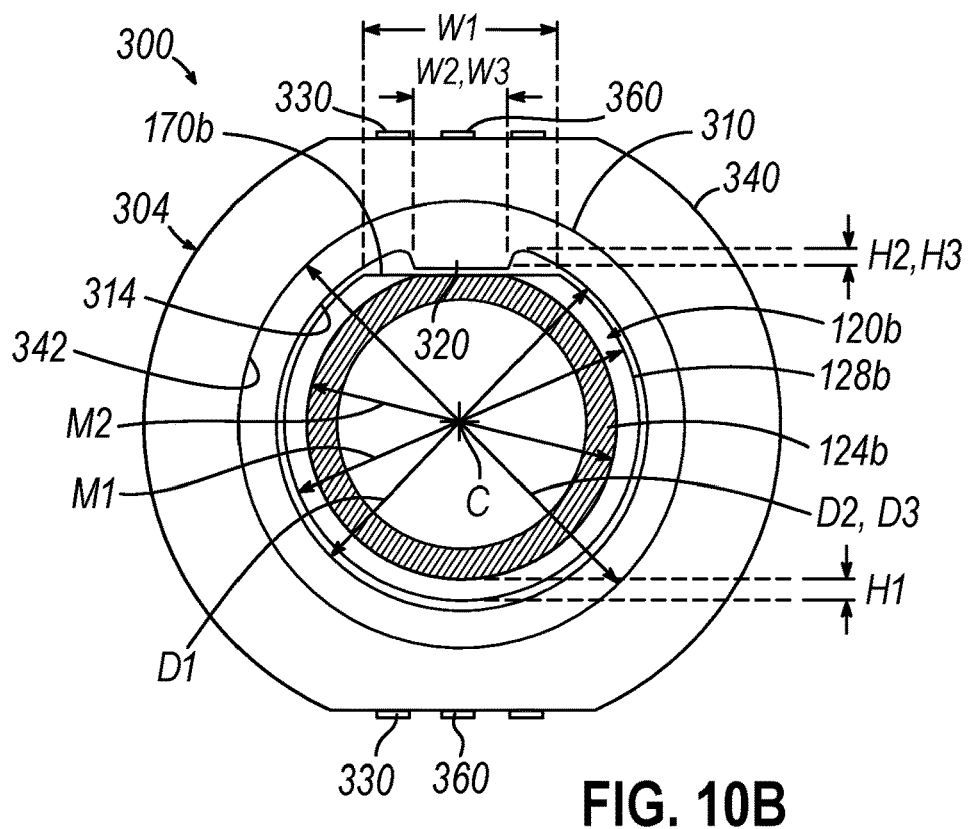
FIG. 10B depicts a bottom elevational view similar to FIG. 10A, showing the first and second body portions of the depth limiter of FIG. 9A in the clocked configuration and further showing the depth limiter in the rapid adjustment configuration.

FIGS. 9A-10B show another alternative cannula (120b) for trocar (110) having an elongate cylindrical tube (124b) extending distally from a hub (not shown) and terminating at a cannula tip (not shown). An outer surface of cannula tube (124b) includes a plurality of tissue gripping features in the form of helical ribs (128b) that extend around a medial portion of cannula tube (124b). Ribs (128b) are configured to grip the layers of abdominal wall tissue through which cannula (120b) is inserted, and thereby assist in stabilizing cannula (120b) in axial and radial directions while cannula (120b) is positioned within the opening formed in the abdominal wall (2) of a patient. Ribs (128b) may each have a radial height (H1) defined between an inner root thereof and an outer crest thereof, and may collectively form a major external cross dimension (M1) of the medial portion of cannula tube (124b) that extends diametrically between outer crests of ribs (128b), and may further collectively form a minor external cross dimension (M2) of the medial portion of cannula tube (124b) that extends diametrically between inner roots of ribs (128b), as best shown in FIGS. 10A and 10B.

In the example shown, outer surface of cannula tube (124b) also includes a track in the form of flat (170b) extending longitudinally or axially along at least the medial portion of cannula tube (124b) such that at least the medial portion of cannula tube (124b) has a generally D-shaped profile. More particularly, flat (170b) extends along an axial length from cannula tip to a proximal-most rib (128b), and extends along a generally circumferential width (W1) between roots of each rib (128b) such that ribs (128b) are circumferentially interrupted or spaced apart from each other by width (W1) of flat (170b). In one example, flat (170b) may be machined onto cannula tube (124b) after formation of a single, continuous helical rib thereon to divide such a helical rib into the illustrated plurality of ribs (128b). Cannula (120b) of the present example may be suitably constructed of a robust material, such as surgical steel, such that cannula (120b) may be sterilized and reused for multiple surgical procedures, similar to cannula (120b) and obturator (116) described above.

FIGS. 9A-10B further show a second exemplary depth limiter (300) selectively coupled to cannula tube (124b) of trocar (110). Similar to depth limiter (200), depth limiter (300) may selectively limit the depth to which trocar (110) may travel distally into abdominal wall (2).

As shown, depth limiter (300) includes first and second body portions (302, 304) rotatable relative to cannula tube (124a) between at least one rapid adjustment configuration (e.g., FIGS. 9B and 10B) and at least one fine adjustment configuration (e.g., FIGS. 9A and 10A), and further rotatable relative to each other between a radially aligned or "clocked" configuration (e.g., FIGS. 9B and 10B) and at least one radially misaligned or "unclocked" configuration (e.g., FIGS. 9A and 10A). In one example, first and second body portions (302, 304) may each be molded from a polymeric material, including one or more plastics. Such a construction may allow depth limiter (300) to be considered a disposable unit, intended to be separated from cannula (120b) and replaced after each procedure. For instance, such a construction may allow depth limiter (300) to be easily manufactured and sold at a price point that renders depth limiter (300) suitable for disposal after a single use, similar to trocar (10) and seal assembly (130) described above. In other versions, one or more portions of depth limiter (300) may be formed of surgical steel or other material suitable to render depth limiter sterilizable and reusable for multiple surgical procedures.

In the example shown, depth limiter (300) has a generally hollow, top hat-shaped profile. To this end, first body portion (302) includes a distal cylindrical hub (310) and a proximal generally annular flange (312) extending radially outwardly therefrom. Hub (310) defines a generally cylindrical bore (314) which extends longitudinally along a central axis (C) of depth limiter (300), and includes at least one first flat tooth (320) extending radially inwardly from a peripheral edge of bore (314) and configured to selectively threadably engage ribs (128b) of cannula tube (124b) and to selectively slidably engage flat (170b) of cannula tube (124b). While a single first tooth (320) is shown, it will be appreciated that multiple first teeth (320) may be arranged axially along bore (314) (e.g., axially spaced apart from each other by a distance corresponding to an axial spacing between ribs (128b) such that first teeth (320) may be capable of simultaneously threadably engaging ribs (128b)) and/or circumferentially thereabout, as described below. The illustrated flange (312) includes a pair of diametrically opposed finger grips (330) configured to provide a visual and/or tactile indication to a user of the locations on first body portion (302) to be gripped for effectively and ergonomically manipulating first body portion (302), such as for rotating first body portion (302) between the rapid adjustment and fine adjustment configurations, as described in greater detail below.

Similarly, second body portion (304) includes a generally annular collar (340) defining a generally cylindrical bore (342) which extends longitudinally along central axis (C) of depth limiter (300). As best shown in FIG. 10A, collar (340) includes at least one second flat tooth (350) extending radially inwardly from a semi-annular ledge (352), which extends radially inwardly from a peripheral edge of bore (342), and configured to selectively threadably engage ribs (128b) of cannula tube (124b) and to selectively slidably engage flat (170b) of cannula tube (124b). While a single second tooth (350) is shown, it will be appreciated that multiple second teeth (350) may be arranged axially along bore (342) (e.g., axially spaced apart from each other by a distance corresponding to an axial spacing between ribs (128b) such that second teeth (350) may be capable of simultaneously threadably engaging ribs (128b)) and/or circumferentially thereabout, as described below. The illustrated collar (340) also includes a pair of diametrically opposed finger grips (360) configured to provide a visual and/or tactile indication to a user of the locations on second body portion (304) to be gripped for effectively and ergonomically manipulating second body portion (304), such as for rotating second body portion (304) between the rapid adjustment and fine adjustment configurations, as described in greater detail below.

In this regard, and as best shown in FIGS. 10A and 10B, bore (314) of first body portion (302) may have an internal cross dimension (D1) that extends diametrically through central axis (C) and is substantially equal to or slightly greater than major external cross dimension (M1) of the medial portion of cannula tube (124b), such that bore (314) may be sized to movably receive at least the medial portion of cannula tube (124b).

First tooth (320) may have a radial height (H2) that is defined between an inner root thereof and an outer crest thereof and is substantially equal to or slightly less than height (H1) of ribs (128b), such that first tooth (320) may be sized to extend radially inwardly relative to crests of ribs (128b) and radially outwardly relative to roots of ribs (128b).

First tooth (320) may also have an axial thickness (not shown) that is defined between proximal and distal ends thereof and is substantially equal to or slightly less than an axial spacing between adjacent ribs (128b), such that first tooth (320) may be sized to be received therebetween.

First tooth (320) may further have a generally circumferential width (W2) that is defined between lateral edges thereof and is substantially equal to or less than width (W1) of flat (170b), such that first tooth (320) may be sized to radially or angularly align with flat (170b) outside of ribs (128b). In this manner, first tooth (320) may be configured to selectively mate with or threadably engage ribs (128b) to convert rotation of depth limiter (300) relative to cannula tube (124b) into relatively fine axial adjustment of depth limiter (300) relative to cannula tube (124b), and may be further configured to selectively slidably engage flat (170b) to permit relatively coarse or rapid axial adjustment of depth limiter (200) relative to cannula tube (124a).

With continuing reference to FIGS. 10A and 10B, bore (342) of second body portion (304) may have an internal cross dimension (D2) that extends diametrically through central axis (C) and is substantially equal to or slightly greater than an external cross dimension (D3) of hub (310), such that bore (342) may be sized to rotatably receive hub (310). In one example, first body portion (302) may include a slot (not shown) extending radially through hub (310) from bore (314) to an outer surface thereof and at least partially circumferentially thereabout. Such a slot may be configured to rotatably receive ledge (352) and/or second tooth (350) of second body portion (304) such that second tooth (350) is permitted to extend radially inwardly into bore (314) and to rotate relative to first tooth (320), as described in greater detail below.

Second tooth (350) may have a radial height (H3) that is defined between an inner root thereof and an outer crest thereof and is substantially equal to or slightly less than height (H1) of ribs (128b), such that second tooth (350) may be sized to extend radially inwardly relative to crests of ribs (128b) and radially outwardly relative to roots of ribs (128b). For example, height (H3) of second tooth (350) may be substantially equal to height (H2) of first tooth (320) such that first and second teeth (320, 350) may be radially coextensive when radially aligned with each other.

Second tooth (350) may also have an axial thickness (not shown) that is defined between proximal and distal ends thereof and is substantially equal to or slightly less than an axial spacing between adjacent ribs (128b), such that second tooth (350) may be sized to be received therebetween. For example, a thickness of second tooth (350) may be substantially equal to a thickness of first tooth (320).

Second tooth (350) may further have a generally circumferential width (W3) that is defined between lateral edges thereof and is substantially equal to or less than width (W1) of flat (170b), such that second tooth (350) may be sized to radially or angularly align with flat (170b) outside of ribs (128b). For example, width (W3) of second tooth (350) may be substantially equal to width (W2) of first tooth (320) such that first and second teeth (320, 350) may be circumferentially coextensive when radially aligned with each other. In this manner, similar to first tooth (320), second tooth (350) may be configured to selectively mate with or threadably engage ribs (128b) to convert rotation of depth limiter (300) relative to cannula tube (124b) into relatively fine axial adjustment of depth limiter (300) relative to cannula tube (124b), and may be further configured to selectively slidably engage flat (170b) to permit relatively coarse or rapid axial adjustment of depth limiter (200) relative to cannula tube (124a). In one example, teeth (320, 350) may be axially spaced apart from each other by a distance corresponding to an axial spacing between ribs (128b) such that teeth (320, 350) may be capable of simultaneously threadably engaging ribs (128b).

More particularly, and as shown in FIG. 10A, when depth limiter (300) is in the fine adjustment configuration, at least one of first or second teeth (320, 350) may be at least partially radially aligned with ribs (128b) and at least partially radially misaligned from flat (170b) such that at least one tooth (320, 350) is threadably engaged with ribs (128b) and slidably disengaged from flat (170b). To this end, first and second body portions (302, 304) may be in an unlocked configuration such that teeth (320, 350) are radially misaligned from each other, thereby allowing at least one tooth (350) to be threadably engaged with ribs (128b) while the other tooth (320) may be threadably disengaged from ribs (128b). The interaction between the at least one tooth (320, 350) and ribs (128b) may be configured to restrict axial movement of depth limiter (300) relative to cannula tube (124b) and/or allow for fine axial movement of depth limiter (300) relative to cannula tube (124b), such as by constraining depth limiter (300) to helical movement relative to cannula tube (124b).

As shown in FIG. 10B, when depth limiter (300) is in the rapid adjustment configuration, both teeth (320, 350) may be radially aligned with and generally parallel to flat (170b) and may be radially misaligned from ribs (128b) such that both teeth (320, 350) are slidably engaged with flat (170b) and threadably disengaged from ribs (128b). To this end, first and second body portions (302, 304) may be in the clocked configuration with teeth (320, 350) radially aligned with each other, thereby allowing both teeth (320, 350) to be slidably engaged with flat (170b). The interaction between both teeth (320, 350) and flat (170b) may be configured to allow for rapid axial movement of depth limiter (300) relative to cannula tube (124b), such as by allowing depth limiter (300) to be translatable relative to cannula tube (124b).

In one example, widths (W2, W3) of teeth (320, 350) may be sized relative to each other and relative to width (W1) of flat (170b) such that at least one tooth (320, 350) is configured to be threadably engaged with ribs (128b) and slidably disengaged from flat (170b) when first and second body portions (302, 304) are in the at least one unclocked configuration with teeth (320, 350) radially misaligned from each other. For example, widths (W2, W3) of teeth (320, 350) may be sized such that teeth (320, 350) collectively occupy a circumferential envelope having an effective or cumulative width greater than width (W1) of flat (170b) when teeth (320, 350) are radially misaligned from each other. In this manner, placement of first and second body portions (302, 304) in the unclocked configuration may correspond to placement of depth limiter (300) in the fine adjustment configuration. In other words, depth limiter (300) may be inhibited from being placed in the rapid adjustment configuration while first and second body portions (302, 304) are in the unclocked configuration. Thus, placement of first and second body portions (302, 304) in the unclocked configuration may inhibit inadvertent transitions of depth limiter (300) from the fine adjustment configuration to the rapid adjustment configuration, thereby inhibiting depth limiter (300) from suddenly translating relative to cannula tube (124b) during helical movement of depth limiter (300) relative to cannula tube (124b), such as by preventing teeth (320, 350) from inadvertently sliding axially along flat (170b) while orbiting thereabout between ribs (128b), or "skipping" ribs (128b).

Widths (W2, W3) of teeth (320, 350) may also be sized relative to each other and relative to width (W1) of flat (170b) such that both teeth (320, 350) are configured to slidably engaged with flat (170b) when first and second body portions (302, 304) are in the clocked configuration with teeth (320, 350) radially aligned with each other. For example, widths (W2, W3) of teeth (320, 350) may be equal to each other as described above. Likewise, heights (H2, H3) of teeth (320, 350) may be equal to each other as described above, such that teeth (320, 350) may axially overlie each other and thereby occupy a circumferential envelope having a width no greater than one or both of widths (W2, W3) of teeth (320, 350) and thus less than width (W1) of flat (170b) when teeth (320, 350) are radially aligned with each other. In this manner, placement of first and second body portions (302, 304) in the clocked configuration may permit placement of depth limiter (300) in the rapid adjustment configuration.

In one example, first and second body portions (302, 304) may be biased relative to each other toward the unclocked configuration such that teeth (320, 350) are naturally radially misaligned from each other. In this regard, depth limiter (300) may include a resilient biasing member such as a torsion spring (not shown) positioned between first and second body portions (302, 304) and configured to bias first and second body portions (302, 304) toward the unclocked configuration. Alternatively, first and second body portions (302, 304) may include camming surfaces (not shown) configured to bias first and second body portions (302, 304) toward the unclocked configuration. In any event, such biasing of first and second portions (302, 304) may assist in inhibiting inadvertent transitions of depth limiter (300) from the fine adjustment configuration to the rapid adjustment configuration by effectively biasing depth limiter (300) toward the fine adjustment configuration.

Finger grips (330, 360) may be configured to provide a visual and/or tactile indication to a user of the locations on body portions (302, 304) to be gripped for effectively and ergonomically translating depth limiter (300) relative to cannula tube (124b) while in the rapid adjustment configuration and/or moving depth limiter (300) helically relative to cannula tube (124b) while in the fine adjustment configuration, in addition to providing a visual and/or tactile indication to a user of the locations on body portions (302, 304) to be gripped for effectively and ergonomically rotating body portions (302, 304) relative to each other between the clocked and unclocked configurations and/or collectively between the rapid adjustment and fine adjustment configurations.

During operation, and with continuing reference to FIGS. 10A and 10B, depth limiter (300) may be initially positioned about cannula tube (124b) of trocar (110) such that cannula tube (124b) is received within bore (314) prior to deployment of trocar (110) into the patient's abdominal cavity (1). During deployment of trocar (110) into abdominal cavity (1), body portions (302, 304) may be in either the rapid adjustment configuration or the fine adjustment configuration and/or in either the clocked configuration or the unclocked configuration, as may be desired.

In some cases, the clinician may desire to allow rapid axial movement of depth limiter (300) relative to cannula tube (124b) of trocar (110) during deployment. Thus, the clinician may choose to maintain body portions (302, 304) in both the clocked configuration and the rapid adjustment configuration. By maintaining body portions (302, 304) in both the clocked configuration and the rapid adjustment configuration, both teeth (320, 350) may be unconstrained by ribs (128b). More particularly, both teeth (320, 350) may be radially aligned with flat (170b) to allow translation of depth limiter (300) relative to cannula tube (124b) of trocar (110), as shown in FIG. 10B.

In other cases, the clinician may desire to restrict axial movement of depth limiter (300) relative to cannula tube (124b) of trocar (110) during deployment. For example, the clinician may desire to position depth limiter (300) at a predetermined axial location along cannula tube (124b) corresponding to a desired depth of insertion of cannula (120b) within cavity (1). Thus, the clinician may choose to rotate at least one body portion (302, 304) relative to cannula tube (124b) from the rapid adjustment configuration toward the fine adjustment configuration. To this end, the clinician may manipulate depth limiter (300), such as via finger grips (330, 360), to effectively and ergonomically rotate at least one body portion (302, 304) toward the fine adjustment configuration. In one example, such manipulation may include rotating the body portions (302, 304) relative to each other to the unclocked configuration. By rotating at least one body portion (302, 304) toward the fine adjustment configuration, at least one tooth (320, 350) may be constrained to helical movement by ribs (128b). More particularly, at least one tooth (320, 350) may be at least partially radially aligned with ribs (128b) to allow substantially only helical movement of depth limiter (300) relative to cannula tube (124b), as shown in FIG. 10A. Once depth limiter (300) is at the predetermined axial location, the clinician may release depth limiter (300) while still in the fine adjustment configuration, thereby allowing the threadable engagement between at least one tooth (320, 350) and ribs (128b) to maintain depth limiter (300) at the predetermined axial location. In one example, a biasing of first and second body portions (302, 304) toward the unclocked configuration may assist in maintaining depth limiter (300) in the fine adjustment configuration when released by the clinician.

With depth limiter (300) positioned about cannula tube (124b) in either an axially restricted or unrestricted state, the clinician may deploy trocar (110) into the patient's abdominal cavity (1) as described above with respect to FIGS. 3A and 3B to position cannula (120b) at a desired depth of insertion in cavity (1). In cases where depth limiter (300) is secured to cannula tube (124b) during deployment at a predetermined axial location along cannula tube (124b) corresponding to a desired depth of insertion of cannula (120b) within cavity (1), contact between distal hub (310) of depth limiter (300) and abdominal wall (2) may provide a visual and/or tactile indication to the clinician that cannula (120b) has reached the desired depth of insertion in cavity (1). In this manner, depth limiter (300) may assist in preventing distal tip (154) of obturator (116) and/or cannula tip (not shown) of cannula assembly (112) from inadvertently entering deeper than desired into abdominal cavity (1) during deployment. In other cases, depth limiter (300) may be secured to cannula tube (124b) after cannula (120b) is positioned at a desired depth of insertion in cavity (1).

In some cases, it may be desirable to rapidly adjust the axial location of depth limiter (300) along cannula tube (124b) after depth limiter (300) has already been secured to cannula tube (124b). Thus, the clinician may selectively manipulate depth limiter (300) to rotate body portions (302, 304) relative to each other from the unclocked configuration to the clocked configuration, and relative to cannula tube (124b) from the fine adjustment configuration to the rapid adjustment configuration and may subsequently translate body portions (302, 304) relative to cannula tube (124b) to a new axial location. Once depth limiter (300) is at the new axial location, the clinician may selectively manipulate depth limiter (300) to rotate body portions (302, 304) relative to cannula tube (124b) from the rapid adjustment configuration to the fine adjustment configuration, which may include rotating body portions (302, 304) relative to each other from the clocked configuration to the unclocked configuration, and subsequently release depth limiter (300) while in the fine adjustment configuration, thereby allowing the threadable engagement between at least one tooth (320, 350) and ribs (128b) to maintain depth limiter (300) at the new axial location. In one example, a biasing of first and second body portions (302, 304) toward the unclocked configuration may automatically transition depth limiter (300) from the rapid adjustment configuration to the fine adjustment configuration when released by the clinician.

Likewise, it may be desirable to finely adjust the axial location of depth limiter (300) along cannula tube (124b) after depth limiter (300) has already been secured to cannula tube (124b). Thus, with depth limiter (300) in the fine adjustment configuration, which may include first and second body portions (302, 304) being in the unclocked configuration, the clinician may helically move body portions (302, 304) relative to cannula tube (124b) to fine-tune the axial location of depth limiter (300) relative to cannula tube (124b). During such movement, the body portions (302, 304) may be in the unclocked configuration at least as one or both teeth (320, 350) orbit about flat (170b) to inhibit depth limiter (300) from being briefly placed in the rapid adjustment configuration, and to thus prevent teeth (320, 350) from inadvertently sliding axially along flat (170b) or "skipping" ribs (128b) and thereby prevent depth limiter (300) from suddenly translating relative to cannula tube (124b). Once depth limiter (300) is at the fine-tuned axial location, the clinician may release depth limiter (300) while in the fine adjustment configuration, which may include first and second body portions (302, 304) being in the unclocked configuration, thereby allowing the threadable engagement between at least one tooth (320, 350) and ribs (128b) to maintain depth limiter (300) at the fine-tuned axial location. In one example, a biasing of first and second body portions (302, 304) toward the unclocked configuration may assist in maintaining depth limiter (300) in the fine adjustment configuration when released by the clinician.

Thus, the clinician may adjust the axial location of depth limiter (300) along cannula tube (124b), and may subsequently re-secure depth limiter (300) to cannula tube (124b) by simply releasing depth limiter (300) while in the fine adjustment configuration and/or unclocked configuration.

Depth limiter (300) may remain securely coupled to cannula tube (124b) during performance of the laparoscopic surgical procedure with distal hub (310) of depth limiter (300) resting against abdominal wall (2). In this manner, depth limiter (300) may assist in preventing cannula tip (not shown) of cannula assembly (112) from inadvertently entering deeper than desired into abdominal cavity (1) during performance of the laparoscopic surgical procedure.

Upon completion of the laparoscopic surgical procedure, depth limiter (300) may be withdrawn proximally from abdominal wall (2) together with cannula assembly (112). Depth limiter (300) may be rapidly removed from cannula tube (124b) by rotating body portions (302, 304) relative to each other toward the clocked configuration and relative to cannula tube (124b) toward the rapid adjustment configuration as described above and subsequently translating depth limiter (300) distally relative to cannula tube (124b). In one example, depth limiter (300) may be simply disposed of after completion of a single laparoscopic surgical procedure.

C. Exemplary Depth Limiter with Two Stability Thread-Chasing Teeth

In some instances, it may be desirable to provide a cannula depth limiter with improved stability and a reduced degree of rotation relative to the cannula tube for transitioning the depth limiter to a rapid adjustment configuration.

Figure 11:
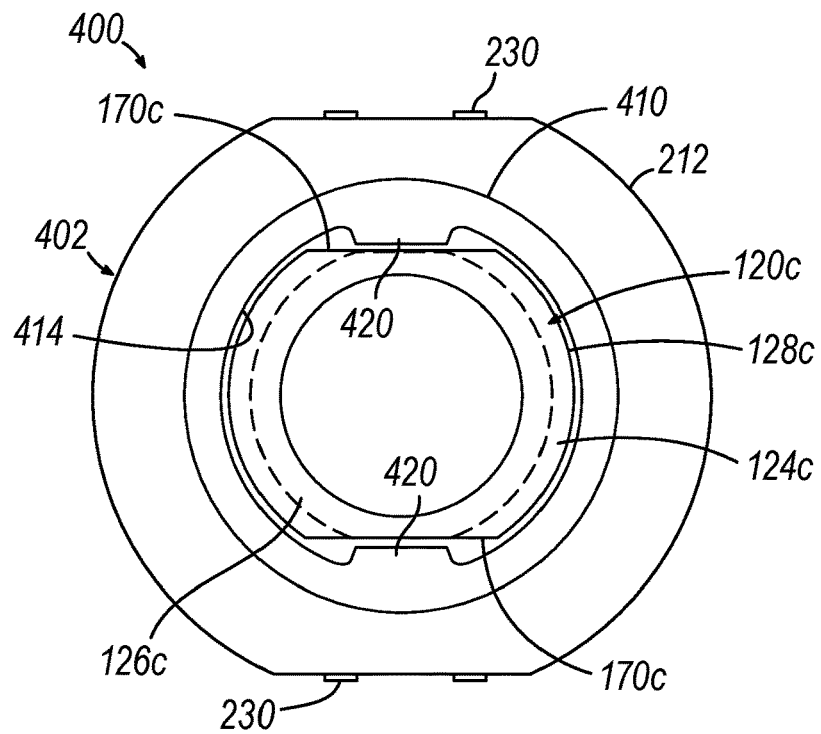
FIG. 11 depicts a bottom elevational view of another exemplary depth limiter selectively positioned about another exemplary cannula tube for the trocar of FIG. 4, showing two teeth of the depth limiter slidably engaged with respective flats of the cannula tube such that the depth limiter is in a rapid adjustment configuration.

FIG. 11 shows another alternative cannula (120c) for trocar (110) having an elongate cylindrical tube (124c) terminating at a cannula tip (126c) and including a plurality of tissue gripping features in the form of helical ribs (128c). Cannula tube (124c) is generally similar to cannula tube (124a), except that cannula tube (124c) includes a pair of tracks in the form of diametrically-opposed flats (170c).

FIG. 11 further shows a third exemplary depth limiter (400) selectively coupled to cannula tube (124c) of trocar (110) for selectively limiting the depth to which trocar (110) may travel distally into abdominal wall (2). Depth limiter (400) is substantially similar to depth limiter (200) and includes various similar features. Thus, only different features are described below.

Depth limiter (400) of the present version includes a body portion (402) including a distal cylindrical hub (410) and proximal generally annular flange (212) extending radially outwardly therefrom. Hub (410) defines a generally cylindrical bore (414) and is generally similar to hub (210), except that hub (410) includes a pair of diametrically-opposed flat teeth (420) extending radially inwardly from a peripheral edge of bore (414) and configured to selectively threadably engage ribs (128c) of cannula tube (124c) and to selectively slidably engage flats (170c) of cannula tube (124c).

By providing pairs of flats (170c) and teeth (420), cannula tube (124c) and depth limiter (400) may cooperate to provide improved stability of depth limiter (400) relative to cannula tube (124c), and to provide a reduced degree of relative rotation between depth limiter (400) and cannula tube (124c) for transitioning depth limiter (400) from a fine adjustment configuration to the illustrated rapid adjustment configuration.

D. Exemplary Depth Limiter with Three Stability Thread-Chasing Teeth

In some instances, it may be desirable to provide a cannula depth limiter with further improved stability and a further reduced degree of rotation relative to the cannula tube for transitioning the depth limiter to a rapid adjustment configuration.

Figure 12:
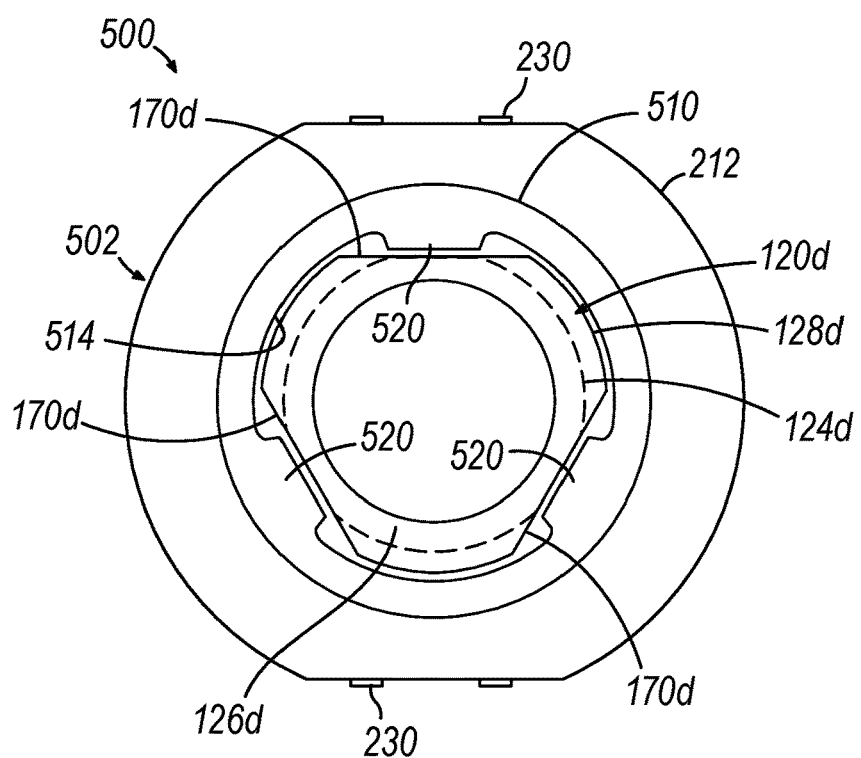
FIG. 12 depicts a bottom elevational view of another exemplary depth limiter selectively positioned about another exemplary cannula tube for the trocar of FIG. 4, showing three teeth of the depth limiter slidably engaged with respective flats of the cannula tube such that the depth limiter is in a rapid adjustment configuration.

FIG. 12 shows another alternative cannula (120d) for trocar (110) having an elongate cylindrical tube (124d) terminating at a cannula tip (126d) and including a plurality of tissue gripping features in the form of helical ribs (128d). Cannula tube (124d) is generally similar to cannula tube (124a), except that cannula tube (124d) includes tracks in the form of three flats (170d) circumferentially arranged at equal intervals.

FIG. 12 further shows a fourth exemplary depth limiter (500) selectively coupled to cannula tube (124d) of trocar (110) for selectively limiting the depth to which trocar (110) may travel distally into abdominal wall (2). Depth limiter (500) is substantially similar to depth limiter (200) and includes various similar features. Thus, only different features are described below.

Depth limiter (500) of the present version includes a body portion (502) including a distal cylindrical hub (510) and proximal generally annular flange (212) extending radially outwardly therefrom. Hub (510) defines a generally cylindrical bore (514) and is generally similar to hub (210), except that hub (510) includes three flat teeth (520) circumferentially arranged at equal intervals and extending radially inwardly from a peripheral edge of bore (514) and configured to selectively threadably engage ribs (128d) of cannula tube (124d) and to selectively slidably engage flats (170d) of cannula tube (124d).

By providing three sets of flats (170d) and teeth (520), cannula tube (124d) and depth limiter (500) may cooperate to provide further improved stability of depth limiter (500) relative to cannula tube (124d), and to provide a further reduced degree of relative rotation between depth limiter (500) and cannula tube (124d) for transitioning depth limiter (500) from a fine adjustment configuration to the illustrated rapid adjustment configuration.

It will be appreciated that any suitable number of flats (170a, 170b, 170c, 170d) and teeth (220, 320, 350, 420, 520) may be provided for allowing teeth (220, 320, 350, 420, 520) to selectively threadably engage ribs (128a, 128b, 128c, 128d) of cannula tube (124a, 124b, 124c, 124d) and to selectively slidably engage flats (170a, 170b, 170c, 170d) of cannula tube (124a, 124b, 124c, 124d). For example, flats (170a, 170b, 170c, 170d) and teeth (220, 320, 350, 420, 520) may be provided in ratios of 3:3, 3:1, 2:2, 2:1, or 1:1, or in any other suitable ratios.

E. Exemplary Threaded Depth Limiter with Living Hinge

In some instances, it may be desirable to provide a cannula depth limiter with a rapid adjustment configuration that differs from the rapid adjustment configurations of depth limiters (200, 300, 400, 500) described above.

Figure 13:
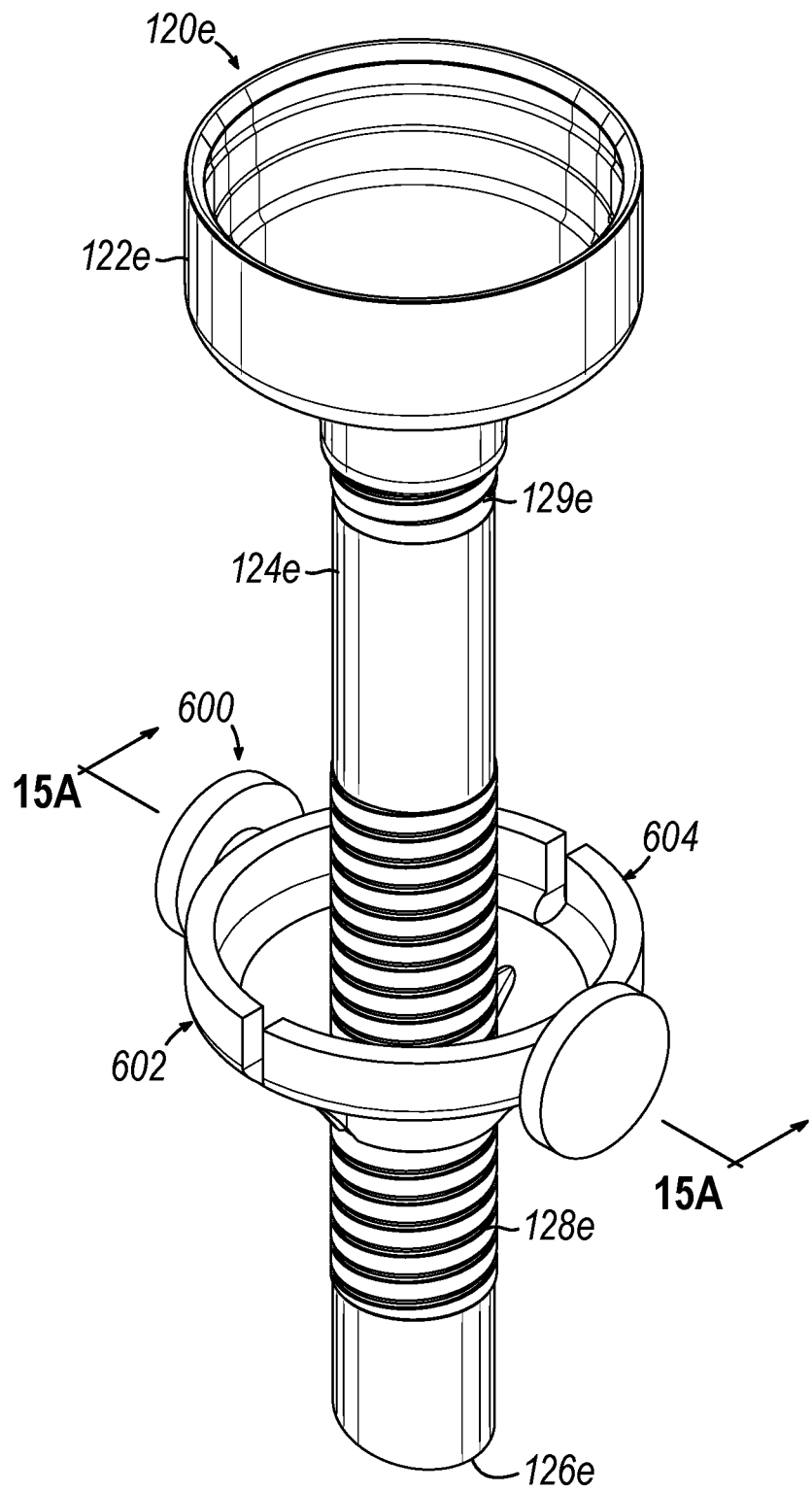
FIG. 13 depicts a perspective view of another exemplary cannula for the trocar of FIG. 4, showing another exemplary depth limiter selectively positioned about the cannula tube of the cannula.

FIG. 13 shows an alternative cannula (120e) for trocar (110) having a bell-shaped hub (122e) at a proximal end thereof, and an elongate cylindrical tube (124e) extending distally from hub (122e) and terminating at a cannula tip (126e). An outer surface of cannula tube (124e) includes at least one tissue gripping feature in the form of a helical rib (128e) that extends around a medial portion of cannula tube (124e). Rib (128e) is configured to grip the layers of abdominal wall tissue through which cannula (120e) is inserted, and thereby assist in stabilizing cannula (120e) in axial and radial directions while cannula (120e) is positioned within the opening formed in the abdominal wall (2) of a patient. Outer surface of cannula tube (124e) also includes a supplemental helical rib (129e) that extends around a proximal portion of cannula tube (124e) and is configured similarly to rib (128e), the purpose of which is described below. Cannula (120e) of the present example may be suitably constructed of a robust material, such as surgical steel, such that cannula (120e) may be sterilized and reused for multiple surgical procedures, similar to cannula (120) and obturator (116) described above.

FIG. 13 further shows a fifth exemplary depth limiter (600) selectively coupled to cannula tube (124e) of trocar (110). As described in greater detail below, depth limiter (600) may selectively limit the depth to which trocar (110) may travel distally into abdominal wall (2).

Figure 14:
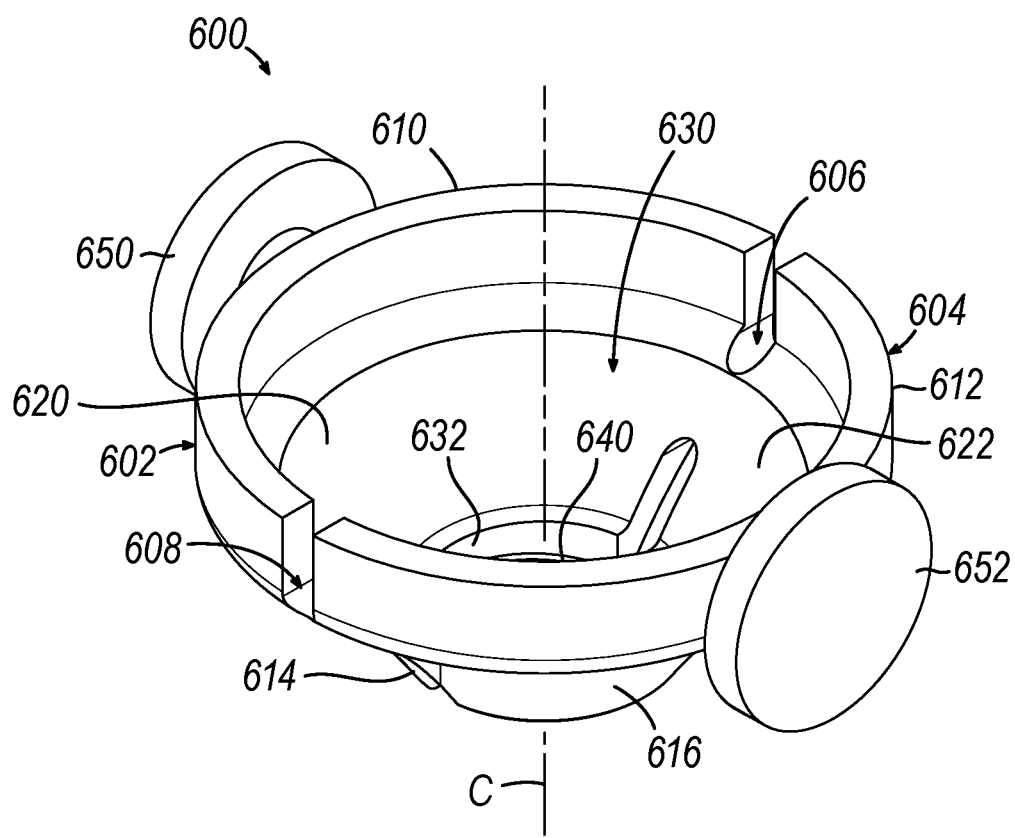
FIG. 14 depicts a perspective view of the depth limiter of FIG. 13.
Figure 15A:
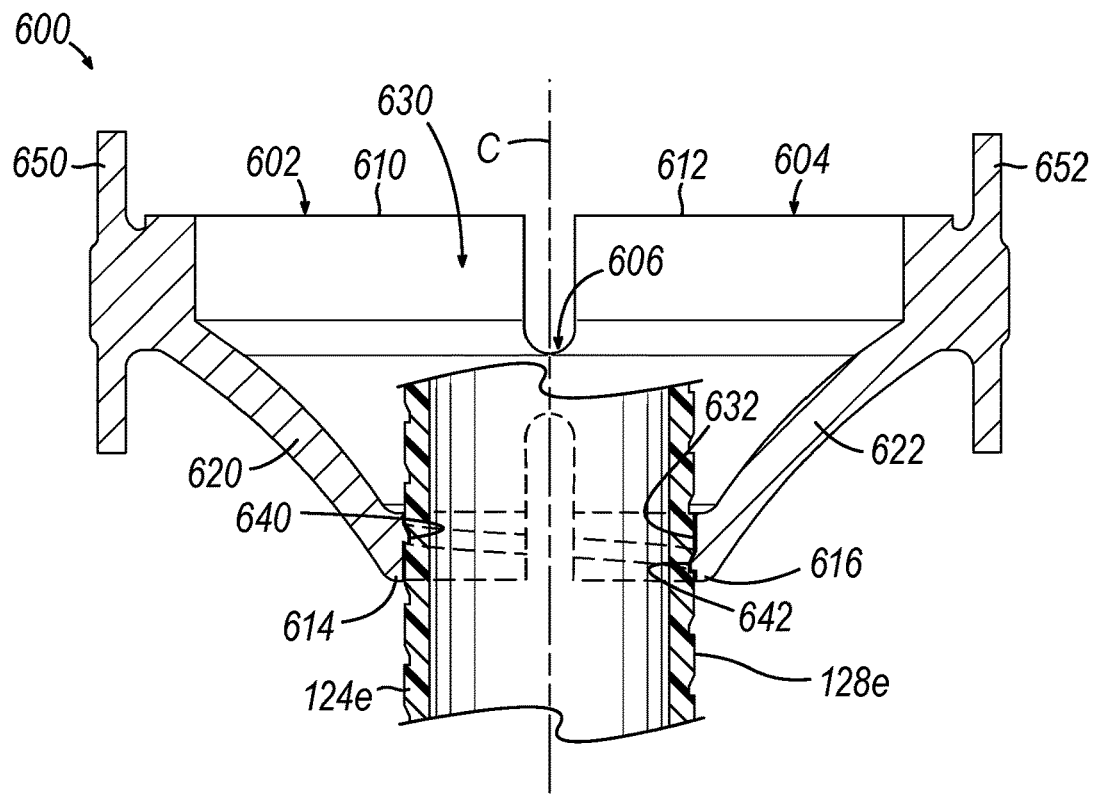
FIG. 15A depicts a cross-sectional view of the cannula of FIG. 13, taken along section line 15A-15A in FIG. 13, showing cleats of the depth limiter of FIG. 13 threadably engaged with a helical stability rib of the cannula tube such that the depth limiter is in a fine adjustment configuration.
Figure 15B:
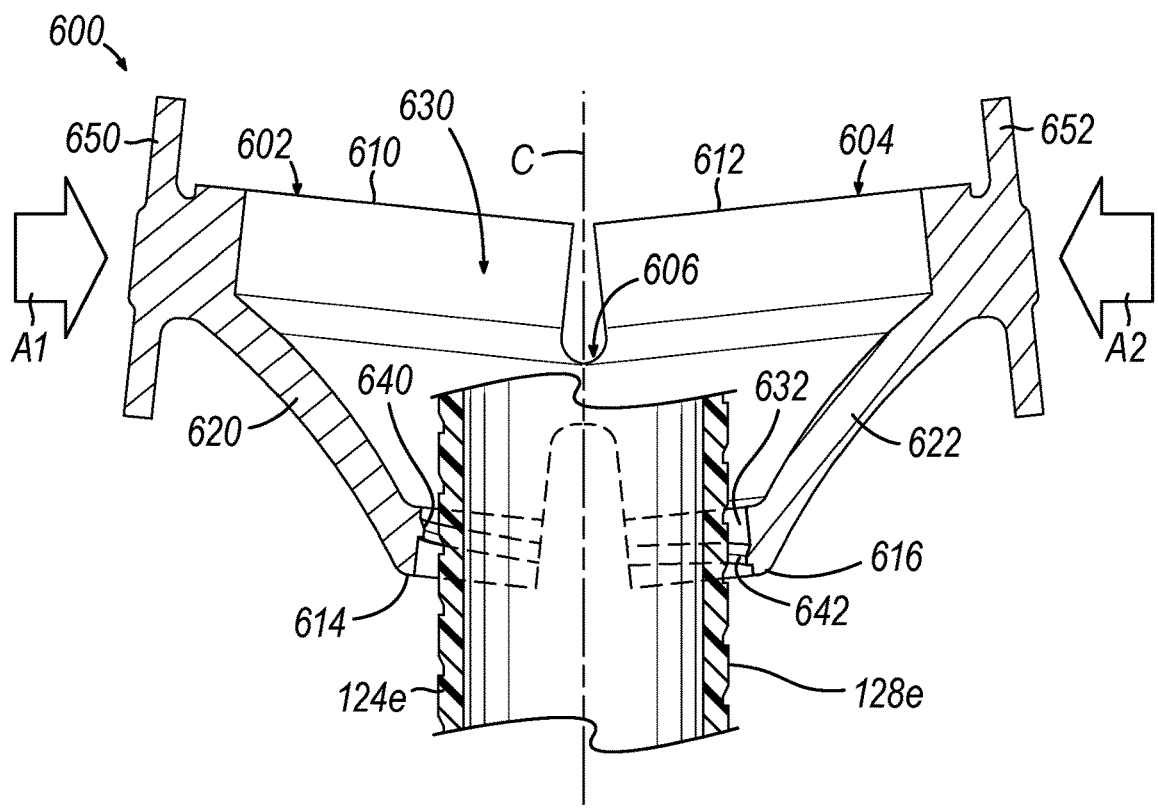
FIG. 15B depicts a cross-sectional view similar to FIG. 15A, showing the cleats of the depth limiter of FIG. 13 pivoted radially outwardly from the helical stability rib and threadably disengaged therefrom such that the depth limiter is in a rapid adjustment configuration.

As best shown in FIGS. 14-15B, depth limiter (600) includes first and second body portions (602, 604) pivotably coupled to each other by first and second hinges (606, 608) such that first and second body portions (602, 604) are pivotable relative to each other between at least one fine adjustment configuration (e.g., FIG. 15A) and at least one rapid adjustment configuration (e.g., FIG. 15B). In the example shown, first and second body portions (602, 604) and first and second hinges (606, 608) are integrally formed together as a unitary piece. For example, first and second body portions (602, 604) and first and second hinges (606, 608) may be molded together as a single component, such as from a polymeric material, including one or more plastics. Such a construction may allow depth limiter (600) to be considered a disposable unit, intended to be separated from cannula (120e) and replaced after each procedure. For instance, such a construction may allow depth limiter (600) to be easily manufactured and sold at a price point that renders depth limiter (600) suitable for disposal after a single use, similar to trocar (10) and seal assembly (130) described above. In other versions, one or more portions of depth limiter (600) may be formed of surgical steel or other material suitable to render depth limiter sterilizable and reusable for multiple surgical procedures. In any event, the illustrated first and second hinges (606, 608) includes a thinned portion of the same material as first and second body portions (602, 604) such that first and second body portions (602, 604) are permitted to bend thereabout, such that first and second hinges (606, 608) may be considered "living" hinges.

In the example shown, depth limiter (600) has a generally hollow, frustoconical profile. To this end, first and second body portions (602, 604) include first and second generally C-shaped proximal walls (610, 612), first and second generally C-shaped distal walls (614, 616), and first and second generally C-shaped medial walls (620, 622), respectively. As shown, first and second proximal walls (610, 612) are positioned relatively radially outwardly, first and second distal walls (614, 616) are positioned relatively radially inwardly, and first and second medial walls (620, 622) taper radially inwardly in a distal direction from first and second proximal walls (610, 612) to first and second distal walls (614, 616), respectively. First and second hinges (206, 208) are positioned between lateral ends of first and second body portions (602, 604) at respective interfaces between first and second medial walls (620, 622) to collectively define a hinge axis perpendicular to a central axis (C) of depth limiter (600) such that first and second proximal walls (610, 612) are configured to be pivoted toward each other about first and second hinges (206, 208) and such that first and second distal walls (614, 616) are configured to be pivoted away from each other about first and second hinges (206, 208) when first and second body portions (602, 604) are in the rapid adjustment configuration. In this manner, first and second body portions (602, 604) collectively define a deformable, generally frustoconical bore (630) which extends longitudinally along central axis (C) of depth limiter (600) and which includes a generally cylindrical distal bore portion (632) having a relatively constricted configuration when first and second body portions (602, 604) are in the fine adjustment configuration, and having a relatively unconstricted configuration when first and second body portions (602, 604) are in the rapid adjustment configuration.

As best shown in FIGS. 15A and 15B, first and second distal walls (614, 616) include first and second semi-helical cleats (640, 642), respectively, extending radially inwardly from a peripheral edge of distal bore portion (632) and configured to selectively threadably engage rib (128e) of cannula tube (124e). In this regard, first and second cleats (640, 642) may collectively define a helical path similar to that defined by rib (128e) such that cleats (640, 642) may be capable of simultaneously threadably engaging rib (128e), at least when first and second body portions (602, 604) are in the fine adjustment configuration. The illustrated first and second proximal walls (610, 612) include diametrically opposed first and second suture tie posts which may also be considered first and second finger grips (650, 652), respectively, each positioned generally centrally between and proximally relative to first and second hinges (606, 608). First and second finger grips (650, 652) are configured to provide a visual and/or tactile indication to a user of the locations on first and second body portions (602, 604) to be squeezed or pinched toward each other for effectively and ergonomically pivoting first and second body portions (602, 604) relative to each other about first and second hinges (606, 608) toward the rapid adjustment configuration, as described in greater detail below.

More particularly, and as shown in FIG. 15A, when first and second body portions (602, 604) are in the fine adjustment configuration, first and second distal walls (614, 616) may collectively form a first effective cross dimension that extends diametrically through central axis (C) and is sized to position first and second cleats (640, 642) at a substantially same radial distance from central axis (C) as rib (128e) such that first and second cleats (640, 642) are permitted to threadably engage with rib (128e). The interaction between cleats (640, 642) and rib (128e) may be configured to restrict axial movement of depth limiter (600) relative to cannula tube (124e) and/or allow for fine axial movement of depth limiter (600) relative to cannula tube (124e), such as by constraining depth limiter (600) to helical movement relative to cannula tube (124e).

As shown in FIG. 15B, when first and second body portions (602, 604) are in the rapid adjustment configuration, first and second distal walls (614, 616) may collectively form a second effective cross dimension that extends diametrically through central axis (C) and is sized to position first and second cleats (640, 642) radially outwardly relative to rib (128e) such that first and second cleats (640, 642) are prevented from threadably engaging with rib (128e). The disengagement of cleats (640, 642) from rib (128e) may allow for rapid axial movement of depth limiter (600) relative to cannula tube (124e), such as by allowing depth limiter (600) to be translatable relative to cannula tube (124e).

Finger grips (650, 652) may be configured to provide a visual and/or tactile indication to a user of the locations on first and second body portions (602, 604) to be gripped for effectively and ergonomically translating depth limiter (600) relative to cannula tube (124e) while in the rapid adjustment configuration and/or moving depth limiter (600) helically relative to cannula tube (124e) while in the fine adjustment configuration, in addition to providing a visual and/or tactile indication to a user of the locations on first and second body portions (602, 604) to be squeezed or pinched together for effectively and ergonomically pivoting first and second body portions (602, 604) relative to each other about first and second hinges (606, 608) toward the rapid adjustment configuration.

In some examples, first and second body portions (602, 604) may be biased toward the fine adjustment configuration. For example, first and second distal walls (614, 616) may be resiliently biased toward each other and first and second proximal walls (610, 612) may be resiliently biased away from each other, such as via a torsion spring member (not shown) incorporated into first and second hinges (606, 608) or an external spring member (not shown) positioned directly between first and second proximal walls (610, 612). In other examples, first and second hinges (606, 608) may each be constructed as a living hinge having a shape and thickness suitable to impart opposing resilient bias on first and second proximal walls (610, 612) at their lateral ends. In this manner, first and second body portions (602, 604) may be configured to automatically move from the rapid adjustment configuration toward the fine adjustment configuration in response to an absence of external forces applied to first and second finger grips (650, 652).

In one example, first and second cleats (640, 642) are configured to selectively threadably engage supplemental rib (129e) of cannula tube (124e), such as for storing depth limiter (600) in a proximal axial location along cannula tube (124e) near hub (122e) prior to use.

During operation, and with continuing reference to FIGS. 15A and 15B, depth limiter (600) may be initially positioned about cannula tube (124e) of trocar (110) such that cannula tube (124e) is received within bore (630) prior to deployment of trocar (110) into the patient's abdominal cavity (1). During deployment of trocar (110) into abdominal cavity (1), first and second body portions (602, 604) may be in either the rapid adjustment configuration or the fine adjustment configuration, as may be desired.

In some cases, the clinician may desire to allow rapid axial movement of depth limiter (600) relative to cannula tube (124e) of trocar (110) during deployment. Thus, the clinician may choose to move first and second body portions (602, 604) from the fine adjustment configuration toward the rapid adjustment configuration. To this end, the clinician may squeeze or pinch first and second finger grips (650, 652) toward each other via the clinician's thumb and finger as indicated by first and second arrows (A1, A2), respectively, in FIG. 15B to effectively and ergonomically move first and second body portions (602, 604) toward the rapid adjustment configuration. By maintaining first and second body portions (602, 604) in the rapid adjustment configuration, first and second cleats (640, 642) may be unconstrained by rib (128e). More particularly, first and second cleats (640, 642) may be positioned radially outwardly relative to rib (128e) to allow translation of depth limiter (600) relative to cannula tube (124e) of trocar (110), as shown in FIG. 15B.

In other cases, the clinician may desire to restrict axial movement of depth limiter (600) relative to cannula tube (124e) of trocar (110) during deployment. For example, the clinician may desire to position depth limiter (600) at a predetermined axial location along cannula tube (124e) corresponding to a desired depth of insertion of cannula (120e) within cavity (1). Thus, the clinician may choose to move first and second body portions (602, 604) from the rapid adjustment configuration toward the fine adjustment configuration. In one example, a biasing of first and second body portions (602, 604) toward the fine adjustment configuration may assist in such movement. By moving first and second body portions (602, 604) toward the fine adjustment configuration, first and second cleats (640, 642) may be constrained to helical movement by rib (128e). More particularly, first and second cleats (640, 642) may be positioned at a substantial same radial distance from central axis (C) as rib (128e) to allow substantially only helical movement of depth limiter (600) relative to cannula tube (124e), as shown in FIG. 15A. Once depth limiter (600) is at the predetermined axial location, the clinician may release depth limiter (600) while still in the fine adjustment configuration, thereby allowing the threadable engagement between cleats (640, 642) and rib (128e) to maintain depth limiter (600) at the predetermined axial location.

With depth limiter (600) positioned about cannula tube (124e) in either an axially restricted or unrestricted state, the clinician may deploy trocar (110) into the patient's abdominal cavity (1) as described above with respect to FIGS. 3A and 3B to position cannula (120e) at a desired depth of insertion in cavity (1). In cases where depth limiter (600) is secured to cannula tube (124e) during deployment at a predetermined axial location along cannula tube (124e) corresponding to a desired depth of insertion of cannula (120e) within cavity (1), contact between distal walls (614, 616) of depth limiter (600) and abdominal wall (2) may provide a visual and/or tactile indication to the clinician that cannula (120e) has reached the desired depth of insertion in cavity (1). In this manner, depth limiter (600) may assist in preventing distal tip (154) of obturator (116) and/or cannula tip (126e) of cannula assembly (112) from inadvertently entering deeper than desired into abdominal cavity (1) during deployment. In other cases, depth limiter (600) may be secured to cannula tube (124e) after cannula (120e) is positioned at a desired depth of insertion in cavity (1).

In some cases, it may be desirable to rapidly adjust the axial location of depth limiter (600) along cannula tube (124e) after depth limiter (600) has already been secured to cannula tube (124e). Thus, the clinician may selectively manipulate depth limiter (600) to pivot body portions (602, 604) relative to each other from the fine adjustment configuration to the rapid adjustment configuration and may subsequently translate body portions (602, 604) relative to cannula tube (124e) to a new axial location. Once depth limiter (600) is at the new axial location, the clinician may selectively manipulate depth limiter (600) to pivot body portions (602, 604) relative to each other from the rapid adjustment configuration to the fine adjustment configuration and subsequently release depth limiter (300) while in the fine adjustment configuration, thereby allowing the threadable engagement between cleats (640, 642) and rib (128e) to maintain depth limiter (600) at the new axial location. In one example, a biasing of first and second body portions (602, 604) toward the fine adjustment configuration may automatically transition depth limiter (600) from the rapid adjustment configuration to the fine adjustment configuration when released by the clinician.

Likewise, it may be desirable to finely adjust the axial location of depth limiter (600) along cannula tube (124e) after depth limiter (600) has already been secured to cannula tube (124e). Thus, with depth limiter (600) in the fine adjustment configuration, the clinician may helically move body portions (602, 604) relative to cannula tube (124e) to fine-tune the axial location of depth limiter (600) relative to cannula tube (124e). Once depth limiter (600) is at the fine-tuned axial location, the clinician may release depth limiter (600) while in the fine adjustment configuration, thereby allowing the threadable engagement between cleats (640, 642) and ribs (128e) to maintain depth limiter (600) at the fine-tuned axial location. In one example, a biasing of first and second body portions (602, 604) toward the fine adjustment configuration may assist in maintaining depth limiter (600) in the fine adjustment configuration when released by the clinician.

Thus, the clinician may adjust the axial location of depth limiter (600) along cannula tube (124e), and may subsequently re-secure depth limiter (600) to cannula tube (124e) by simply releasing depth limiter (600) while in the fine adjustment configuration.

Depth limiter (600) may remain securely coupled to cannula tube (124e) during performance of the laparoscopic surgical procedure with distal walls (614, 616) of depth limiter (600) resting against abdominal wall (2). In this manner, depth limiter (600) may assist in preventing cannula tip (126e) of cannula assembly (112) from inadvertently entering deeper than desired into abdominal cavity (1) during performance of the laparoscopic surgical procedure.

Upon completion of the laparoscopic surgical procedure, depth limiter (600) may be withdrawn proximally from abdominal wall (2) together with cannula assembly (112). Depth limiter (600) may be rapidly removed from cannula tube (124e) by pivoting body portions (602, 604) relative to each other toward the rapid adjustment configuration as described above and subsequently translating depth limiter (600) distally relative to cannula tube (124e). In one example, depth limiter (600) may be simply disposed of after completion of a single laparoscopic surgical procedure.

F. Exemplary Depth Limiter and Cannula Tube with Semi-Buttress Stability Threads In some instances, it may be desirable to provide a cannula depth limiter with a reduced degree of rotation relative to the cannula tube for adjusting an axial location of the depth limiter when in a fine adjustment configuration, and with a greater retention force than an insertion force applied to the depth limiter by the cannula tube.

Figure 16:
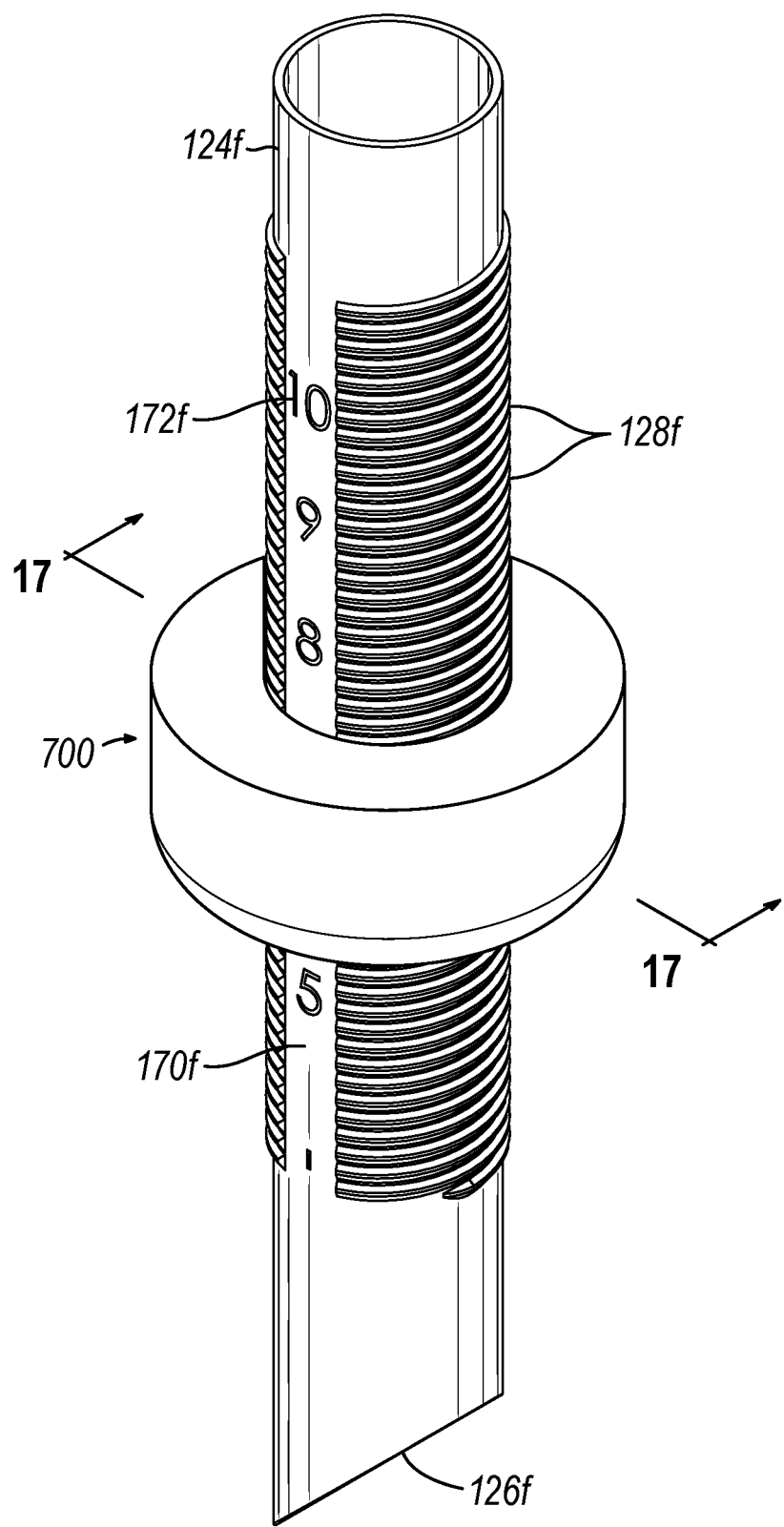
FIG. 16 depicts a perspective view of another exemplary cannula tube for the trocar of FIG. 4, showing another exemplary depth limiter selectively positioned about the cannula tube.
Figure 17:
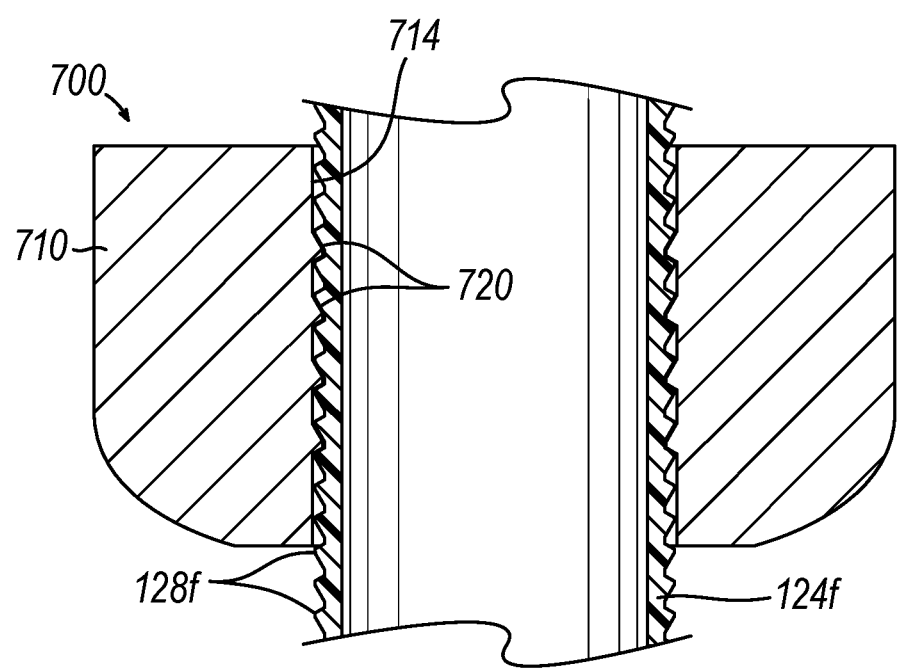
FIG. 17 depicts a cross-sectional view of the cannula tube of FIG. 16, taken along section line 17-17 in FIG. 16, showing teeth of the depth limiter of FIG. 16 threadably engaged with helical stability ribs of the cannula tube such that the depth limiter is in a fine adjustment configuration.

FIGS. 16 and 17 show another alternative cannula tube (124f) for trocar (110) terminating at a cannula tip (126f) and including a plurality of tissue gripping features in the form of helical ribs (128f). Cannula tube (124f) is generally similar to cannula tube (124a), except that cannula tube (124f) includes tracks in the form of a pair of diametrically-opposed channels (170f) (one shown) with depth identifying indicia (172f) provided thereon and configured to provide a visual indication of an insertion depth of cannula tube (124f) relative to cavity (1), for example. Channels (170f) function substantially similarly to flats (170a, 170b, 170c, 170d) discussed above. Moreover, ribs (128f) have a double-start configuration such that alternating ribs (128f) are offset from each other by 180 degrees and are a half pitch apart from each other. As best shown in FIG. 17, each rib (128f) has a semi-buttress configuration.

FIGS. 16 and 17 further show a sixth exemplary depth limiter (700) selectively coupled to cannula tube (124f) of trocar (110) for selectively limiting the depth to which trocar (110) may travel distally into abdominal wall (2). Depth limiter (700) is substantially similar to depth limiter (200) and includes various similar features. Thus, only different features are described below.

Depth limiter (700) of the present version includes a cylindrical hub (710) defining a generally cylindrical bore (714) and including a plurality of teeth (720) extending radially inwardly from a peripheral edge of bore (714) and configured to selectively threadably engage alternating ribs (128f) of cannula tube (124f) and to selectively slidably engage channels (170f) of cannula tube (124f).

By providing a pair of channels (170f) and a plurality of teeth (720), cannula tube (124f) and depth limiter (700) may cooperate to provide improved stability of depth limiter (700) relative to cannula tube (124f), and to provide a reduced degree of relative rotation between depth limiter (700) and cannula tube (124f) for transitioning depth limiter (700) from the illustrated fine adjustment configuration to a rapid adjustment configuration. By providing ribs (128f) having a double-start configuration and teeth (720) configured to threadably engage alternating ribs (128f), cannula tube (124f) and depth limiter (700) may cooperate to provide a reduced degree of relative rotation between depth limiter (700) and cannula tube (124f) for adjusting an axial location of the depth limiter (700) (e.g., increased axial adjustment per rotation) when in the fine adjustment configuration. And by providing ribs (128f) having a semi-buttress configuration, cannula tube (124f) may apply a greater retention force than insertion force to depth limiter (700).

G. Exemplary Depth Limiter and Cannula Tube with Multiple Offset Stability Threads In some instances, it may be desirable to provide a cannula depth limiter with a further reduced degree of rotation relative to the cannula tube for adjusting an axial location of the depth limiter, and with a retention mechanism for preventing inadvertent disengagement of the depth limiter from the cannula tube.

Figure 18:
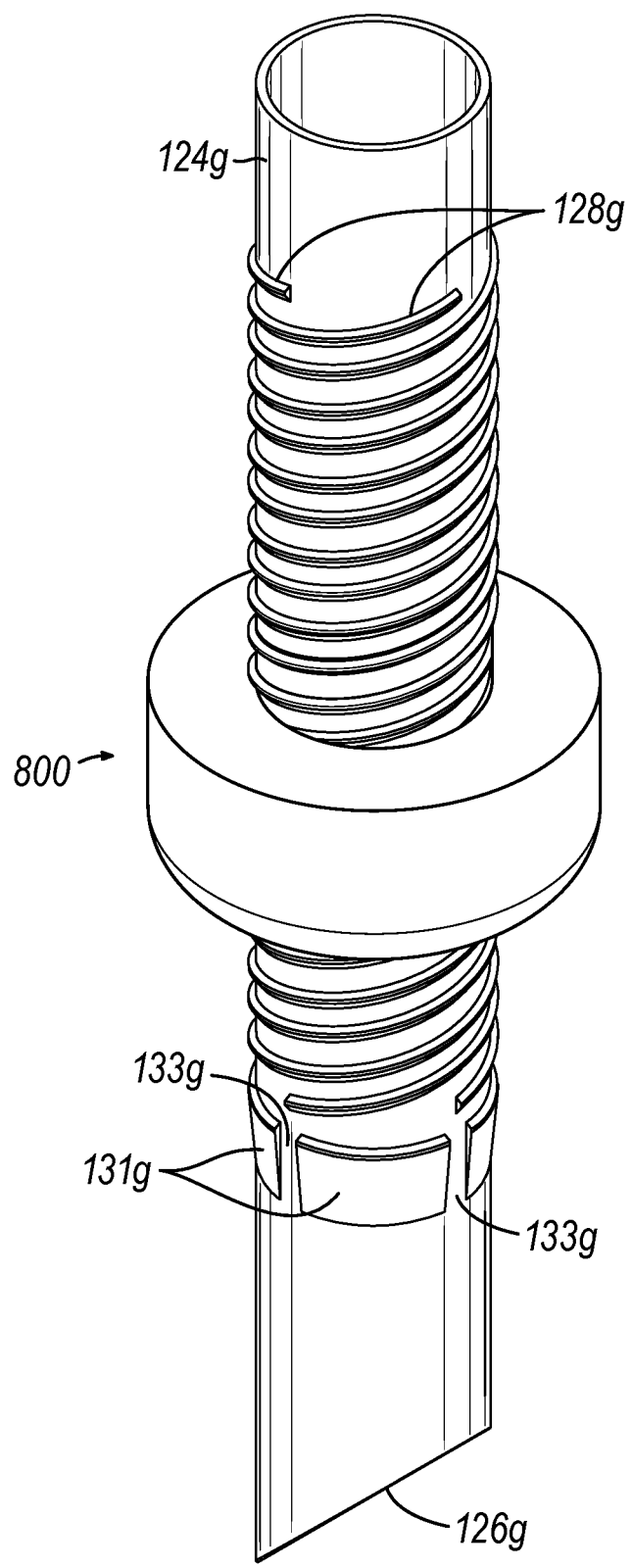
FIG. 18 depicts a perspective view of another exemplary cannula tube for the trocar of FIG. 4, showing another exemplary depth limiter selectively positioned about the cannula tube.
Figure 19:
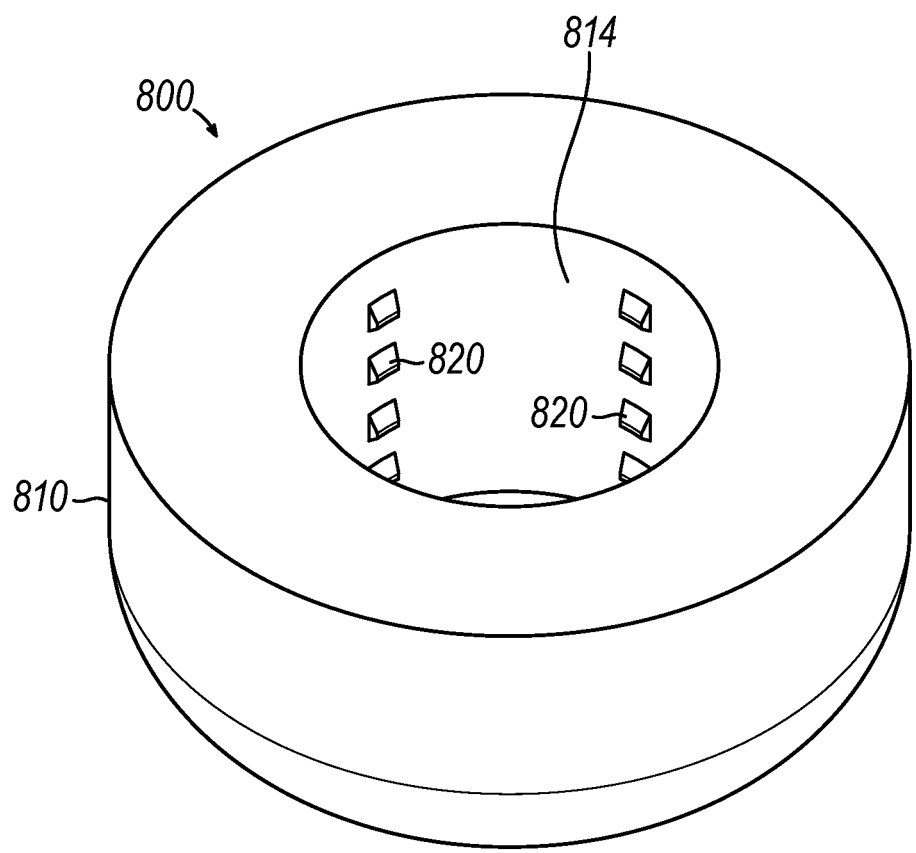
FIG. 19 depicts a perspective view of the depth limiter of FIG. 18.

FIG. 18 shows another alternative cannula tube (124g) for trocar (110) terminating at a cannula tip (126g). Cannula tube (124g) is generally similar to cannula tube (124a), except that cannula tube (124g) omits flats and includes a plurality of tissue gripping features in the form of four helical ribs (128g) offset from each other by 90 degrees and a quarter pitch apart from each other. Moreover, cannula tube (124g) includes four insertion ramps (131g) tapered radially inwardly in a distal direction from a major external cross dimension of ribs (128g) and spaced apart from each other by respective notches (133g). Each notch (133g) is generally radially aligned with a distal start of a corresponding ribs (128g).

FIG. 18 further shows a seventh exemplary depth limiter (800) selectively coupled to cannula tube (124g) of trocar (110) for selectively limiting the depth to which trocar (110) may travel distally into abdominal wall (2). Depth limiter (800) is substantially similar to depth limiter (200) and includes various similar features. Thus, only different features are described below.

As best shown in FIG. 17, depth limiter (800) of the present version includes a cylindrical hub (810) defining a generally cylindrical bore (814) and including four sets (two shown) of four radially-aligned teeth (820) extending radially inwardly from a peripheral edge of bore (814) and configured to selectively threadably engage respective ribs (128g) of cannula tube (124g). Sets of teeth (820) are offset from each other by 90 degrees and have a pitch equal to a quarter of that of ribs (128g). Teeth (820) are each sized to be slidably received by respective notches (133g).

By providing four ribs (128g) and four sets of teeth (820) configured to threadably engage respective ribs (128g), cannula tube (124g) and depth limiter (800) may cooperate to provide a further reduced degree of relative rotation between depth limiter (800) and cannula tube (124g) for adjusting an axial location of the depth limiter (800) (e.g., increased axial adjustment per rotation). And by providing ramps (131g) and notches (133g), cannula tube (124g) may cooperate with depth limiter (800) to permit assembly and intentional disassembly of depth limiter (800) onto and from cannula tube (124g) by passing teeth (820) through notches (133g) while preventing inadvertent disengagement of depth limiter (800) from cannula tube (124g).

H. Exemplary Depth Limiter with Stability Thread-Chasing Tabs

In some instances, it may be desirable to provide a cannula depth limiter with a reduced degree of rotation relative to the cannula tube for adjusting an axial location of the depth limiter, and with an improved manipulability.

Figure 20:
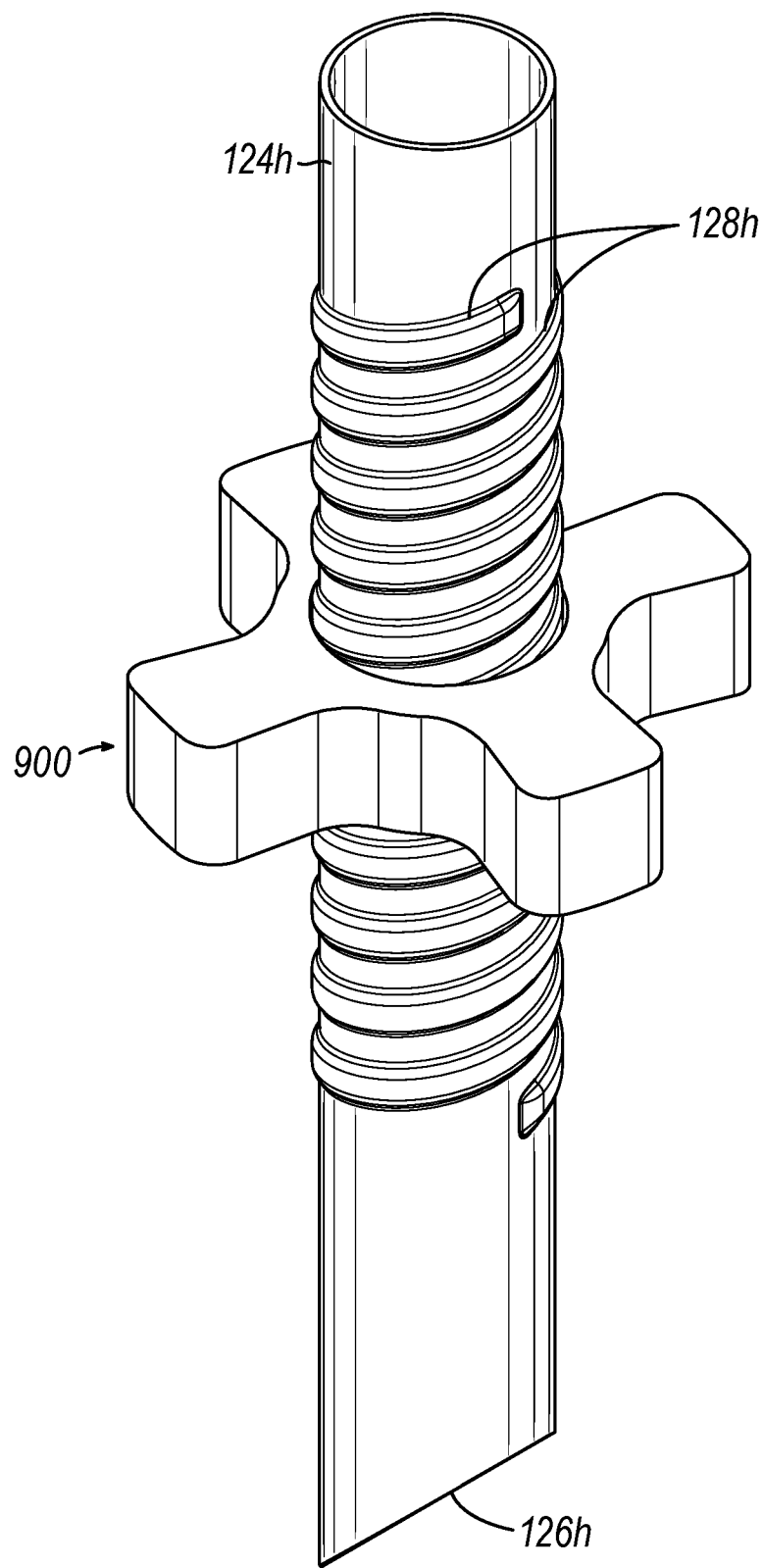
FIG. 20 depicts a perspective view of another exemplary cannula tube for the trocar of FIG. 4, showing another exemplary depth limiter selectively positioned about the cannula tube.

FIG. 20 shows another alternative cannula tube (124h) for trocar (110) terminating at a cannula tip (126h). Cannula tube (124h) is generally similar to cannula tube (124a), except that cannula tube (124h) omits flats and includes a plurality of tissue gripping features in the form of two helical ribs (128h) offset from each other by 180 degrees and a half pitch apart from each other. In one example, ribs (128h) may be hydroformed on cannula tube (124h). It will be appreciated that ribs (128h) may be formed on cannula tube (124h) in any other suitable manner, such as machining or molding. Likewise, cannula tube (124h) may be hydroformed or manufactured in any other suitable manner, such as by first drawing a flat sheet and subsequently welding the flat sheet to itself in a cylindrical configuration.

FIG. 20 further shows an eighth exemplary depth limiter (900) selectively coupled to cannula tube (124h) of trocar (110) for selectively limiting the depth to which trocar (110) may travel distally into abdominal wall (2). Depth limiter (900) is substantially similar to depth limiter (200) and includes various similar features. Thus, only different features are described below.

Figure 21:
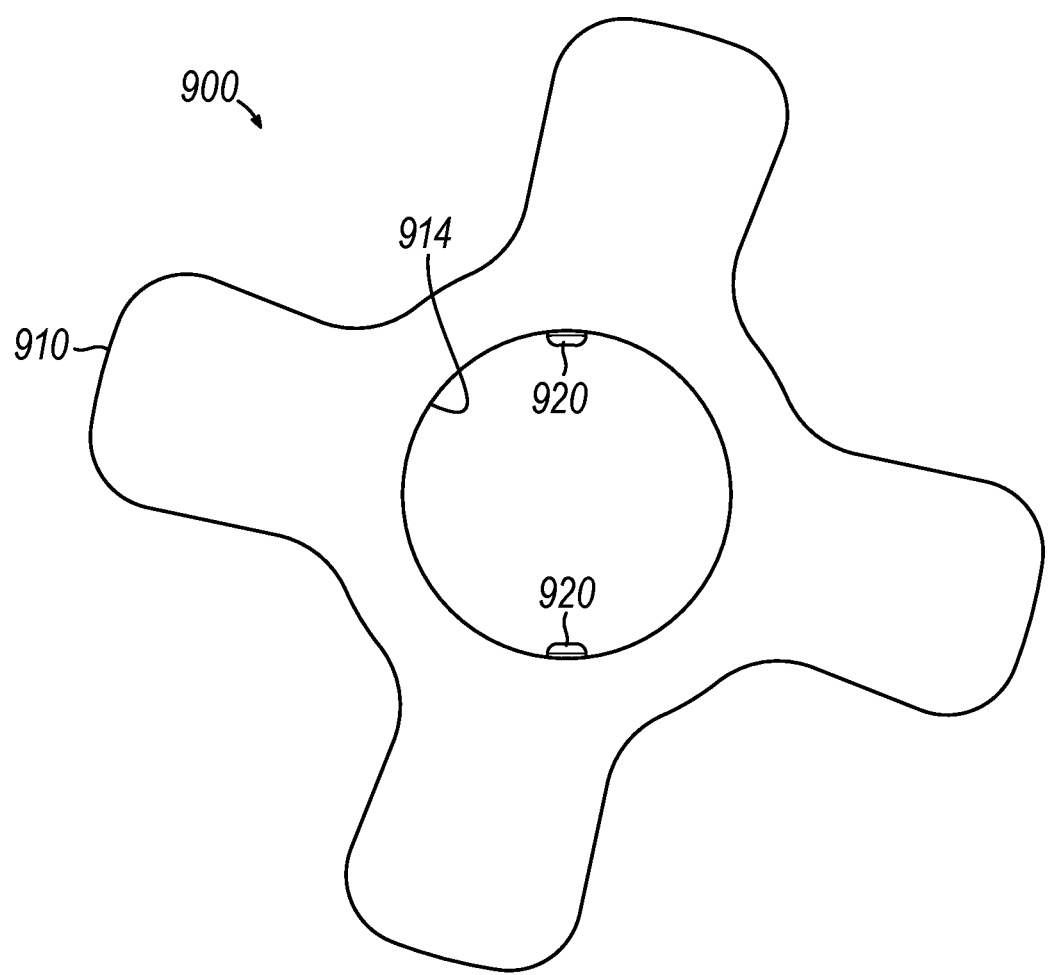
FIG. 21 depicts a top elevational view of the depth limiter of FIG. 20.

As best shown in FIG. 21, depth limiter (900) of the present version includes an x-shaped hub (910) defining a generally cylindrical bore (914) and including a pair of diametrically-opposed tabs (920) extending radially inwardly from a peripheral edge of bore (914) and configured to selectively threadably engage ribs (128h) of cannula tube (124h).

By providing pairs of ribs (128h) and tabs (920), cannula tube (124h) and depth limiter (900) may cooperate to provide improved stability of depth limiter (900) relative to cannula tube (124h), and to provide a reduced degree of relative rotation between depth limiter (900) and cannula tube (124h) for adjusting an axial location of the depth limiter (900) (e.g., increased axial adjustment per rotation). And by providing x-shaped hub (910), depth limiter (900) may provide improved manipulability.

I. Exemplary Depth Limiter and Cannula Tube with Stability Ribs and Depth Limiter-Gripping Threads In some instances, it may be desirable to provide a cannula depth limiter with a further reduced degree of rotation relative to the cannula tube for adjusting an axial location of the depth limiter, where such a depth limiter is configured to engage dedicated threads on the cannula tube instead of the stability ribs of the cannula tube.

Figure 22:
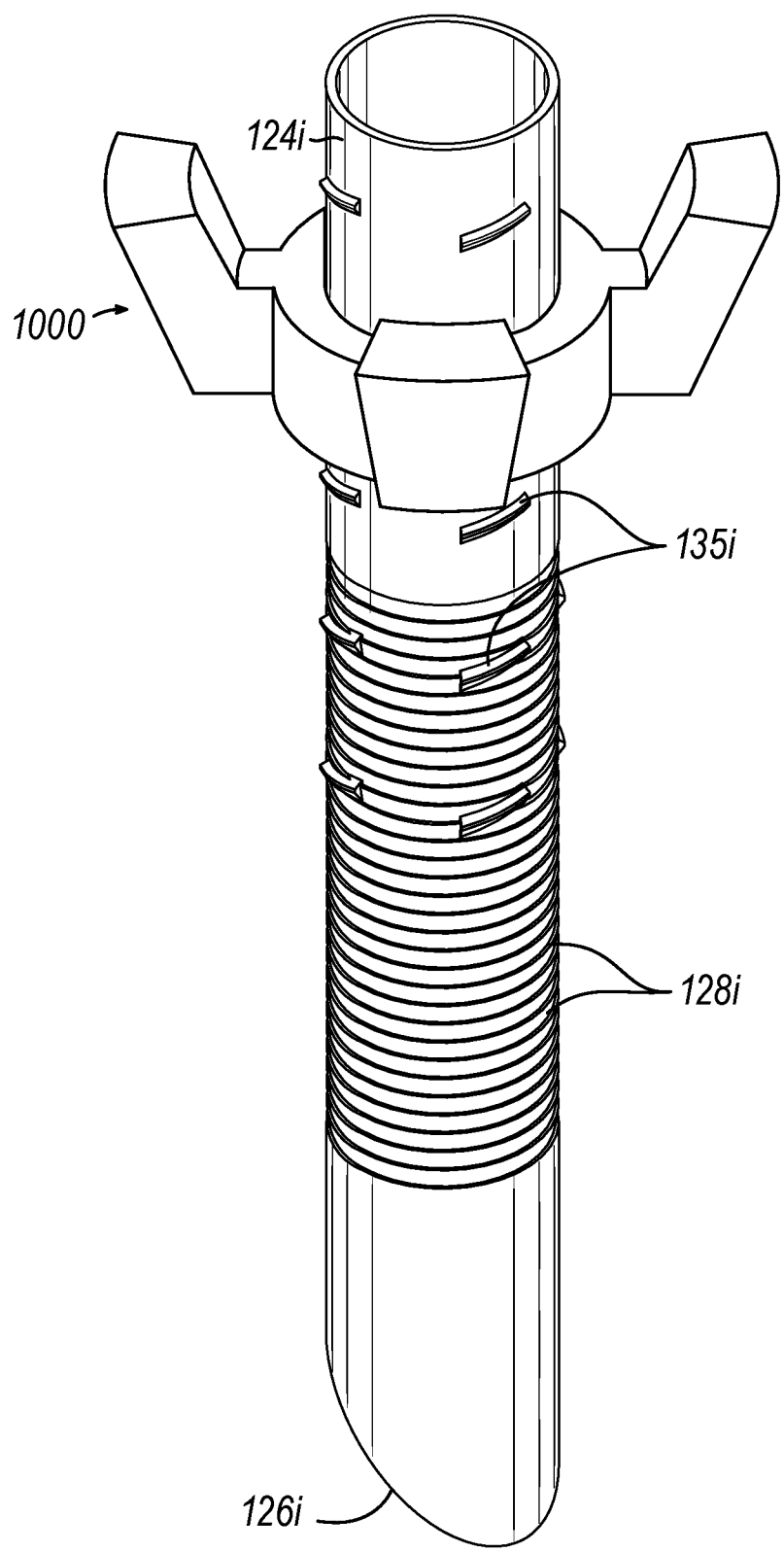
FIG. 22 depicts a perspective view of another exemplary cannula tube for the trocar of FIG. 4, showing another exemplary depth limiter selectively positioned about the cannula tube.

FIG. 22 shows another alternative cannula tube (124i) for trocar (110) terminating at a cannula tip (126i). Cannula tube (124i) is generally similar to cannula tube (124a), except that cannula tube (124i) omits flats and includes a plurality of tissue gripping features in the form of annular ribs (128i) arranged axially along a medial portion of cannula tube (124i) and which are similar to ribs (26, 128) described above. Moreover, cannula tube (124i) includes four sets (three shown) of radially-aligned helical threads (135i) arranged axially along medial-proximal and proximal portions of cannula tube (124i) such that threads (135i) partially overlap ribs (128i). Sets of threads (135i) are offset from each other by 90 degrees and are a quarter pitch apart.

FIG. 22 further shows a ninth exemplary depth limiter (1000) selectively coupled to cannula tube (124i) of trocar (110) for selectively limiting the depth to which trocar (110) may travel distally into abdominal wall (2). Depth limiter (1000) is substantially similar to depth limiter (200) and includes various similar features. Thus, only different features are described below.

Figure 23:
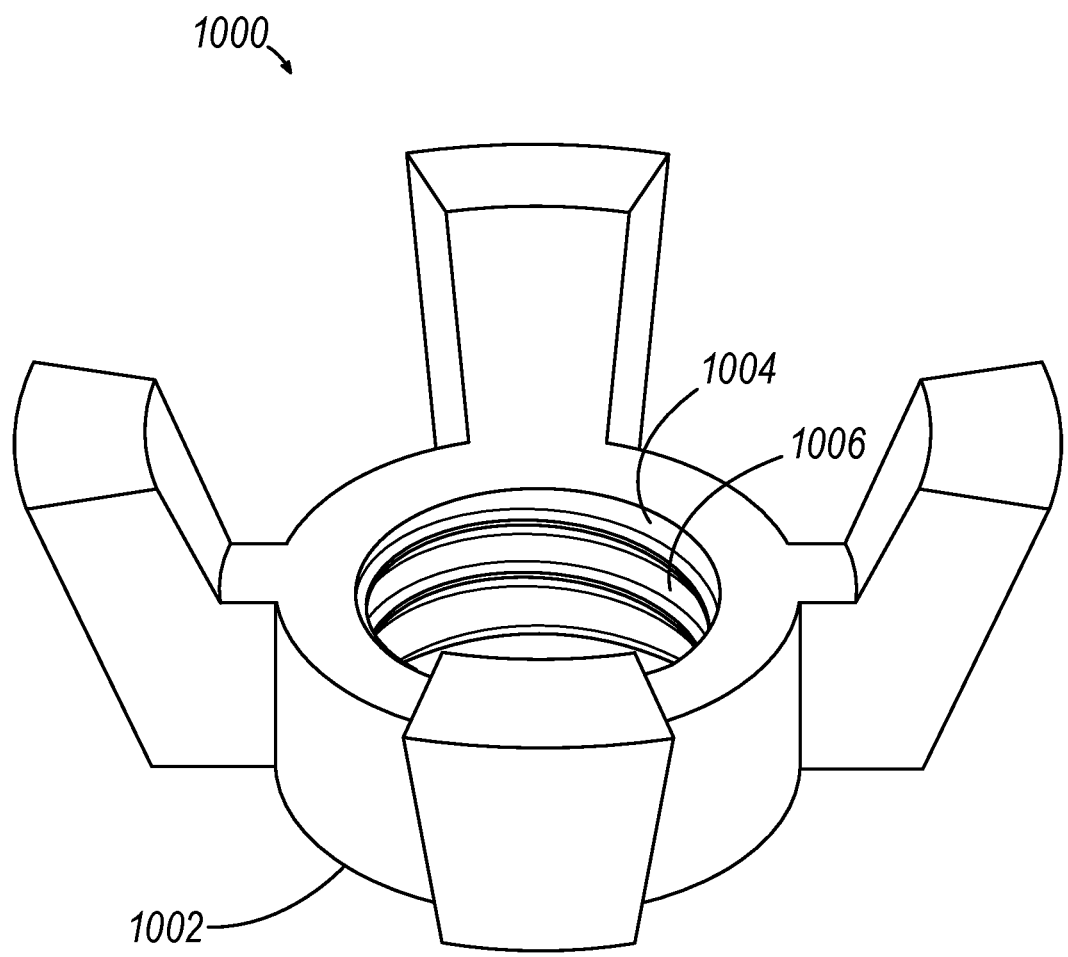
FIG. 23 depicts a perspective view of the depth limiter of FIG. 22.

As best shown in FIG. 23, depth limiter (1000) of the present version includes wingnut-shaped hub (1002) defining a generally cylindrical bore (1004) and including a helical thread (1006) extending radially inwardly from a peripheral edge of bore (914) and configured to selectively threadably engage threads (135i) of cannula tube (124i).

By providing four sets of threads (135i) and helical thread (1006) configured to threadably engage threads (135i) rather than ribs (128i), cannula tube (124i) and depth limiter (1000) may cooperate to provide a further reduced degree of relative rotation between depth limiter (1000) and cannula tube (124i) for adjusting an axial location of the depth limiter (1000) (e.g., increased axial adjustment per rotation), and may provide a reduced degree of invasiveness to tissue caused by threads (135i) while further allowing threads (135i) to coincide with ribs (128i).

J. Tenth Exemplary Depth Limiter

Figure 24:
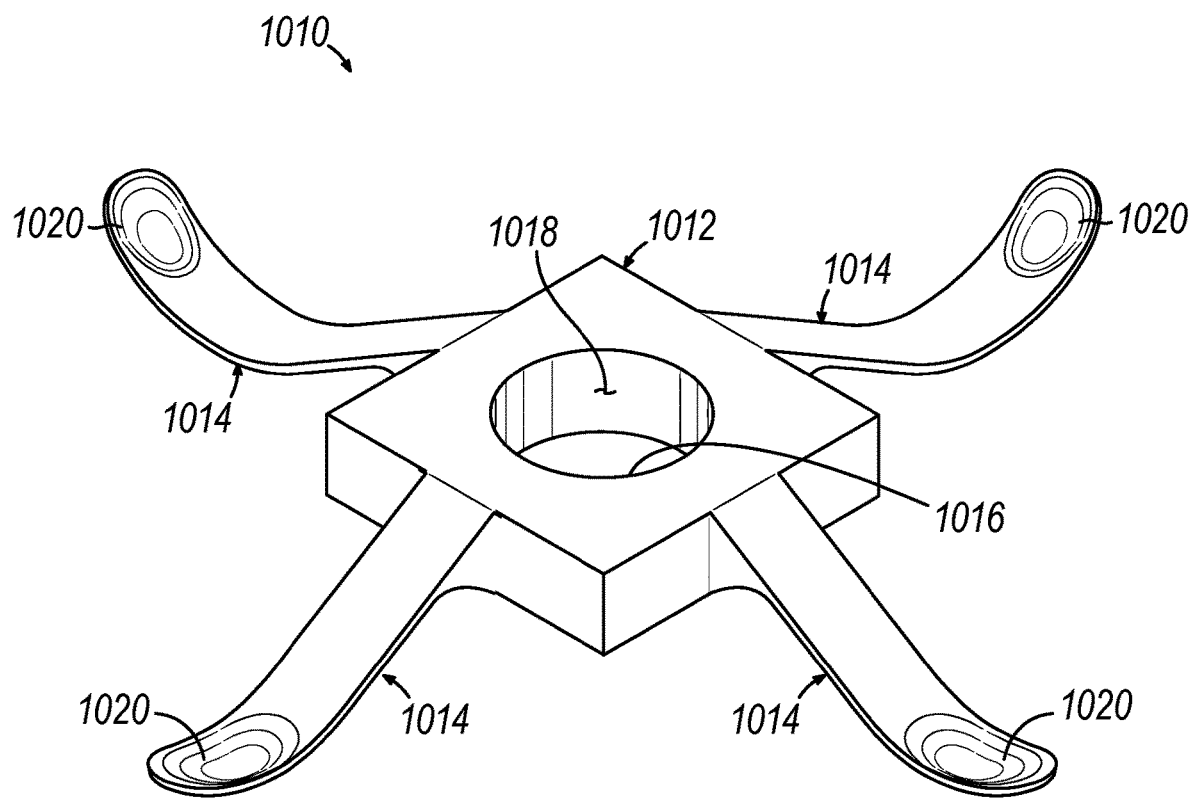
FIG. 24 depicts a perspective view of another exemplary depth limiter that includes four legs.

FIG. 24 shows a perspective view of a tenth exemplary depth limiter (1010).

Depth limiter (1010) includes a hub (1012) and a plurality of legs (1014). Depth limiter (1010) may be used in combination with depth limiters (200, 300, 400, 500, 600, 700, 800, 900, 1000) described above. While hub (1012) is shown as being generally square shaped, other shapes of hub (1012) are also envisioned. As shown, hub (1012) includes an aperture (1016) extending completely therethrough. Aperture (1016) may include a gripping surface (1018). Gripping surface (1018) may extend parallel to a longitudinal axis defined by cannula tube (22) of cannula (20). While FIGS. 24-25B describe depth limiter (1010) with reference to cannula tube (22) of trocar (10) of FIG. 1, other cannula tubes (e.g., cannula tube (124)) may also be used. Gripping surface (1018) may be smooth or non-smooth. As shown in FIG. 24, gripping surface (1018) includes a smooth surface that may frictionally engage a portion of cannula (20), such as ribs (26). Alternatively, gripping surface (1018) may include a non-smooth surface may include one or more features to lockingly engage cannula tube (22). In other words, depth limiter (1010) may be secured to cannula (20) with mating threads (like a nut) or secured to a scalloped cannula with an appropriate amount of interference fit. Such threads of depth limiter (1010) may be helical or non-helical (e.g., scallops). For example, gripping surface (1018) may include at least one tooth configured to lockingly engage with at least one of rib (26) of cannula (20).

Legs (1014) may have a generally constant cross-sectional area moving radially away from hub (1012); however, legs (1014) may have a non-uniform cross-section. For example, one or more ends of legs (1014) may include cupped portions (1020) to distribute the downward force. As shown, legs (1014) are separated by approximately 90 degrees. More or fewer legs (1014) are also envisioned.

Depth limiter (1010) may provide additional stability to the trocar (10) for anti-tip resistance. Depth limiter (1010) may be configured to restrict sudden tilting using legs (1014), thereby stabilizing cannula (20). Depth limiter (1010) is configured to prevent accidental over-insertion into body, while also restricting the displacement and/or velocity of off-axis tilting of trocar (10) to stabilize trocar (10). This stabilization may be achieved using mechanical spring effects of each leg (1014). Legs (1014) may have a reduced mass allowing legs (1014) to flex outwardly, causing a variable amount of spring-resistance in each direction trocar (10) attempts to tilt. For example, legs (1014) may have reduced mass portions (e.g., living hinge portions), and/or may rely on inherent spring force of legs (1014). Legs (1014) may contact the patient's body wall to prevent or at least decelerate tip over of cannula (20).

Figure 25A:
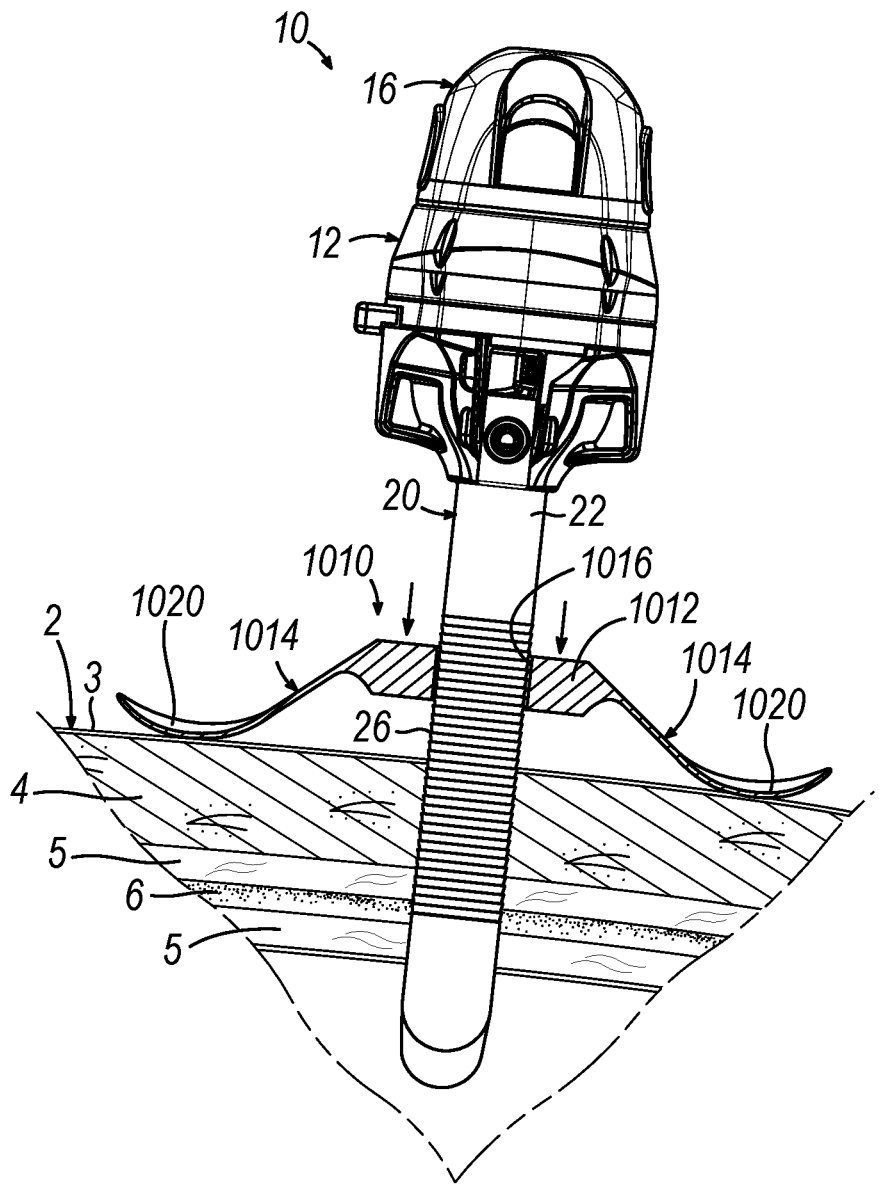
FIG. 25A depicts a partial side sectional view of the depth limiter of FIG. 24 coupled with the cannula tube of the cannula assembly of the trocar of FIG. 1, where the legs of the depth limiter are in a non-deployed configuration when the distal end of the trocar received within the abdominal cavity.
Figure 25B:
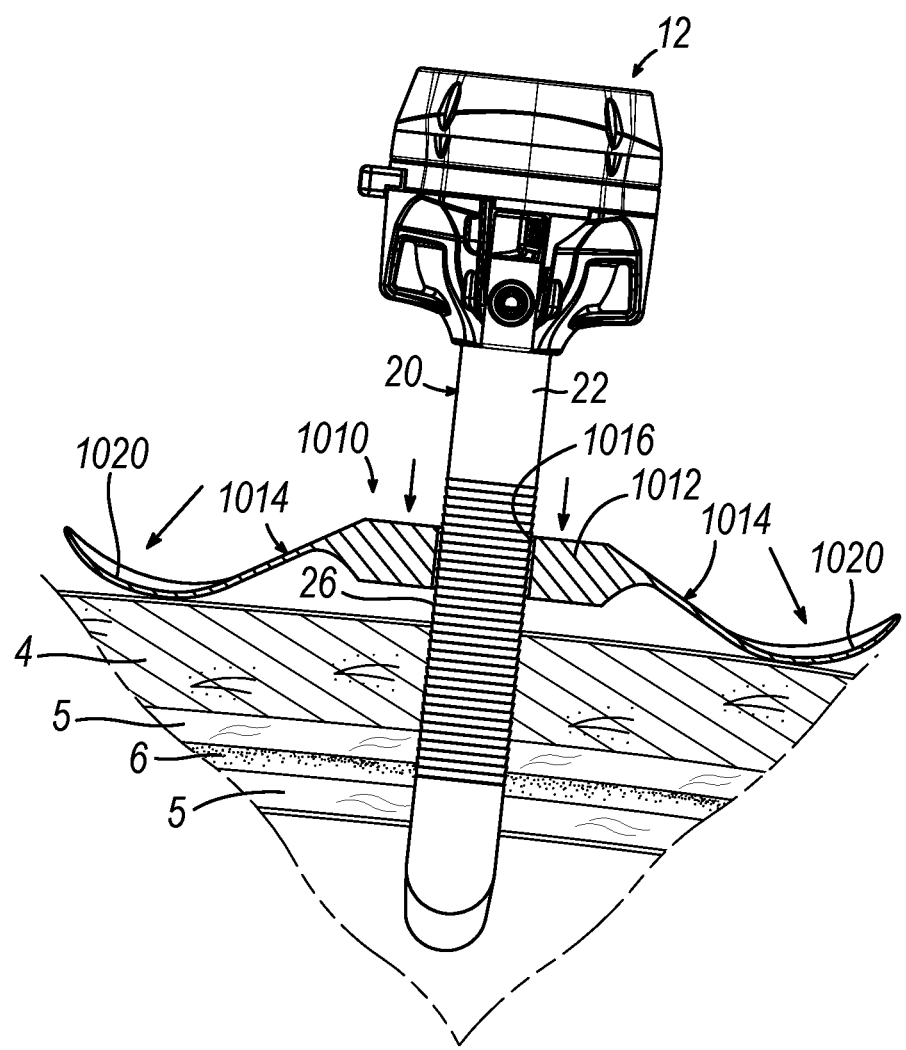
FIG. 25B depicts a partial side sectional view of the depth limiter of FIG. 24 coupled with the cannula tube of the cannula assembly of FIG. 1 following detachment and removal of the obturator, where the legs of the depth limiter are in a deployed configuration with a distal end of the cannula tube received within the abdominal cavity.

FIGS. 25A-25B show depth limiter (1010); however, the teachings of FIGS. 25A-25B may also apply to depth limiters (1110, 1210) described in detail below. FIG. 25A shows a partial side sectional view of depth limiter (1010) of FIG. 24 coupled with cannula tube (22) of cannula assembly (12) of trocar (10) of FIG. 1, where legs (1014) of depth limiter (1010) are in a non-deployed configuration when distal end of trocar (10) received within abdominal cavity (1). In the non-deployed configuration (e.g., the resting configuration) of FIG. 25A, legs (1014) may be curved downwardly. As depth limiter (1010) is pushed against abdominal wall (2), legs (1014) bend flatter and provide reaction spring-forces against abdominal wall (2) and cannula (20). The degree at which legs (1014) bend flatter may be controlled by the user. For example, additional force (e.g., downward hand pressure by the user) may cause legs (1014) to bend flatter until depth limiter (1010) is disposed adjacent to abdominal wall (2). As the flatness of legs (1014) increases, the amount of reactive forces on cannula (20) may also increase, which increases the locking force. For example, when the user has depressed depth limiter (1010) to a partially (but not fully) deployed configuration, legs (1014) may have some degree of deployment. Additionally, if the user then applies an off-axis loading, one or more of legs (1014) may depress further than the other legs (1014), but upon removal of the off-axis load, legs (1014) may be equalized and return in a controlled manner to a centered home position.

FIG. 25B shows a partial side sectional view of depth limiter (1010) of FIG. 24 coupled with cannula tube (22) of cannula assembly (12) of FIG. 1 following detachment and removal of obturator (16), where legs (1014) of depth limiter (1010) are in a deployed configuration with a distal end of cannula tube (22) received within abdominal cavity (1). In the deployed configuration, legs (1014) may reduce the amount of rotational displacement/tilt that trocar (10)) may achieve, and may also reduce the velocity that trocar (10) may achieve that tilt (i.e., preventing sudden accidental moves within the body). To completely undeploy depth limiter (1010) from cannula tube (22), the user may retract cannula (20) out of abdominal wall (2) to sufficiently reduce the compressive/clamping forces of depth limiter (1010) on the abdominal wall (2), such that the user may pull the depth limiter (1010) back using their hand. Depth limiter (1010) may be disposable or re-usable.

K. Eleventh Exemplary Depth Limiter

Figure 26:
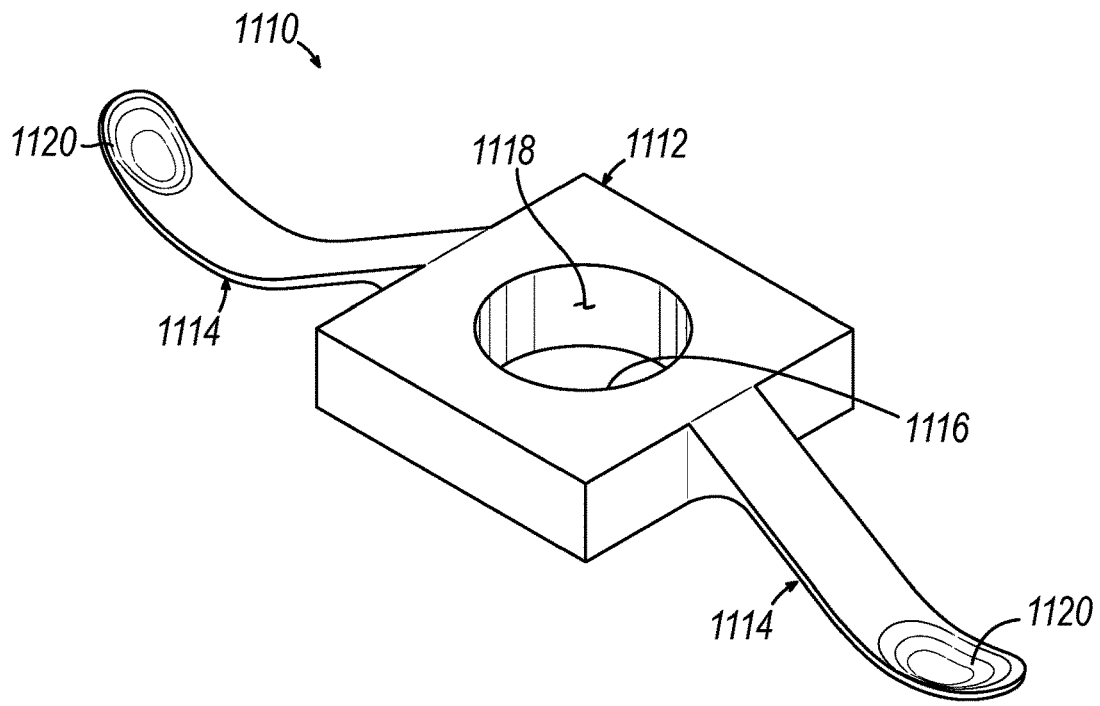
FIG. 26 depicts a perspective view of another exemplary depth limiter that includes two legs.

FIG. 26 shows an eleventh exemplary depth limiter (1110) that is similar to depth limiter (1010). Depth limiter (1110) includes a hub (1112) similar to hub (1012), legs (1114) similar to legs (1014), an aperture (1116) similar to aperture (1016), a gripping surface (1118) of aperture (1116) similar to gripping surface (1018). Legs (1114) may include cupped portions (1120) similar to cupped portions (1020). Unlike depth limiter (1010) that is shown as including four legs (1014), depth limiter (1110) includes two legs (1114). For example, legs (1114) may be separated by approximately 180 degrees. Legs (1114) flex similar to legs (1014) shown above with reference to FIGS. 25A-25B.

L. Twelfth Exemplary Depth Limiter

Figure 27:
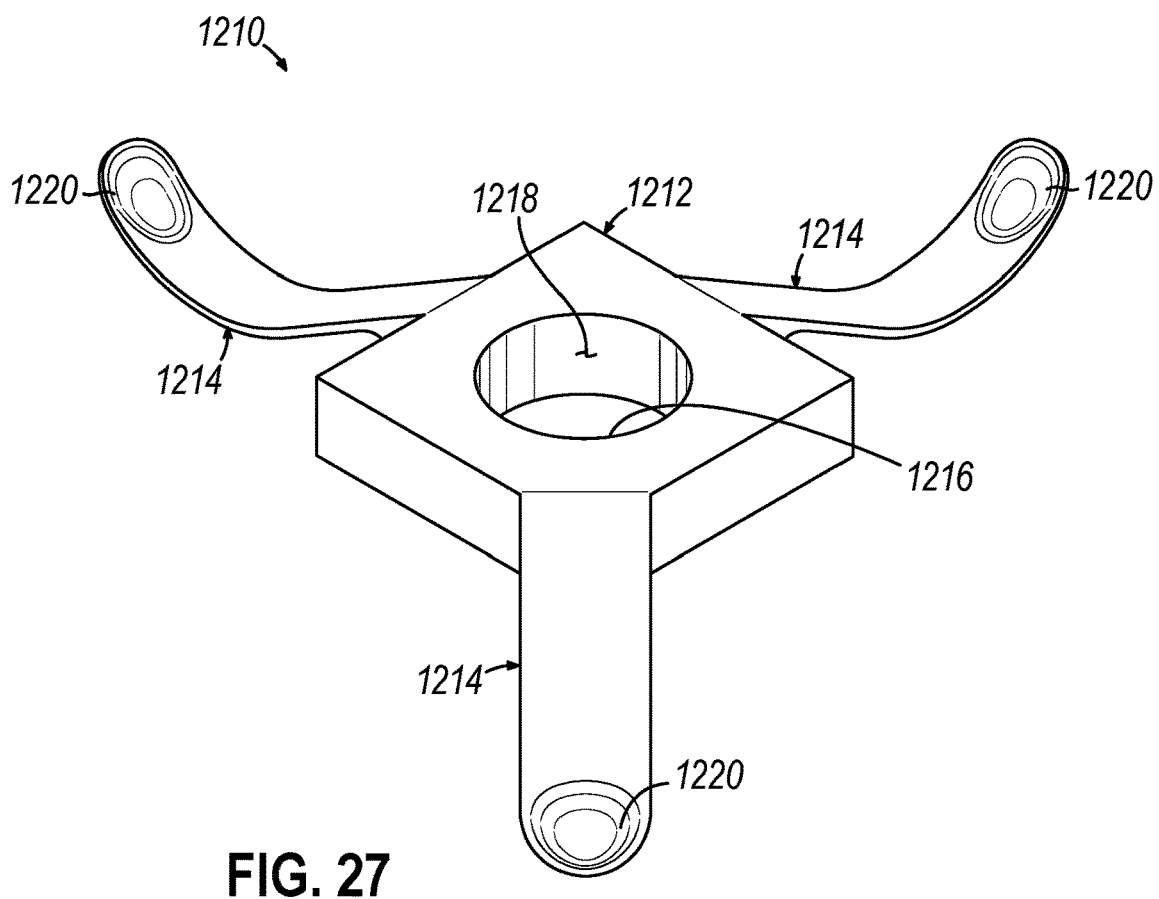
FIG. 27 depicts a perspective view of another exemplary depth limiter that includes three legs.

FIG. 27 shows a twelfth exemplary depth limiter (1210) that is similar to depth limiters (1010, 1110). Depth limiter (1210) includes a hub (1212) similar to hub (1012), legs (1214) similar to legs (1014), an aperture (1216) similar to aperture (1016), a gripping surface (1218) of aperture (1216) similar to gripping surface (1018). Legs (1114) may include cupped portions (1220) similar to cupped portions (1020). Unlike depth limiter (1010) that is shown as including four legs (1014), depth limiter (1210) includes three legs (1214). For example, legs (1214) may be circumferentially separated uniformly by approximately 120 degrees around hub (1212). However, legs (1214) may be non-uniformly separated. In some instances, the use of three or four legs (1014, 1214, 1314, 1414) may allow for further stability and ergonomics to allow for finger grip of user (U). Legs (1214) may flex similar to legs (1014) shown above with reference to FIGS. 25A-25B.

M. Thirteenth Exemplary Depth Limiter

FIGS. 28-30B show a thirteenth exemplary depth limiter (1310). Particularly, FIG. 28 shows a perspective view of depth limiter (1310). As shown, depth limiter (1310) includes a hub (1312) and a plurality of legs (1314). extending from hub (1312). Depth limiter (1310) may be used in combination with any one or more of depth limiters (200, 300, 400, 500, 600, 700, 800, 900, 1000) described above. While hub (1312) is shown as being generally cylindrically shaped, other shapes of hub (1312) are also envisioned. As shown, hub (1312) includes an aperture (1316) and a plurality of notches (1318). Notches (1318) may transform depth limiter (1310) from a movable configuration to a fixed configuration.

Aperture (1316) includes a gripping surface (1320) that is configured to couple with the outer surface of cannula tube (124) in the fixed configuration. Gripping surface (1320) may extend parallel to a longitudinal axis defined by cannula tube (124) of cannula (120). While FIGS. 28-30B describe depth limiter (1310) with reference to cannula tube (124) of trocar (110), other cannula tubes (e.g., cannula tube (22)) may also be used. Gripping surface (1320) may be smooth or non-smooth. As shown in FIG. 28, gripping surface (1320) may include a smooth surface that frictionally engages ribs (128) of cannula (120) in the fixed configuration. Alternatively, gripping surface (1320) may include a non-smooth surface may include one or more features to lockingly engage cannula tube (124). Hub (1312) of depth limiter (1310) may be secured to cannula (120) with mating threads (like a nut) or may be secured to a scalloped cannula using an interference fit. Threads may be helical or non-helical (e.g., scallops). For example, gripping surface (1320) may include at least one tooth configured to lockingly engage with at least one of rib (128) of cannula (120). For example, notches (1318) may be formed in hub (1312) of depth limiter (1310), such that each leg (1314) may selectively collapse when adequate force acts on that leg (1314), causing gripping surface (1320) to clamp down tighter on cannula (120). As such, depth limiter (1310) may limit insertion depth of cannula tube (124) of cannula (120) and provide stability control of cannula tube (124) of cannula (120).

Legs (1314) may have a generally tapering cross-section moving radially away from hub (1312). For example, one or more ends of legs (1314) may include distal pad (1322) to distribute the downward force. As shown, legs (1314) are separated by approximately 90 degrees. Legs (1314) may be non-uniformly separated. Additionally, more or fewer legs (1314) are also envisioned (similar to those shown in FIGS. 26-27 associated with depth limiters (1110, 1210). Depth limiter (1310) may provide additional stability to the trocar (110) for anti-tip resistance. Depth limiter (1310) may be configured to restrict sudden tilting using legs (1314), thereby stabilizing cannula (120). Legs (1314) may contact body wall to prevent or at least decelerate tip over of cannula (120).

Figure 30A:
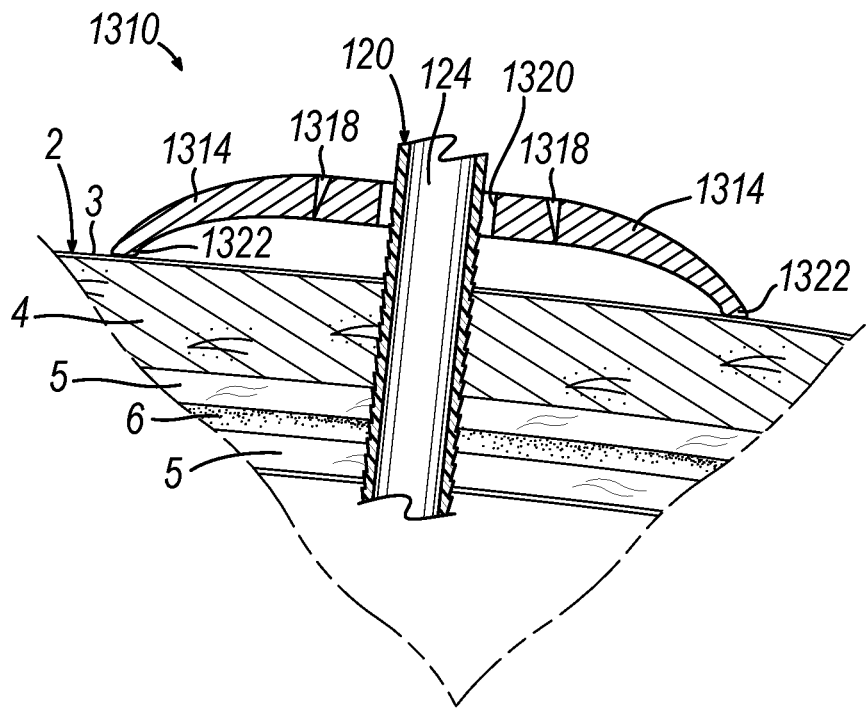
FIG. 30A depicts a partial side sectional view of the depth limiter of FIG. 28 coupled with the cannula tube of the cannula assembly of FIG. 5, where the legs of the depth limiter are in a non-deployed configuration.

FIGS. 29A and 30A show depth limiter (1310) in the movable configuration. Particularly, FIG. 29A shows a top plan view of depth limiter (1310) of FIG. 28 coupled with cannula tube (124) of cannula assembly (112) of FIG. 5, where hub (1312) of depth limiter (1310) is in a movable configuration. FIG. 30A shows a partial side sectional view of depth limiter (1310) of FIG. 28 coupled with cannula tube (124) of cannula assembly (112) of FIG. 5, where legs (1314) of depth limiter (1310) are in the movable configuration. In the movable configuration of FIGS. 29A and 30A, gripping surface (1320) forms a second effective diameter (ED2) that allows for axial movement of depth limiter (1310) relative to an outer diameter of cannula tube (124) of cannula (112). In the movable configuration, also considered the resting configuration, legs (1314) are curved downwardly. Once pushed against abdominal wall (2), legs (1314) bend flatter and provide a reaction force against abdominal wall (2) and cannula (120).

Figure 30B:
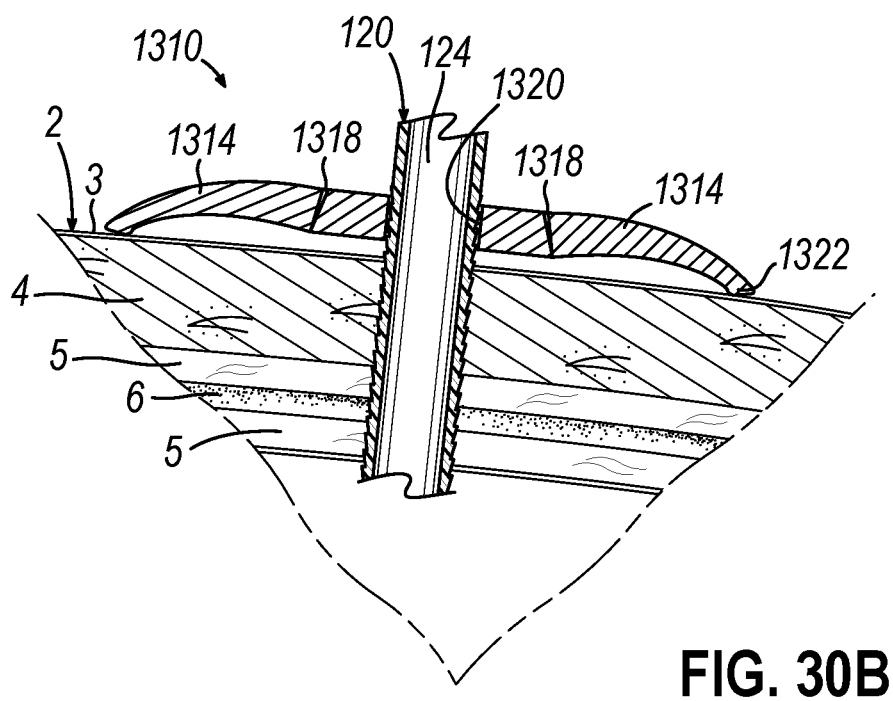
FIG. 30B depicts a partial side sectional view of the depth limiter of FIG. 28 coupled with the cannula tube of the cannula assembly of FIG. 5 following detachment and removal of the obturator, where the legs of the depth limiter are in a deployed configuration.

FIGS. 29B and 30B show depth limiter (1310) in the fixed configuration.

Particularly, FIG. 29B shows a partial side sectional view of depth limiter (1310) of FIG. 28 coupled with cannula tube (124) of cannula assembly (112) of FIG. 5 following detachment and removal of obturator (116), where legs (1314) of depth limiter (1310) are in the fixed configuration. FIG. 30B shows a partial side sectional view of depth limiter (1310) of FIG. 28 coupled with cannula tube (124) of cannula assembly (112) of FIG. 5 following detachment and removal of obturator (116), where legs (1314) of depth limiter (1310) are in the fixed configuration. In the fixed configuration, notches (1318) may be forced closed to narrow aperture (1316). Legs (1314) may reduce the amount of rotational displacement/tilt that trocar (110) may exhibit, and may also reduce the velocity at which trocar (110) may assume that tilt (i.e., preventing sudden movements within the body). In the fixed configuration, gripping surfaces (1320) collectively form a first effective diameter (ED1) that restricts axial movement of depth limiter (1310) relative to cannula (120) by directly contacting cannula (120). Depth limiter (1310) may be disposable or reusable.

N. Fourteenth Exemplary Depth Limiter

Figure 31:
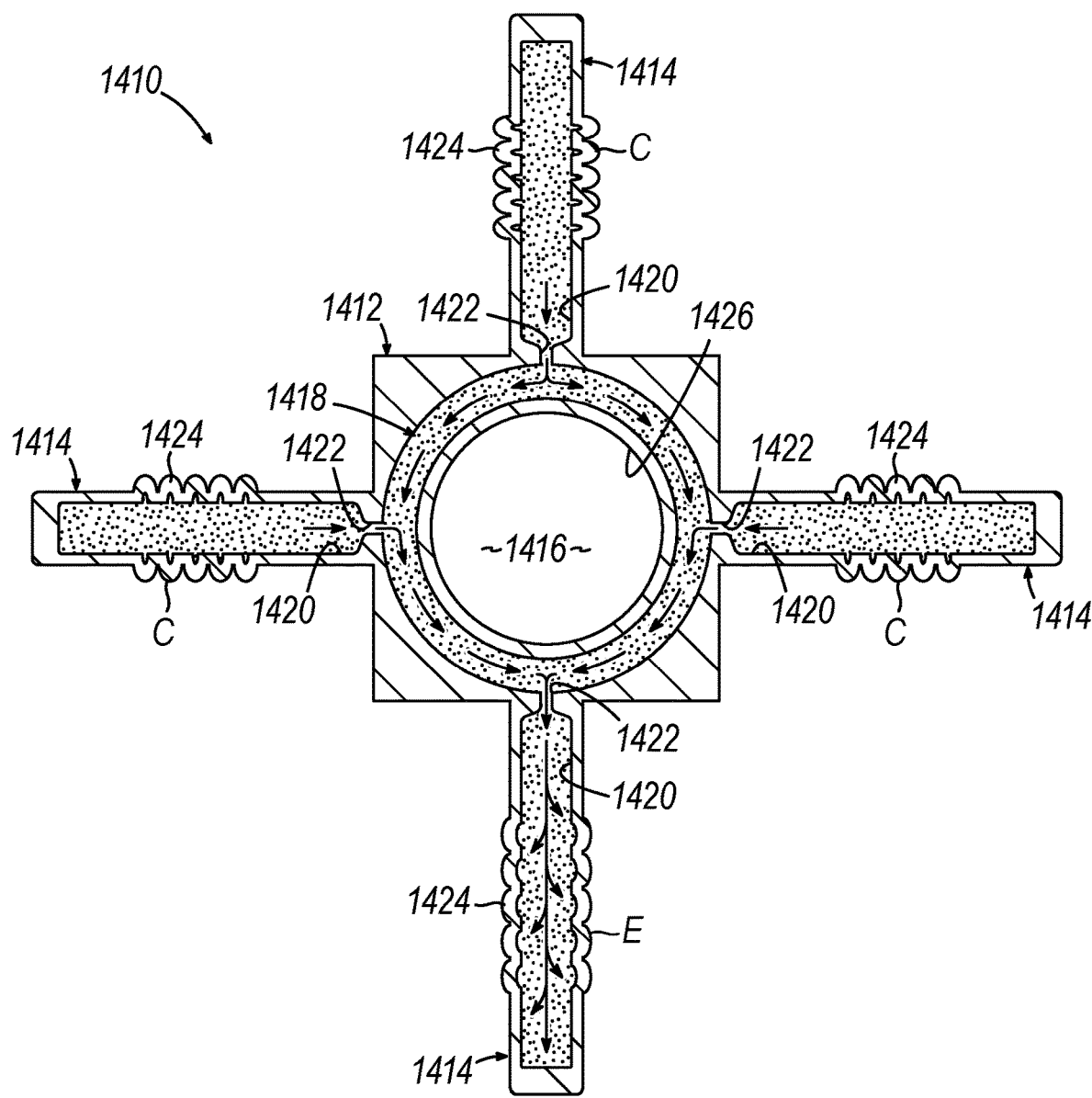
FIG. 31 depicts a top sectional view of another exemplary depth limiter that includes a fluid chamber and four legs.

FIG. 31 shows a top sectional view of a fourteenth exemplary depth limiter (1410). Depth limiter (1410) includes a hub (1412) and a plurality of legs (1414) extending from hub (1412). Depth limiter (1410) may be used in combination with any one or more of depth limiters (200, 300, 400, 500, 600, 700, 800, 900, 1000) described above. In some versions, hub (1412) may being generally cylindrically shaped. As shown, hub (1412) includes an aperture (1416) configured to receive cannula tube (124) of cannula (120). As shown, legs (1414) may be separated by approximately 90 degrees. However, legs (1414) may be non-uniformly separated. Additionally, more or fewer legs (1414) are also envisioned, similar to depth limiters (1110, 1210) shown in FIGS. 26-27.

Depth limiter (1410) includes a fluid chamber (1418) that may be disposed within hub (1412) and legs (1414). For example, fluid chamber (1418) may be completely enclosed by hub (1412) and legs (1414). Fluid chamber may include a plurality of fluid passageways (1420) that include narrow portions (1422). Narrow portions (1422) may be disposed generally between hub (1412) and legs (1414). Narrow portions (1422) regulate flow between hub (1412) and legs (1414). In other words, fluid chamber (1418) may be integrated into legs (1414) with narrow portions (1422) forming restricted areas of flow at the base of each leg (1414). As shown, one or more ends of legs (1414) may include extensive portion (1424) configured to extend from a compressed configuration (C) to an expanded configuration (E). Depth limiter (1410) may provide additional stability to the trocar (110) for anti-tip resistance. As additional tilt force acts on each independent leg (1414), the fluid may redistribute to the other legs (1414), but the fluid may be restricted by these restricted areas (1422), thus creating a damping effect on the tilting of trocar (110). This damping effect may regulate the speed at which trocar (110) tilts. As a result, depth limiter (1410) may restrict sudden tilting of trocar (110) via restricted fluid flow between legs (1414), thereby stabilizing cannula (120).

Aperture (1416) includes a gripping surface (1426) that may couple with the outer surface of cannula tube (124) of cannula (120). Gripping surface (1426) may extend parallel to a longitudinal axis defined by cannula tube (124) of cannula (120). Gripping surface (1426) may be smooth or non-smooth. As shown in FIG. 31, gripping surface (1426) may include a smooth surface that frictionally engages ribs (128) of cannula (120). Alternatively, gripping surface (1426) may include a non-smooth surface may include one or more features to lockingly engage cannula tube (124). For example, hub (1412) of depth limiter (1410) may be secured to cannula (120) using mating threads (like a nut) or secured to a scalloped cannula. Threads may be helical or non-helical (e.g., scallops). For example, gripping surface (1426) may include at least one tooth configured to lockingly engage with at least one of rib (128) of cannula (120). Depth limiter (1410) may be disposable.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical access device assembly comprising: (a) a cannula including: (i) a working channel configured to guide a surgical instrument along a central axis of the cannula, and (ii) at least one helical tissue engagement feature disposed along an outer surface of the cannula, wherein the helical tissue engagement feature is configured to stabilize the cannula relative to a body cavity wall of a patient when the cannula is inserted distally through the body cavity wall; and (b) a depth limiter movably coupled with the cannula, wherein the depth limiter comprises at least one body portion extending about a central axis of the depth limiter and including at least one protrusion extending radially inwardly relative to the central axis of the depth limiter, wherein the at least one body portion is movable angularly relative to the cannula between a fine adjustment configuration and a coarse adjustment configuration, wherein in the fine adjustment configuration the at least one protrusion is configured to selectively threadably engage the at least one helical tissue engagement feature, wherein in the coarse adjustment configuration the at least one protrusion is configured to selectively threadably disengage the at least one helical tissue engagement feature such that the depth limiter is translatable axially along the cannula.

Example 2

The surgical access device assembly of Example 1, wherein the at least one protrusion includes a plurality of circumferentially arranged protrusions.

Example 3

The surgical access device assembly of any of the preceding Examples, wherein the cannula includes at least one longitudinal track disposed along the outer surface of the cannula, wherein in the coarse adjustment configuration the at least one protrusion is configured to selectively slidably engage the at least one longitudinal track.

Example 4

The surgical access device assembly of Example 3, wherein the at least one body portion includes first and second body portions rotatable relative to each other about the central axis of the depth limiter, wherein the at least one protrusion includes a first protrusion presented by the first body portion and a second protrusion presented by the second body portion.

Example 5

The surgical access device assembly of Example 4, wherein the first and second body portions are rotatable relative to each other about the central axis of the depth limiter between a clocked configuration in which the first and second protrusions are radially aligned with each other and at least one unclocked configuration in which the first and second protrusions are radially misaligned from each other.

Example 6

The surgical access device assembly of Example 5, wherein at least one of the first or second protrusions is configured to selectively threadably engage the at least one helical tissue engagement feature in response to the first and second body portions being in the unclocked configuration.

Example 7

The surgical access device assembly of Example 6, wherein the at least one longitudinal track has a width, and wherein the first and second protrusions collectively occupy an envelope having an effective width greater than the width of the at least one longitudinal track when the first and second body portions are in the unclocked configuration.

Example 8

The surgical access device assembly of any one or more of Examples 5 through 7, wherein the first and second protrusions are configured to selectively slidably engage the at least one longitudinal track when the first and second body portions are in the clocked configuration.

Example 9

The surgical access device assembly of Example 8, wherein the at least one longitudinal track has a width, and wherein the first and second protrusions collectively occupy an envelope having an effective width less than the width of the at least one longitudinal track when the first and second body portions are in the clocked configuration.

Example 10

The surgical access device assembly of any one or more of Examples 5 through 9, wherein the first and second body portions are biased toward the unclocked configuration.

Example 11

The surgical access device assembly of any of the preceding Examples, wherein the at least one body portion includes first and second body portions pivotably coupled together by a hinge such that the first and second body portions are pivotable relative to each other about the hinge between the fine adjustment configuration and the coarse adjustment configuration, wherein the at least one protrusion includes a first protrusion presented by the first body portion and a second protrusion presented by the second body portion.

Example 12

The surgical access device assembly of Example 11, wherein the first and second protrusions are configured to be pivoted radially outwardly from the at least one helical tissue engagement feature when in the coarse adjustment configuration.

Example 13

The surgical access device assembly of any one or more of Examples 11 through 12, wherein the hinge includes a living hinge.

Example 14

The surgical access device assembly of Example 13, wherein the first and second body portions and the living hinge are integrally formed together as a unitary piece.

Example 15

The surgical access device assembly of any one or more of Examples 11 through 14, wherein the first and second body portions are biased toward the fine adjustment configuration.

Example 16

A depth limiter configured to couple with a cannula tube of a trocar having at least one helical tissue engagement feature disposed along an outer surface of the cannula tube, the depth limiter comprising: (a) a first body portion; (b) a second body portion movably coupled to the first body portion such that the first and second body portions are movable relative to each other between a fine adjustment configuration and a coarse adjustment configuration; (c) at least one first protrusion presented by the first body portion and extending radially inwardly relative to a central axis of the depth limiter; and (d) at least one second protrusion presented by the second body portion and extending radially inwardly relative to the central axis of the depth limiter, wherein in the fine adjustment configuration at least one of the first or second protrusions is configured to selectively threadably engage the at least one helical tissue engagement feature of the cannula tube, wherein in the coarse adjustment configuration the first and second protrusions are configured to selectively threadably disengage the at least one helical tissue engagement feature of the cannula tube.

Example 17

The depth limiter of Example 16, wherein the first and second body portions are rotatable relative to each other about the central axis of the depth limiter between a clocked configuration in which the first and second protrusions are radially aligned with each other and at least one unclocked configuration in which the first and second protrusions are radially misaligned from each other, wherein the clocked configuration at least partially defines the coarse adjustment configuration and the unclocked configuration at least partially defines the fine adjustment configuration.

Example 18

The depth limiter of Example 16, wherein the first and second body portions are pivotable relative to each other about a hinge axis perpendicular to the central axis of the depth limiter between the fine adjustment configuration and the coarse adjustment configuration.

Example 19

A method of using a depth limiter with a trocar, wherein the depth limiter includes at least one body portion extending about a central axis of the depth limiter and having at least one protrusion extending radially inwardly relative to the central axis of the depth limiter, the method comprising: (a) positioning the at least one body portion about a cannula tube of a trocar having at least one helical tissue engagement feature; (b) moving the at least one body portion relative to the cannula tube between a fine adjustment configuration in which the at least one protrusion selectively threadably engages the at least one helical tissue engagement feature and a coarse adjustment configuration in which the at least one protrusion selectively threadably disengages the at least one helical tissue engagement feature; (c) moving the at least one body portion helically relative to the cannula tube while in the fine adjustment configuration; and (d) translating the at least one body portion relative to the cannula tube while in the coarse adjustment configuration.

Example 20

The method of Example 19, wherein moving the at least one body portion relative to the cannula tube between the fine adjustment configuration and the coarse adjustment configuration includes angularly moving the at least one body portion relative to the cannula tube.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pat. Pub. No. 2021/0338281 on Nov. 4, 2021; U.S. patent application Ser. No. 17/213,401, entitled "Pinch-To-Clamp Cannula Depth Limiter," filed on Mar. 26, 2021, issued as U.S. Pat. No. 11,980,392 on May 14, 2024; U.S. patent application Ser. No. 17/213,409, entitled "Universal Size Multi-Walled Elastomer Cannula Depth Limiter," filed on Mar. 26, 2021, issued as U.S. Pat. No. 11,986,215 on May 21, 2024; U.S. patent application Ser. No. 17/213,426, entitled "Tilting Tang Cannula Depth Limiter," filed on Mar. 26, 2021, issued as U.S. Pat. No. 11,712,267 on Aug. 1, 2023; U.S. patent application Ser. No. 17/213,431, entitled "Two Piece Separable Obturator," filed on Mar. 26, 2021, issued as U.S. Pat. No. 11,980,393 on May 14, 2023; U.S. patent application Ser. No. 17/213,434, entitled "Latchless Obturator with Interference Fit Feature," filed on Mar. 26, 2021, issued as U.S. Pat. No. 11,974,773 on May 7, 2024; U.S. patent application Ser. No. 17/213,437, entitled "Balancing Feature for Reusable Trocar," filed on Mar. 26, 2021, issued as U.S. Pat. No. 11,559,329 on Jan. 24, 2023; U.S. patent application Ser. No. 17/213,508, entitled "Airflow Channels and Patterns in Lumen for Cannula," filed on Mar. 26, 2021, issued as U.S. Pat. No. 12,035,941 on Jul. 16, 2024; and/or U.S. patent application Ser. No. 17/213,518, entitled "Stabilizer for Surgical Shafts or Cannulas," filed on Mar. 26, 2021, issued as U.S. Pat. No. 12,042,342 on Jul. 23, 2024. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical access device assembly comprising:
    (a) a cannula including:
        (i) a working channel configured to guide a surgical instrument along a central axis of the cannula,
        (ii) at least one helical tissue engagement feature disposed along an outer surface of the cannula, wherein the helical tissue engagement feature is configured to stabilize the cannula relative to a body cavity wall of a patient when the cannula is inserted distally through the body cavity wall, and
        (iii) at least one longitudinal track disposed along the outer surface of the cannula; and
    (b) a depth limiter movably coupled with the cannula, wherein the depth limiter comprises:
        (i) a first body portion,
        (ii) a second body portion, wherein each of the first and second body portions extends about a central axis of the depth limiter, and
        (iii) at least one protrusion extending radially inwardly relative to the central axis of the depth limiter,
        wherein the first and second body portions are rotatable relative to one another and relative to the cannula about the central axis between a fine adjustment configuration and a coarse adjustment configuration, wherein in the fine adjustment configuration the at least one protrusion is configured to selectively threadably engage the at least one helical tissue engagement feature, wherein in the coarse adjustment configuration the at least one protrusion is configured to selectively threadably disengage the at least one helical tissue engagement feature and selectively slidably engage the at least one longitudinal track such that the depth limiter is translatable axially along the cannula.

2. The surgical access device assembly of claim 1, wherein the at least one protrusion includes a plurality of circumferentially arranged protrusions.

3. The surgical access device assembly of claim 1, wherein the at least one protrusion includes a first protrusion presented by the first body portion and a second protrusion presented by the second body portion.

4. The surgical access device assembly of claim 3, wherein the first and second body portions are rotatable relative to each other about the central axis of the depth limiter between a clocked configuration in which the first and second protrusions are radially aligned with each other and at least one unclocked configuration in which the first and second protrusions are radially misaligned from each other.

5. The surgical access device assembly of claim 4, wherein at least one of the first or second protrusions is configured to selectively threadably engage the at least one helical tissue engagement feature in response to the first and second body portions being in the unclocked configuration.

6. The surgical access device assembly of claim 5, wherein the at least one longitudinal track has a width, and wherein the first and second protrusions collectively occupy an envelope having an effective width greater than the width of the at least one longitudinal track when the first and second body portions are in the unclocked configuration.

7. The surgical access device assembly of claim 4, wherein the first and second protrusions are configured to selectively slidably engage the at least one longitudinal track when the first and second body portions are in the clocked configuration.

8. The surgical access device assembly of claim 7, wherein the at least one longitudinal track has a width, and wherein the first and second protrusions collectively occupy an envelope having an effective width less than the width of the at least one longitudinal track when the first and second body portions are in the clocked configuration.

9. The surgical access device assembly of claim 4, wherein the first and second body portions are biased toward the unclocked configuration.

10. The surgical access device assembly of claim 1, wherein the at least one body portion includes first and second body portions pivotably coupled together by a hinge such that the first and second body portions are pivotable relative to each other about the hinge between the fine adjustment configuration and the coarse adjustment configuration, wherein the at least one protrusion includes a first protrusion presented by the first body portion and a second protrusion presented by the second body portion.

11. The surgical access device assembly of claim 10, wherein the first and second protrusions are configured to be pivoted radially outwardly from the at least one helical tissue engagement feature when in the coarse adjustment configuration.

12. The surgical access device assembly of claim 10, wherein the hinge includes a living hinge.

13. The surgical access device assembly of claim 12, wherein the first and second body portions and the living hinge are integrally formed together as a unitary piece.

14. The surgical access device assembly of claim 10, wherein the first and second body portions are biased toward the fine adjustment configuration.

15. A depth limiter configured to couple with a cannula tube of a trocar having at least one helical tissue engagement feature disposed along an outer surface of the cannula tube, the depth limiter comprising:
(a) a first body portion;
(b) a second body portion movably coupled to the first body portion such that the first and second body portions are movable relative to each other between a fine adjustment configuration and a coarse adjustment configuration;
(c) a first protrusion presented by the first body portion and extending radially inwardly relative to a central axis of the depth limiter; and
(d) a second protrusion presented by the second body portion and extending radially inwardly relative to the central axis of the depth limiter,
wherein in the fine adjustment configuration at least one of the first or second protrusions is configured to selectively threadably engage the at least one helical tissue engagement feature of the cannula tube, wherein in the coarse adjustment configuration the first and second protrusions are configured to selectively threadably disengage the at least one helical tissue engagement feature of the cannula tube,
wherein the first and second body portions are rotatable relative to each other about the central axis of the depth limiter between a clocked configuration in which the first and second protrusions are radially aligned with each other and an unclocked configuration in which the first and second protrusions are radially misaligned from each other, wherein the clocked configuration at least partially defines the coarse adjustment configuration and the unclocked configuration at least partially defines the fine adjustment configuration.

16. The depth limiter of claim 15, wherein the first and second body portions are pivotable relative to each other about a hinge axis perpendicular to the central axis of the depth limiter between the fine adjustment configuration and the coarse adjustment configuration.

17. A surgical access device assembly comprising:
(a) a cannula including:
(i) a working channel configured to guide a surgical instrument along a central axis of the cannula, and
(ii) a helical tissue engagement protrusion disposed along an outer surface of the cannula, wherein the helical tissue engagement protrusion is configured to stabilize the cannula relative to a body cavity wall of a patient when the cannula is inserted distally through the body cavity wall; and
(b) a depth limiter movably coupled with the cannula and configured to limit a depth of the cannula relative to the body cavity wall, wherein the depth limiter comprises:
(i) a first body portion that extends about a central axis of the depth limiter, and
(ii) a second body portion that extends about the central axis,
wherein the first and second body portions are rotatable relative to each other about the central axis and relative to the cannula between a fine adjustment configuration and a coarse adjustment configuration,
wherein in the fine adjustment configuration at least one of the first or second body portions is threadably engaged with helical tissue engagement protrusion,
wherein in the coarse adjustment configuration each of the first and second body portions is threadably disengaged from the helical tissue engagement protrusion such that the depth limiter is axially translatable relative to the cannula.

18. The surgical access device of claim 17, wherein the first body portion includes a first protrusion and the second body portion includes a second protrusion, wherein in the fine adjustment configuration at least one of the first or second protrusions is threadably engaged with the helical tissue engagement protrusion, and wherein in the coarse adjustment configuration each of the first and second protrusions is threadably disengaged from the helical tissue engagement protrusion such that the depth limiter is translatable axially along the cannula.

19. The surgical access device of claim 18, wherein first and second protrusions are of equal radial height.

20. The surgical access device of claim 18, wherein the depth limiter includes a biasing spring positioned between the first body portion and second body portion, wherein the biasing spring is configured to bias the first and second body portions relative to one another such that first and second protrusions are radially unaligned with each other.

* * * * *